(12) United States Patent
Abbitt et al.

(10) Patent No.: US 10,538,775 B2
(45) Date of Patent: Jan. 21, 2020

(54) TERMINATOR SEQUENCE FOR GENE EXPRESSION IN PLANTS

(75) Inventors: Shane E Abbitt, Ankeny, IA (US); Rudolf Jung, Lohr am Main (DE)

(73) Assignee: PIONEER HI-BRED INTERNATIONAL, INC. IA (US)

(*) Notice: Subject to any disclaimer, the term of this patent is extended or adjusted under 35 U.S.C. 154(b) by 55 days.

(21) Appl. No.: 14/236,499

(22) PCT Filed: Jul. 23, 2012

(86) PCT No.: PCT/US2012/047901
§ 371 (c)(1),
(2), (4) Date: May 5, 2014

(87) PCT Pub. No.: WO2013/019461
PCT Pub. Date: Feb. 7, 2013

(65) Prior Publication Data
US 2015/0074845 A1    Mar. 12, 2015

Related U.S. Application Data

(60) Provisional application No. 61/514,055, filed on Aug. 2, 2011.

(51) Int. Cl.
*C12N 15/00* (2006.01)
*C12N 15/82* (2006.01)

(52) U.S. Cl.
CPC ......... *C12N 15/8216* (2013.01); *C12N 15/00* (2013.01)

(58) Field of Classification Search
None
See application file for complete search history.

(56) References Cited

U.S. PATENT DOCUMENTS

| | | | |
|---|---|---|---|
| 2004/0172684 A1* | 9/2004 | Kovalic | C07H 21/04 800/284 |
| 2009/0089897 A1 | 4/2009 | Abbitt | |
| 2009/0320160 A1* | 12/2009 | Li | C12N 15/11 800/279 |

OTHER PUBLICATIONS

Abbitt et al., Published Applications Database, Publication No. US20150074845A1, SEQ ID No. 18.*
International Search Report and Written Opinion of the International Search Authority for PCT/US2012/047901 dated Oct. 12, 2012.
De Freitas, Fernando A., et al, "Structural Characterization and Promoter Activity Analysis of the gamma-kafirin Gene from Sorghum" Mol Gen Genet (1994) vol. 245: 177-186.
Written Opinion of the International Searching Authority for Application No. PCT/US2012/047901 dated Oct. 12, 2012.
International Preliminary Report on Patentability for Application No. PCT/US2012/047901 dated Feb. 4, 2014.

* cited by examiner

*Primary Examiner* — Phuong T Bui

(57) ABSTRACT

The present invention discloses polynucleotide sequences that can be used to regulate gene expression in plants. Terminator sequences from *Sorghum bicolor* that are functional in plants are disclosed.

17 Claims, 8 Drawing Sheets

Specification includes a Sequence Listing.

```
    CGTGTGTCCAAGAAATGTATCAGTGATACGTATATTCACAATTTTTTAT Majority
                210       220       230       240       250
201 CGTGTGTCCAAGAAATGTATCAGTGATACGTATATTCACAATTTTTTAT SEQ ID 1.seq
200 CGTGTGTCCAAGAAATGTATCAGTGATACGTATATTCACAATTTTTTAT SEQ ID 18.seq GACTTATATACTCACAATTTGTTTTTACTTATACTCXXACAATTTGT   Majority
                260       270       280       290       300
251 GACTTATATACTCACAATTTGTTTTTACTTATACTC--ACAATTTGT   SEQ ID 1.seq
250 GACTTATATACTCACAATTTGTTTTTACTTATACTCGAACAATTTGT   SEQ ID 18.seq TGTGGGTACCATAACAATTTCGATCGAATATATCAGAAAAGTTGACGAA Majority
                310       320       330       340       350
299 TGTGGGTACCATAACAATTTCGATCGAATATATCAGAAAAGTTGACGAA SEQ ID 1.seq
300 TGTGGGTACCATAACAATTTCGATCGAATATATCAGAAAAGTTGACGAA SEQ ID 18.seq
```

FIG. 6C

```
                AGTAAGCTCACTCAAAAAGTTAAATGGGCTGCGGAAGCTGCGTCAGGCCC Majority
                         |         |         |         |         |
                        360       370       380       390       400
            349 AGTAAGCTCACTCAAAAAGTTAAATGGGCTGCGGAAGCTGCGTCAGGCCC SEQ ID 1.seq
            350 AGTAAGCTCACTCAAAAAGTTAAATGGGCTGCGGAAGCTGCGTCAGGCCC SEQ ID 18.seq AAGTTTTGGCTATTCTATCCGGTATCCACGATTTGATGGCTGAGGGACA Majority
                         |         |         |         |         |
                        410       420       430       440       450
            399 AAGTTTTGGCTATTCTATCCGGTATCCACGATTTGATGGCTGAGGGACA SEQ ID 1.seq
            400 AAGTTTTGGCTATTCTATCCGGTATCCACGATTTGATGGCTGAGGGACA SEQ ID 18.seq TATGTTCGXXT                                         Majority
                         |
                        460
            449 TATGTTCGCTT                                         SEQ ID 1.seq
            450 TATGTTCGGCT                                         SEQ ID 18.seq
```

TERMINATOR SEQUENCE FOR GENE EXPRESSION IN PLANTS

CROSS REFERENCE TO RELATED APPLICATIONS

This application is a 371 filing of International Application No. PCT/US12/47901, filed Jul. 23, 2012, now expired, which claims the benefit of U.S. Provisional Application No. 61/514,055, filed Aug. 2, 2011, the entire content of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20141124_BB1984USPCT_AmendedSequenceListing.txt" created on Nov. 24, 2014, and having a size of 140 kilobytes. The sequence listing contained in this ASCII formatted document is part of the specification and is herein incorporated by reference in its entirety.

FIELD OF INVENTION

The present invention relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have protein coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) *EMBO J* 18:241-248; Mette et al (2000) *EMBO J* 19:5194-5201; Mourrain et al (2007) *Planta* 225:365-379, U.S. Pat. Nos. 7,632,982, 7,491,813, 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

Regulatory sequences located downstream of coding regions contain signals required for transcription termination and 3' mRNA processing, and are called terminator sequences. The terminator sequences play a key role in mRNA processing, localization, stability and translation (Proudfoot, N. (2004) *Curr. Op. Cell Biol* 16:272-278; Gilmartin, 2005). The 3' regulatory sequences contained in terminator sequences can affect the level of expression of a gene. Optimal expression of a chimeric gene in plant cells has been found to be dependent on the presence of appropriate 3' sequences (Ingelbrecht, I. L. W. et al (1989) *Plant Cell* 1:671-680). Read through transcription through leaky terminator of a gene can cause unwanted transcription of one transgene from promoter of another one. Also, bidirectional, convergent transcription of transgenes in transgenic plants can occur due to leaky transcription termination of separate convergent genes or from genomic promoters. Convergent, overlapping transcription can decrease transgene expression, or generate antisense RNA (Bieri, S. et al (2002) *Molecular Breeding* 10:107-117). This underlines the importance of discovering novel and efficient transcriptional terminators.

SUMMARY

The present invention relates to regulatory sequences for modulating gene expression in plants. Specifically, the present invention relates to terminator sequences. Recombinant DNA constructs comprising terminator sequences are provided.

An embodiment of this invention is an isolated polynucleotide sequence comprising: (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. Another embodiment of this invention is a recombinant construct comprising an isolated polynucleotide sequence comprising: (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. This recombinant construct may further comprise a promoter and a heterologous polynucleotide, wherein the promoter and the heterologous polynucleotide are operably linked to the isolated polynucleotide sequence.

Another embodiment of this invention is a method of expressing a heterologous polynucleotide in a plant, comprising the steps of (a) introducing into a regenerable plant cell the recombinant DNA construct described above; (b) regenerating a transgenic plant from the regenerable plant cell of (a); and (c) obtaining a progeny plant from the transgenic plant of step (b), wherein the transgenic plant and the progeny plant comprises the recombinant DNA construct and exhibits expression of the heterologous polynucleotide.

In another embodiment, this invention concerns a vector, virus, cell, microorganism, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant or seed comprising the terminator sequences described in the present invention is a monocotyledenous plant or seed. In another embodiment, the plant or seed comprising the terminator sequences described in the present invention is a maize plant or seed.

In another embodiment, any of the methods of expressing a heterologous polynucleotide, wherein the plant cell is a monocotyledonous plant cell, e.g., a maize plant cell.

BRIEF DESCRIPTION OF DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 4A shows GUS reporter gene expression assayed at protein level, and FIG. 4B shows GUS reporter gene expression assayed with qRT-PCR.

Figure 6A:
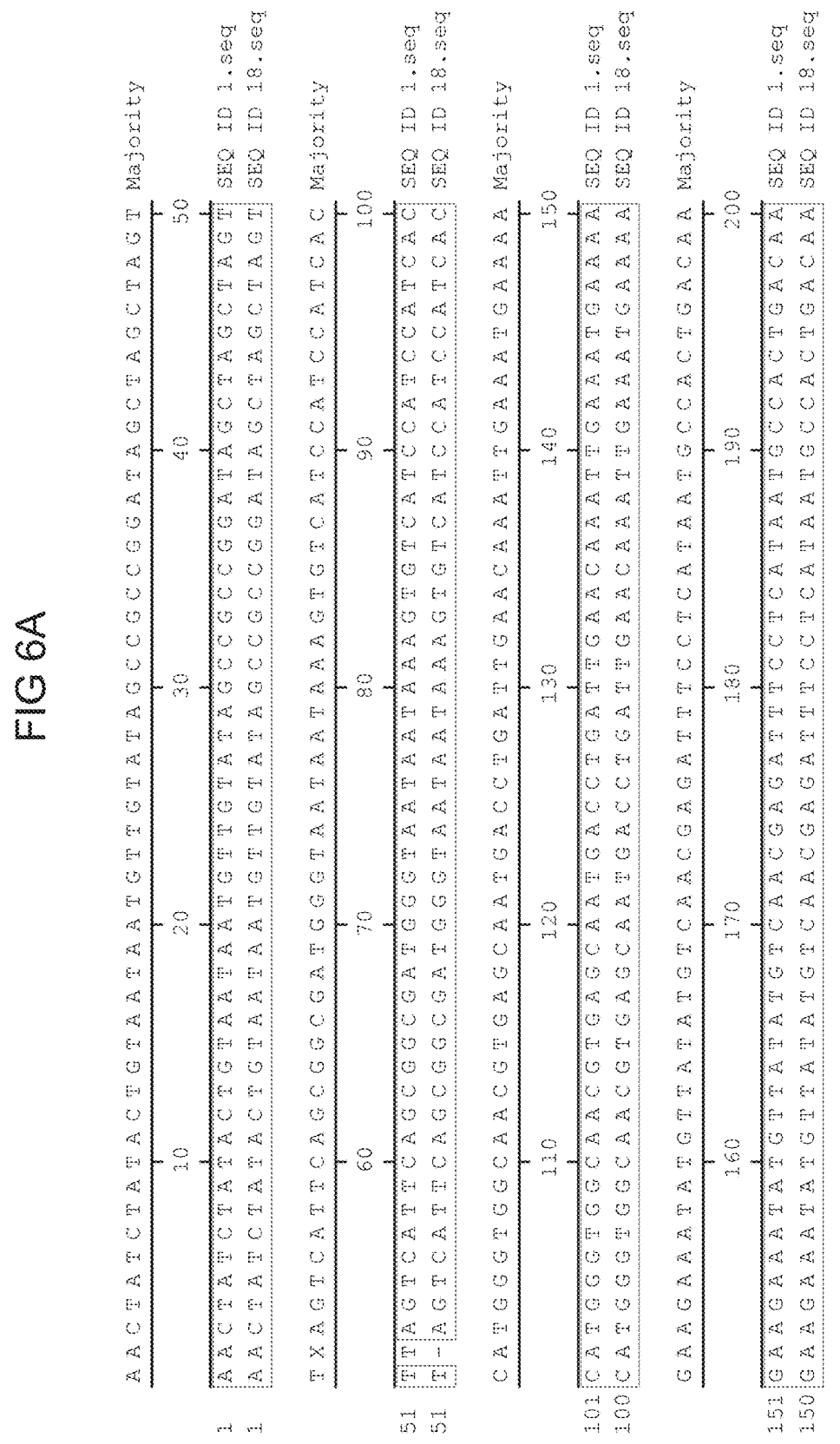

FIG. 6A-6C show the alignment between the cloned SB-GKAF terminator (SEQ ID NO:1) and the nucleotides 1863 to 2322 of NCBI GI NO: 671655 (SEQ ID NO:18). The consensus sequence (SEQ ID NO:19) is show at the top, and the residues that match the consensus exactly are boxed.

Figure 1:
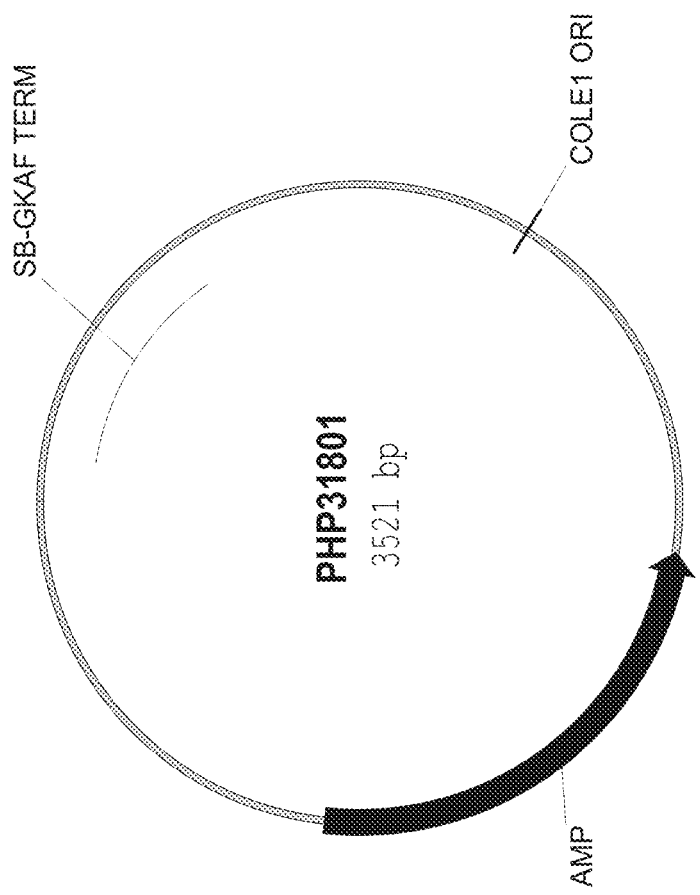
FIG. 1 shows the map of PHP31801, the vector used for cloning SB-GKAF terminator after amplification.

SEQ ID NO:1 is the sequence of the 459 bp SB-GKAF terminator.

SEQ ID NO:2 and 3 are the sequences of the forward and reverse primers used to amplify SB-GKAF terminator.

SEQ ID NO:4 is the nucleotide sequence of PHP31801, the vector used for cloning SB-GKAF terminator after PCR amplification.

SEQ ID NO:5 is the nucleotide sequence of PHP34074, the vector used for testing SB-GKAF terminator.

SEQ ID NO:6 is the nucleotide sequence of PHP34005, the test vector used as a control with PINII terminator.

SEQ ID NOS:7-9 are the sequences of the forward primer, reverse primer and probe used for assessing GUS expression by qRT-PCR in transgenic maize plants, as described in Table 2.

SEQ ID NOS:10-17 are the sequences of the primers used for quantitating read through transcription through SB-GKAF and PINII terminators, by qRT-PCR in transgenic maize plants, as described in Table 3.

SEQ ID NO:18 corresponds to nucleotides 1863 to 2322 of NCBI GI NO: 671655.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within theft genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3° UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques.

"Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press Cold Spring Harbor, 1989 (hereinafter "Sambrook").

"Transcription terminator", "termination sequences", or "terminator" refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

The terms "SB-GKAF terminator", "GKAF terminator" and "gamma-kafirin terminator" are used interchangeably herein, and each refers to the sequence encoding the 3' untranslated region (3' UTR) of the *Sorghum Bicolor* gamma-kafirin gene and about 300 bp of sequence downstream from the 3' UTR. The sequence of the SB-GKAF terminator is given in SEQ ID NO:1. The *Sorghum bicolor* gamma-kafirin gene encodes a gamma-prolamin protein, and the sequence for this gene is given in NCBI GI NO: 671655. Prolamins are the major storage proteins of many cereals. The sorghum gamma-Kafirin, which is the γ-prolamin of sorghum, constitutes about 2-5% of total prolamin in sorghum endosperm, and is composed of a single polypeptide of 27 kDa (de Freitas F A et al (1994) *Mol Gen Genetics* 245(2):177-86).

The present invention encompasses functional fragments and variants of the terminator sequences disclosed herein.

A "functional fragment" of the terminator is defined as any subset of contiguous nucleotides of the terminator sequence disclosed herein, that can perform the same, or substantially similar function as the full length terminator sequence disclosed herein. A "functional fragment" with substantially similar function to the full length terminator disclosed herein refers to a functional fragment that retains the ability to terminate transcription largely at the same level as the full-length terminator sequence. A recombinant construct comprising a heterologous polynucleotide operably linked to a "functional fragment" of the terminator sequence disclosed herein exhibits levels of heterologous polynucleotide expression substantially similar to a corresponding recombinant construct comprising a heterologous polynucleotide operably linked to the full length terminator sequence. A "variant", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments may comprise at least 50, 75, 100, 125, 150, 175, 200, 225, 250, 275, 300, 325, 350, 375, 400, 425 or 450 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

As will be evident to one of skill in the art, any heterologous polynucleotide of interest can be operably linked to the terminator sequences described in the current invention. Examples of polynucleotides of interest that can be operably linked to the terminator sequences described in this invention include, but are not limited to, polynucleotides comprising regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the terminator sequences described in the current invention can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

A recombinant DNA construct (including a suppression DNA construct) of the present invention may comprise at least one regulatory sequence. In an embodiment of the present invention, the regulatory sequences disclosed herein can be operably linked to any other regulatory sequence.

A number of promoters can be used in recombinant DNA constructs of the present invention. The promoters can be selected based on the desired outcome, and may include constitutive, tissue-specific, inducible, or other promoters for expression in the host organism.

The terms "real-time PCR", "quantitative PCR", "quantitative real-time PCR", and "QPCR" are used interchangeably herein, and represent a variation of the standard polymerase chain reaction (FOR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the FOR process. Quantification of amplified product is obtained using fluorescent hydrolysis probes that measure increasing fluorescence for each subsequent PCR cycle. The Ct (cycle threshold) is defined as the number of cycles required for the fluorescent signal to cross the threshold (i.e., exceeds background level). DNA/RNA from genes with higher copy numbers will appear after fewer FOR cycles; so the lower a Ct value, the more copies are present in the specific sample. To quantify RNA. QPCR or real-time FOR is preceded by the step of reverse transcribing mRNA into cDNA. This is referred to herein as "real-time RT-PCR" or "quantitative RT-PCR" or "qRT-PCR".

The Taqman method of FOR product quantification uses a fluorescent reporter probe. This is more accurate since the probe is designed to be sequence-specific and will only bind to the specific FOR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a "housekeeping" gene that is relatively abundant in all cell types, is also performed to allow for comparisons between samples. The amount of DNA/RNA is determined by comparing the results to a standard curve produced by serial dilutions of a known concentration of DNA/RNA.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V (or Clustal W) method of alignment, when compared to SEQ ID NO:1 or SEQ ID NO:18; or (ii) a nucleic acid sequence of at least 90%, 91%, 92%, 93%, 94%, 95%, 96%, 97%, 98%, 99% or 100% sequence identity, based on the Clustal V (or Clustal W) method of alignment, when compared to a functional fragment of SEQ ID NO:1 or SEQ ID NO:18; or (iii) a full complement of the nucleic acid sequence of (i) or (ii), wherein the polynucleotide acts as a terminator in a plant cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASER-GENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Embodiments of the Invention Include:

The present invention relates to terminator sequences. Recombinant DNA constructs comprising terminator sequences are provided.

An embodiment of this invention is an isolated polynucleotide sequence comprising (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. In another aspect, this invention concerns a recombinant DNA construct comprising a promoter, at least one heterologous nucleic acid fragment, and any terminator, or combination of terminator elements, of the present invention, wherein the promoter, at least one heterologous nucleic acid fragment, and terminator(s) are operably linked.

In another embodiment, a functional fragment may comprise at least 450, 425, 400, 375, 350, 325, 300, 275, 250, 225, 200, 175 or 150 contiguous nucleotides of SEQ ID NO:1 or SEQ ID NO:18.

Recombinant DNA constructs can be constructed by operably linking the nucleic acid fragment of the invention, the terminator sequences set forth in SEQ ID NO:1, or 18 or a functional fragment of the nucleotide sequence set forth in SEQ ID NO:1, or 18, to a heterologous nucleic acid fragment.

Another embodiment is a method for transforming a cell (or microorganism) comprising transforming a cell (or microorganism) with any of the isolated polynucleotides or recombinant DNA constructs of the present invention. The cell (or microorganism) transformed by this method is also included. In particular embodiments, the cell is eukaryotic cell, e.g., a yeast, insect or plant cell, or prokaryotic, e.g., a bacterial cell. The microorganism may be Agrobacterium, e.g. Agrobacterium tumefaciens or Agrobacterium rhizogenes.

Another embodiment of this invention is a method of expressing a heterologous polynucleotide in a plant, comprising the steps of introducing into a regenerable plant cell the recombinant DNA construct described above and regenerating a transgenic plant from the transformed regenerable plant cell, wherein the transgenic plant comprises the recombinant DNA construct and exhibits expression of the heterologous polynucleotide.

Another embodiment of this invention is a method of expressing a heterologous polynucleotide in a plant, comprising the steps of introducing into a regenerable plant cell the recombinant DNA construct described above; regenerating a transgenic plant from the regenerable plant cell described above; and obtaining a progeny plant from the transgenic plant, wherein the transgenic plant and the progeny plant comprises the recombinant DNA construct and exhibits expression of the heterologous polynucleotide.

In another embodiment, any of the methods of expressing a heterologous polynucleotide, wherein the plant cell is a monocotyledonous or dicotyledonous plant cell, for example, a maize or soybean plant cell. The plant cell may also be from sunflower, sorghum, canola, wheat, alfalfa, cotton, rice, barley, millet, sugar cane or switchgrass.

In another embodiment, this invention concerns a vector, virus, cell, microorganism, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant (or seed derived from the plant) comprising the terminator sequences described in the present invention is a monocotyledonous or dicotyledonous plant, for example, a maize or soybean plant. The plant may also be sunflower, sorghum, canola, wheat, alfalfa, cotton, rice, barley, millet, sugar cane or switchgrass. The plant may be an inbred plant or a hybrid plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Amplification and Cloning of a Sorghum Bicolor Gamma-Kafirin Terminator Sequence Primers (SEC) ID NOS:2 and 3) were designed for amplifying the terminator of gamma-Kafirin gene from Sorghum bicolor (SB-GKAF) based on the Sorghum bicolor genomic sequence database. The primer sequences are given below, the underlined region is not homologous with genomic template:

```
TMS2039
(forward primer; SEQ ID NO: 2):
CAGATCTGATATCGATGGGCCCACTAACTATCTATACTG
TAATAATGTTGTATAG TMS2040
(reverse primer; SEQ ID NO: 3):
CGGACCGGGTGACCAAGCTTAAGCGAACATATGTCCCTC
```

Figure 2:
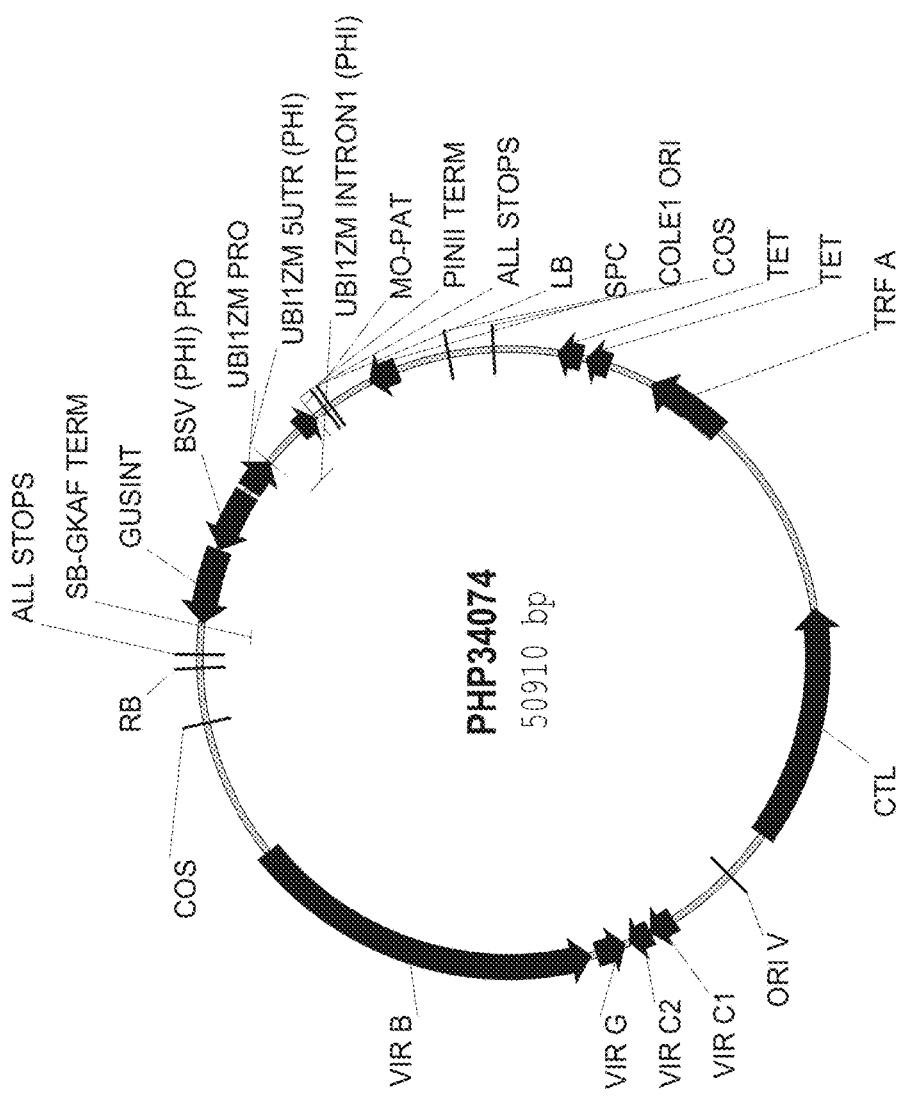
FIG. 2 shows the map of PHP34074, the vector used for testing the SB-GKAF terminator.

A 504 bp product comprising the 465 bp SB-GKAF terminator sequence (SEQ ID NO:1) was amplified by PCR using these primers. The product was cloned into pGEMTeasy (Promega) (PHP31801; FIG. 1; SEQ ID NO:4) and the sequence was confirmed. The cloned SB-GKAF terminator included 165 bp of the predicted 3' UTR of SB-GKAF along with about 300 bp of downstream sequence. The amplified sequence of SB-GKAF terminator (SEQ ID NO:1) was then cloned into an Agrobacterium transformation vector (PHP34074; FIG. 2; SEQ ID NO:5), which had the following expression cassettes in divergent orientation:
SB-GKAF TERMINATOR:GUSINT:BSV PRO and
UBI-PRO:UBI INTRON:MOPAT:PINII TERM.

BSV PRO is Banana Streak Virus promoter, which is a strong constitutive promoter. A construct with a potato PINII terminator (Keil at al. (1986) Nucleic Acids Res. 14:5641-5650) in place of the SB-GKAF terminator was used as a control (PHP34005; SEQ ID NO:6).

Example 2

Transient Transformation to Test Efficacy of a SB-GKAF Terminator

Figure 3:
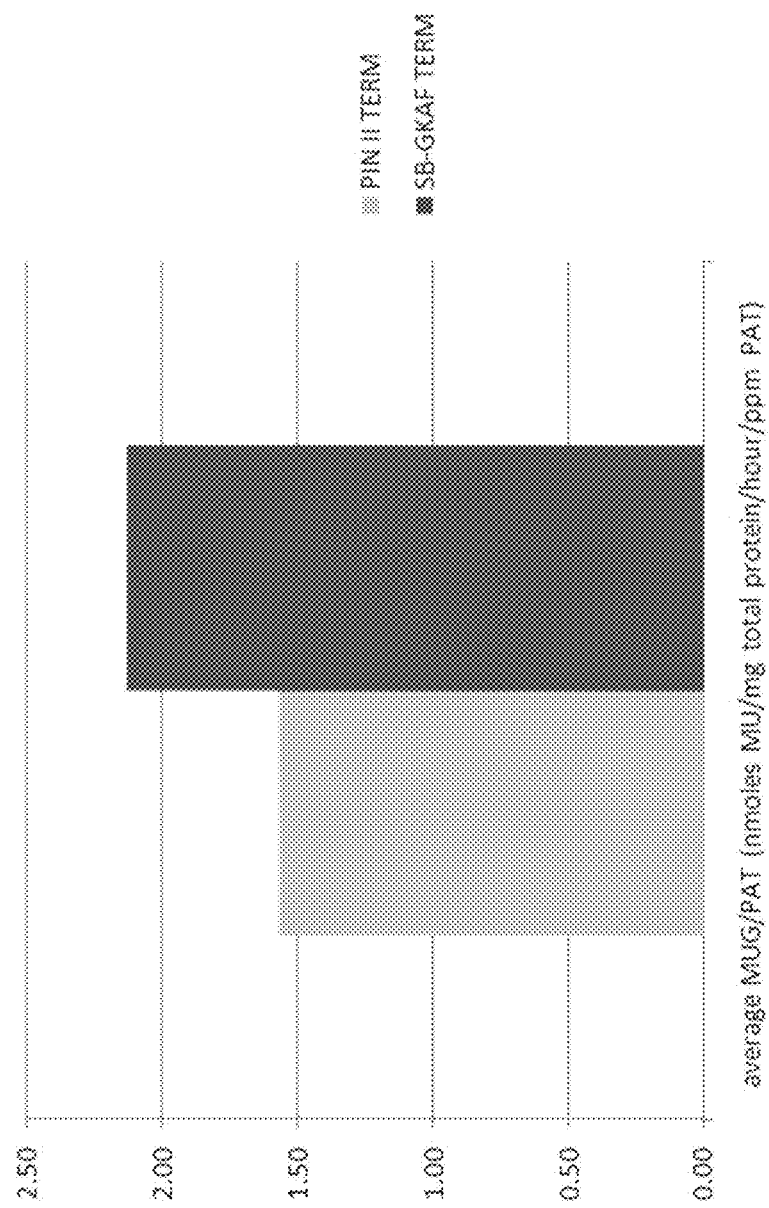
FIG. 3 shows the results of testing SB-GKAF terminator compared to PINII terminator in transient assays. It shows quantitative analysis of GUS reporter gene expression in BMS cells transformed with PHP34074 (SB-GKAF terminator) and PHP34005 (FINN terminator).

The isolated SB-GKAF terminator sequence (SEQ ID NO:1) was tested for its ability to act efficiently as a terminator in a recombinant construct. Its efficacy as a terminator was tested by its ability to stop transcription and by its ability to increase expression of a protein. Since improper termination can lead to improper processing of the 3' end of mRNA, and hence affect RNA stability, terminators have been found to affect protein expression levels. It has been shown that different terminators can cause up to 100-fold variation in the efficiency of transgene expression (Bieri et al, (2002) Molecular Breeding 10: 107-117; An at al (1989) Plant Cell 1: 115-122; Ingelbrecht et al (1989), Plant Cell, 1:671-680; Ali and Taylor (2001) Plant Mol. Bio., 46:251-261). Hence we tested the SB-GKAF sequence (SEQ ID NO:1) for its ability to increase expression of a protein compared to the well-known PINII terminator. The Agrobacterium transformation vectors PHP34074 (SEQ ID NO:5) and PHP34005 (SEQ ID NO:6) described in Example 1 were used for transient transformation of BMS (Black Mexican Sweet) cells. The cells were harvested 5 days after transformation and sent for a quantification of the GUS activity (MUG assay). The SB-GKAF construct (PHP34074; SEQ ID NO:5) had ~35% more expression than that of the PINII construct (PHP34005, SEQ ID NO:6) when the GUS expression was normalized to the MOPAT expression (FIG. 3; Table 1). This information was indicative of the ability of the isolated SB-GKAF sequence (SEQ ID NO:1) to act efficiently as a terminator, by allowing protein expression equal to or above that of the PINII terminator.

TABLE 1

| Construct | Sequence Tested | Average MUG/PAT* | Standard Deviation |
|---|---|---|---|
| BSV PRO:GUSINT: PINII TERM | PIN II TERM | 1.57 | 0.17 |
| BSV PRO:GUSINT: SB-GKAF TERM | SB-GKAF TERM | 2.13 | 0.41 |

*Measured as: nmoles MU/mg total protein/hour/ppm PAT

Example 3

Stable Transformation Assays to Test SB-GKAF Terminator Activity

The Agrobacterium transformation vectors PHP34074 (SEQ ID NO:5) and PHP34005 (SEQ ID NO:6) described in Example 1, that were used for transient transformation assays as described in Example 2, were also used in Gaspe-Flint derived maize lines for stable transformation to generate transgenic maize plants.

Quantitative Reverse Transcriptase-PCR (qRT-PCR) and GUS assays were done from stably transformed plant tissues to test the ability of isolated SB-GKAF terminator sequence (SEQ ID NO:1) to stop transcription (that is prevent transcription read-through transcription) and to compare GUS expression as compared to that with PINII terminator.

GUS Expression Analysis:

The expression of the GUS gene in the transgenic plants was assessed at the protein as well as transcript levels. To assess the expression at the protein level, MUG assay was performed on seedling leaf material. To assess the expression at the transcript level, qRT-PCR was done using primers shown in Table 2.

TABLE 2

| Primer/ Probe | Type | Sequence | Fluor | qPCR Assay |
|---|---|---|---|---|
| GUS-1482F | Forward | SEQ ID NO: 7 | — | Taqman |
| GUS-1553R | Reverse | SEQ ID NO: 8 | — | Taqman |

TABLE 2-continued

| Primer/Probe | Type | Sequence | Fluor | qPCR Assay |
| --- | --- | --- | --- | --- |
| GUS-1509P | Probe | SEQ ID NO: 9 | FAM | Taqman |

Figure 4A:
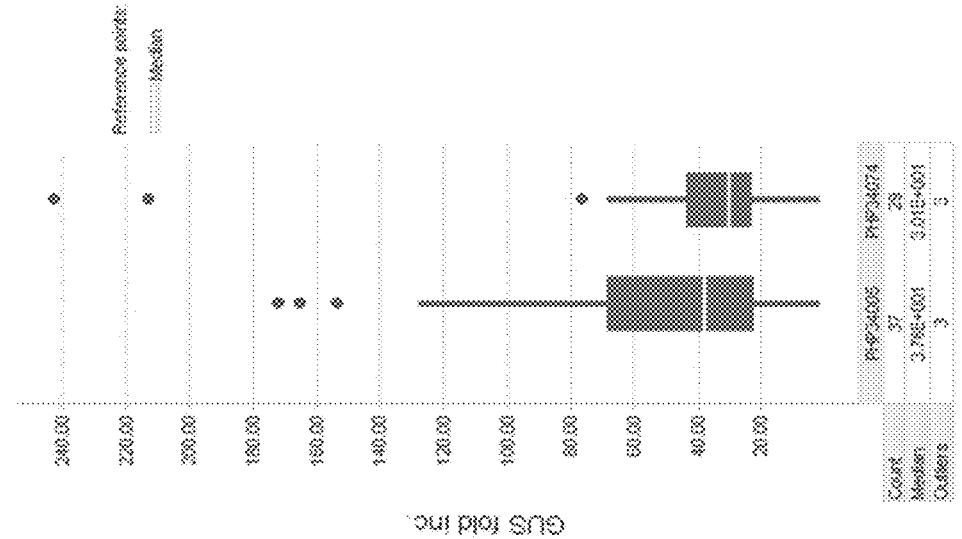
FIG. 4A and FIG. 4B show quantitative analysis of GUS reporter gene expression in Gaspe Flint derived maize lines stably transformed with SB-GKAF (PHP34074) and PINII (PHP34005) terminator constructs.
Figure 4B:
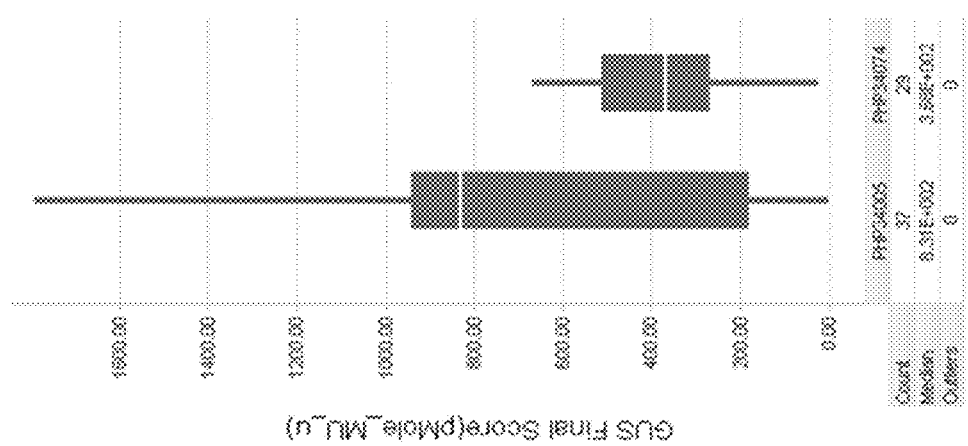

Plants were grown in the greenhouse and leaves were sampled at the R1 stage of development for expression analysis. Multiple plants were tested for each construct. Each plant was analyzed for expression of the GUS gene. GUS gene with the SB-GKAF terminator had GUS expression in the same range as that of PINII terminator at both the protein (FIG. 4A) and transcript (FIG. 4B) level.

Quantitative Reverse Transcriptase PCR (qRT-PCR) to Determine Read-Through Transcription Through the SB-GKAF Terminator:

The qRT-PCR assays were performed with leaf tissue from the stable transformants generated using PHP34074 and PHP34005. Each plant was tested for the presence of a read-through transcript that had passed through the PINII terminator and the SB-GKAF terminator (SEQ ID NO:1). To assess presence of products that would indicate that transcription was continuing past the terminator, amplification was targeted downstream of the terminator being tested. Two primer sets were designed downstream of the tested terminators.

Primer set Term1~100 nt from the terminator
Primer set Term2.1~500 nt from the terminator Multiple plants were tested for each construct. The primers are shown in Table 3.

TABLE 3

| Primer/Probe | Name | Type | Sequence | Fluor | qPCR Assay |
| --- | --- | --- | --- | --- | --- |
| Term2.1[1] | Term2.1F | fwd | SEQ ID NO: 10 | — | SYBR |
| Term2.1[1] | Term2.1R | rev | SEQ ID NO: 11 | — | SYBR |
| Term1[1] | Term 1F | fwd | SEQ ID NO: 12 | — | Taqman |
| Term1[1] | Term 1R | rev | SEQ ID NO: 13 | — | Taqman |
| Term1[1] | Term_1P | probe | SEQ ID NO: 14 | FAM | Taqman |
| Actin[2] | Actin_MGB_F | fwd | SEQ ID NO: 15 | — | Taqman |
| Actin[2] | Actin_MGB_R | rev | SEQ ID NO: 16 | — | Taqman |
| Actin[2] | Actin_VIC_P | probe | SEQ ID NO: 17 | VIC | Taqman |

[1]Post-Terminator Primer Set
[2]Reference Gene

The test plants were classified into 3 categories depending on the qRT-PCR results:

1. Plants showing complete termination: where all GUS transcripts are completely terminated before they reached the specific primer set location;
2. Plants showing a high degree of termination: where a large portion of the GUS transcripts are terminated before they reached the specific primer set location, also defined as:
    Primer set Term1—$\Delta CT>13$
    Primer set Term2.1—$\Delta CT>9$; and
3. Plants showing poor termination.

Figure 5:
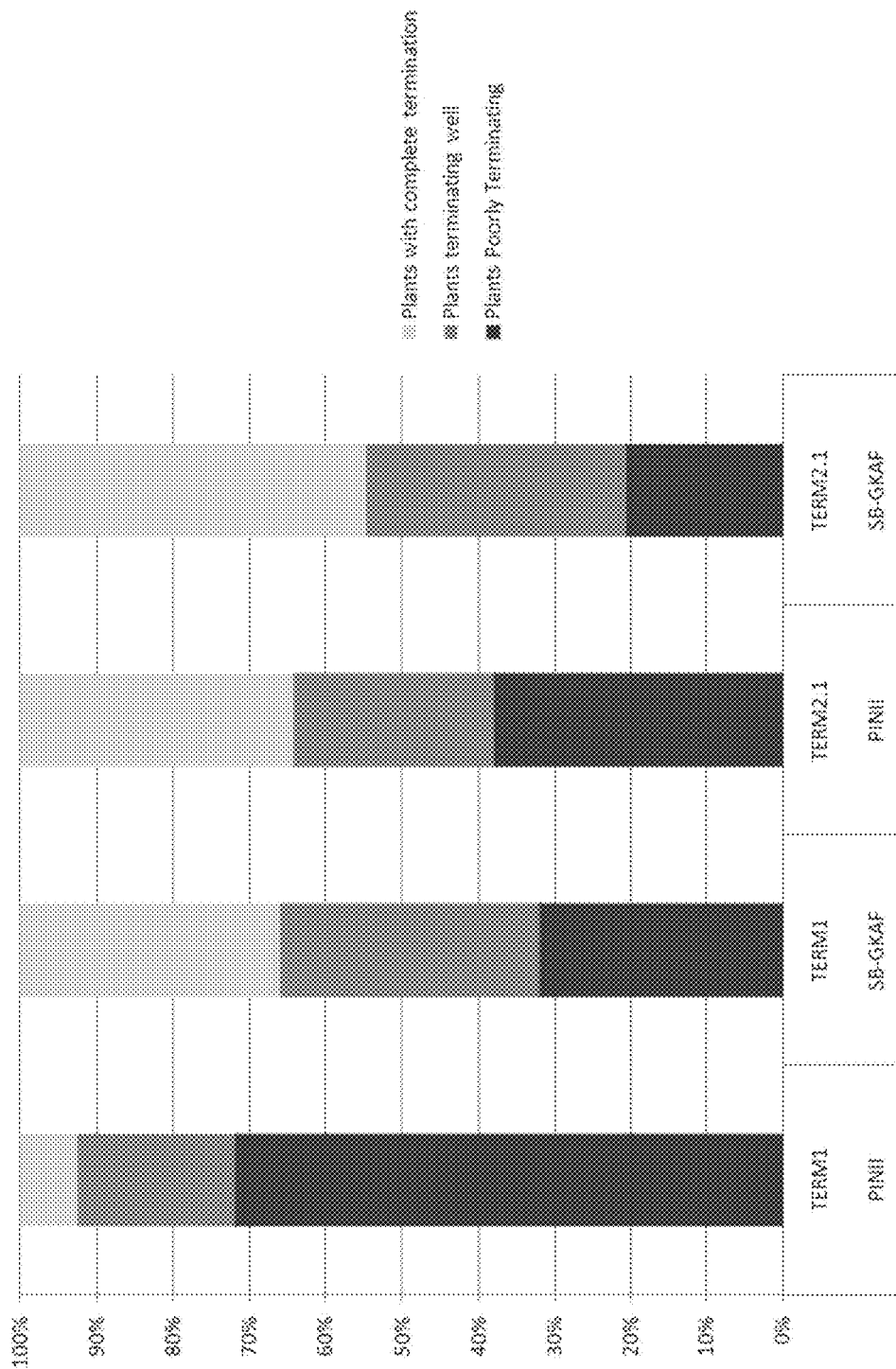
FIG. 5 shows the results of qRT-PCR assays with stably transformed Gaspe Hint derived maize lines, using two sets of primers downstream of the SB-GKAF terminator and the PINII terminator.

As can be see from FIG. 5, the SB-GKAF terminator proved to have fewer "poorly terminating" plants than the PINII terminator (FIG. 5). Thus the qRT-PCR score for presence of transcripts that had proceeded through the terminator was lower for the SB-GKAF terminator than that for the PINII terminator.

We claim:

1. A recombinant construct comprising a polynucleotide sequence operably linked to a heterologous polynucleotide sequence, wherein the polynucleotide sequence comprises:
   (a) a nucleotide sequence comprising the sequence set forth in SEQ ID NO:1; or
   (b) a fragment of at least 200 contiguous nucleotides of (a) having terminator activity;
wherein the polynucleotide sequence functions as a transcriptional terminator in a plant cell.

2. The recombinant construct of claim 1 wherein the heterologous polynucleotide sequence is operably linked to a promoter.

3. A plant comprising the recombinant construct of claim 1.

4. The plant of claim 3 wherein the plant is a monocot.

5. The plant of claim 4 wherein the plant is a maize plant.

6. A seed comprising the recombinant construct of claim 1.

7. The seed of claim 6 wherein the seed is from a monocot plant.

8. The seed of claim 7 wherein the seed is from a maize plant.

9. A method of expressing a heterologous polynucleotide in a plant, comprising the steps of:

(a) introducing into a regenerable plant cell the recombinant construct of claim 2;
(b) regenerating a transgenic plant from the regenerable plant cell of step (a), wherein the transgenic plant comprises the recombinant construct of claim 2; and
(c) obtaining a progeny plant from the transgenic plant of step (b), wherein the progeny plant comprises the recombinant construct of claim 2 and exhibits expression of the heterologous polynucleotide.

10. The method of claim 9, wherein the plant is a monocot plant.

11. The method of claim 10, wherein the plant is a maize plant.

12. A plant comprising the recombinant construct of claim 2.

13. The plant of claim 12 wherein the plant is a monocot.

14. The plant of claim 13 wherein the plant is a maize plant.

15. A seed comprising the recombinant construct of claim 2.

16. The seed of claim 15 wherein the seed is from a monocot plant.

17. The seed of claim 16 wherein the seed is from a maize plant.

* * * * *

SEQUENCE LISTING

```
<160> NUMBER OF SEQ ID NOS: 19

<210> SEQ ID NO 1
<211> LENGTH: 459
<212> TYPE: DNA
<213> ORGANISM: Sorghum bicolor

<400> SEQUENCE: 1
aactatctat actgtaataa tgttgtatag ccgccggata gctagctagt ttagtcattc      60
agcggcgatg ggtaataata aagtgtcatc catccatcac catgggtggc aacgtgagca     120
atgacctgat tgaacaaatt gaaatgaaaa gaagaaatat gttatatgtc aacgagattt     180
cctcataatg ccactgacaa cgtgtgtcca agaaatgtat cagtgatacg tatattcaca     240
atttttttat gacttatact cacaatttgt ttttttacta cttatactca caatttgttg     300
tgggtaccat aacaatttcg atcgaatata tatcagaaag ttgacgaaag taagctcact     360
caaaaagtta aatgggctgc ggaagctgcg tcaggcccaa gttttggcta ttctatccgg     420
tatccacgat tttgatggct gagggacata tgttcgctt                            459

<210> SEQ ID NO 2
<211> LENGTH: 55
<212> TYPE: DNA
<213> ORGANISM: Artificial Sequence
<220> FEATURE:
<223> OTHER INFORMATION: forward primer

<400> SEQUENCE: 2
cagatctgat atcgatgggc ccactaacta tctatactgt aataatgttg tatag           55
```

<210> SEQ ID NO 3
<211> LENGTH: 39
<212> TYPE: DNA
<213> ORGANISM: Artificial Sequence
<220> FEATURE:
<223> OTHER INFORMATION: Reverse primer

<400> SEQUENCE: 3

```
cggaccgggt gaccaagctt aagcgaacat atgtccctc                    39
```

<210> SEQ ID NO 4
<211> LENGTH: 3521
<212> TYPE: DNA
<213> ORGANISM: Artificial Sequence
<220> FEATURE:
<223> OTHER INFORMATION: Vector

<400> SEQUENCE: 4

```
gggcgaattg ggcccgacgt cgcatgctcc cggccgccat ggcggccgcg ggaattcgat     60
tcggaccggg tgaccaagct taagcgaaca tatgtccctc agccatcaaa atcgtggata    120
ccggatagaa tagccaaaac ttgggcctga cgcagcttcc gcagcccatt taactttttg    180
agtgagctta ctttcgtcaa ctttctgata tatattcgat cgaaattgtt atggtaccca    240
caacaaattg tgagtataag tagtaaaaaa acaaattgtg agtataagtc ataaaaaaat    300
tgtgaatata cgtatcactg atacatttct tggacacacg tcgtcagtgg cattatgagg    360
aaatctcgtt gacatataac atatttcttc ttttcatttc aatttgttca atcaggtcat    420
tgctcacgtt gccacccatg gtgatggatg gatgacactt tattattacc catcgccgct    480
gaatgactaa actagctagc tatccggcgg ctatacaaca ttattacagt atagatagtt    540
agtgggccca tcgatatcag atctgaatca ctagtgaatt cgcggccgcc tgcaggtcga    600
ccatatggga gagctcccaa cgcgttggat gcatagcttg agtattctat agtgtcacct    660
aaatagcttg gcgtaatcat ggtcatagct gtttcctgtg tgaaattgtt atccgctcac    720
aattccacac aacatacgag ccggaagcat aaagtgtaaa gcctggggtg cctaatgagt    780
gagctaactc acattaattg cgttgcgctc actgcccgct ttccagtcgg gaaacctgtc    840
gtgccagctg cattaatgaa tcggccaacg cgcggggaga ggcggtttgc gtattgggcg    900
ctcttccgct tcctcgctca ctgactcgct gcgctcggtc gttcggctgc ggcgagcggt    960
atcagctcac tcaaaggcgg taatacggtt atccacagaa tcaggggata acgcaggaaa   1020
gaacatgtga gcaaaaggcc agcaaaaggc caggaaccgt aaaaaggccg cgttgctggc   1080
gtttttccat aggctccgcc cccctgacga gcatcacaaa aatcgacgct caagtcagag   1140
gtggcgaaac ccgacaggac tataaagata ccaggcgttt ccccctggaa gctccctcgt   1200
gcgctctcct gttccgaccc tgccgcttac cggatacctg tccgcctttc tcccttcggg   1260
aagcgtggcg ctttctcata gctcacgctg taggtatctc agttcggtgt aggtcgttcg   1320
ctccaagctg ggctgtgtgc acgaaccccc cgttcagccc gaccgctgcg ccttatccgg   1380
taactatcgt cttgagtcca acccggtaag acacgactta tcgccactgg cagcagccac   1440
tggtaacagg attagcagag cgaggtatgt aggcggtgct acagagttct tgaagtggtg   1500
gcctaactac ggctacacta agaacagt atttggtatc tgcgctctgc tgaagccagt    1560
taccttcgga aaagagttg gtagctcttg atccggcaaa caaaccaccg ctggtagcgg   1620
tggttttttt gtttgcaagc agcagattac gcgcagaaaa aaggatctc aagaagatcc    1680 tttgatcttt tctacggggt ctgacgctca gtggaacgaa aactcacgtt aagggatttt   1740
```

```
ggtcatgaga ttatcaaaaa ggatcttcac ctagatcctt ttaaattaaa aatgaagttt    1800
taaatcaatc taaagtatat atgagtaaac ttggtctgac agttaccaat gcttaatcag    1860
tgaggcacct atctcagcga tctgtctatt tcgttcatcc atagttgcct gactccccgt    1920
cgtgtagata actacgatac gggagggctt accatctggc cccagtgctg caatgatacc    1980
gcgagaccca cgctcaccgg ctccagattt atcagcaata aaccagccag ccggaagggc    2040
cgagcgcaga gtggtcctg caactttatc cgcctccatc cagtctatta attgttgccg     2100
ggaagctaga gtaagtagtt cgccagttaa tagtttgcgc aacgttgttg ccattgctac    2160
aggcatcgtg gtgtcacgct cgtcgtttgg tatggcttca ttcagctccg gttcccaacg    2220
atcaaggcga gttacatgat cccccatgtt gtgcaaaaaa gcggttagct ccttcggtcc    2280
tccgatcgtt gtcagaagta agttggccgc agtgttatca ctcatggtta tggcagcact    2340
gcataattct cttactgtca tgccatccgt aagatgcttt tctgtgactg gtgagtactc    2400
aaccaagtca ttctgagaat agtgtatgcg cgaccgagt tgctcttgcc cggcgtcaat     2460
acgggataat accgcgccac atagcagaac tttaaaagtg ctcatcattg gaaaacgttc    2520
ttcggggcga aaactctcaa ggatcttacc gctgttgaga tccagttcga tgtaacccac    2580
tcgtgcaccc aactgatctt cagcatcttt tactttcacc agcgtttctg ggtgagcaaa    2640
aacaggaagg caaaatgccg caaaaaaggg aataagggcg acacggaaat gttgaatact    2700
catactcttc ctttttcaat attattgaag catttatcag ggttattgtc tcatgagcgg    2760
atacatattt gaatgtattt agaaaaataa acaatagggg ttccgcgcac atttccccg    2820
aaaagtgcca cctgatgcgg tgtgaaatac cgcacagatg cgtaaggaga aaataccgca    2880
tcaggaaatt gtaagcgtta atattttgtt aaaattcgcg ttaaattttt gttaaatcag    2940
ctcattttt aaccaatagg ccgaaatcgg caaaatccct tataaatcaa agaatagac     3000
cgagatagg ttgagtgttg ttccagtttg gaacaagagt ccactattaa agaacgtgga    3060
ctccaacgtc aaagggcgaa aaaccgtcta tcagggcgat ggcccactac gtgaaccatc    3120
accctaatca gttttttgg ggtcgaggtg ccgtaaagca ctaaatcgga acctaaagg     3180
gagcccccga tttagagctt gacggggaaa gccggcgaac gtggcgagaa aggaagggaa    3240
gaaagcgaaa ggagcgggcg ctagggcgct ggcaagtgta gcggtcacgc tgcgcgtaac    3300
caccacaccc gccgcgctta atgcgccgct acagggcgcg tccattcgcc attcaggctg    3360
cgcaactgtt gggaagggcg atcggtgcgg gcctcttcgc tattacgcca gctggcgaaa    3420
gggggatgtg ctgcaaggcg attaagttgg gtaacgccag ggttttccca gtcacgacgt    3480
tgtaaaacga cggccagtga attgtaatac gactcactat a                       3521
```

<210> SEQ ID NO 5
<211> LENGTH: 50910
<212> TYPE: DNA
<213> ORGANISM: Artificial Sequence
<220> FEATURE:
<223> OTHER INFORMATION: SB-GKAF terminator construct

<400> SEQUENCE: 5

```
acgtgaccct agtcacttag gttaccagag ctggtcacct ttgtccacca agatggaact      60
gcggccgctc attaattaag tcaggcgcgc ctctagttga agacacgttc atgtcttcat     120
cgtaagaaga cactcagtag tcttcggcca gaatggccat ctggattcag caggcctaga    180
aggccattta aatcctgagg atctggtctt cctaaggacc cggatatcg ctatcaactt     240
tgtatagaaa agttgggccg aattcgagct cggtacggcc agaatggccc ggaccgggtt    300
```

```
accgaattcg agctcggtac cactagtaag cttaagcgaa catatgtccc tcagccatca      360
aaatcgtgga taccggatag aatagccaaa acttgggcct gacgcagctt ccgcagccca      420
tttaactttt tgagtgagct tactttcgtc aactttctga tatatattcg atcgaaattg      480
ttatggtacc cacaacaaat tgtgagtata agtagtaaaa aaacaaattg tgagtataag      540
tcataaaaaa attgtgaata tacgtatcac tgatacattt cttggacaca cgtcgtcagt      600
ggcattatga ggaaatctcg ttgacatata acatatttct tcttttcatt tcaatttgtt      660
caatcaggtc attgctcacg ttgccaccca tggtgatgga tggatgacac tttattatta      720
cccatcgccg ctgaatgact aaactagcta gctatccggc ggctatacaa cattattaca      780
gtatagatag ttagtgggcc catcgatatc agatcttcat tgtttgcctc cctgctgcgg      840
tttttcaccg aagttcatgc cagtccagcg ttttttgcagc agaaaagccg ccgacttcgg      900
tttgcggtcg cgagtgaaga tcccttctt gttaccgcca acgcgcaata tgccttgcga      960
ggtcgcaaaa tcggcgaaat tccatacctg ttcaccgacg acggcgctga cgcgatcaaa     1020
gacgcggtga tacatatcca gccatgcaca ctgatactct tcactccaca tgtcggtgta     1080
cattgagtgc agcccggcta acgtatccac gccgtattcg gtgatgataa tcggctgatg     1140
cagtttctcc tgccaggcca gaagttcttt ttccagtacc ttctctgccg tttccaaatc     1200
gccgctttgg acataccatc cgtaataacg gttcaggcac agcacatcaa agagatcgct     1260
aatggtatcg gtgtgagcgt cgcagaacat tacattgacg caggtgatcg gacgcgtcgg     1320
gtcgagttta cgcgttgctt ccgccagtgg cgcgaaatat tcccgtgcac cttgcggacg     1380
ggtatccggt tcgttggcaa tactccacat caccacgctt gggtggtttt tgtcacgcgc     1440
tatcagctct ttaatcgcct gtaagtgcgc ttgctgagtt tccccgttga ctgcctcttc     1500
gctgtacagt tcttttcggct tgttgcccgc ttcgaaacca atccctaaag agaggttaaa     1560
gccgacagca gcagtttcat caatcaccac gatgccatgt tcatctgccc agtcgagcat     1620
ctcttcagcg taagggtaat gcgaggtacg gtaggagttg gccccaatcc agtccattaa     1680
tgcgtggtcg tgcaccatca gcacgttatc gaatcctttg ccacgcaagt ccgcatcttc     1740
atgacgacca aagccagtaa agtagaacgg tttgtggtta atcaggaact gttggccctt     1800
cactgccact gaccggatgc cgacgcgaag cgggtagata tcacactctg tctggctttt     1860
ggctgtgacg cacagttcat agagataacc ttcacccggt tgccagaggt gcggattcac     1920
cacttgcaaa gtcccgctag tgccttgtcc agttgcaacc acctgttgat ccgcatcacg     1980
cagttcaacg ctgacatcac cattggccac cacctgccag tcaacagacg cgtggttaca     2040
gtcttgcgcg acatgcgtca ccacggtgat atcgtccacc caggtgttcg gcgtggtgta     2100
gagcattacg ctgcgatgga ttccggcata gttaaagaaa tcatggaagt aagactgctt     2160
tttcttgccg ttttcgtcgg taatcaccat tcccggcggg atagtctgcc agttcagttc     2220
gttgttcaca caaacggtga tacctgcaca tcaacaaatt ttggtcatat attagaaaag     2280
ttataaatta aaatatacac acttataaac tacagaaaag caattgctat atactacatt     2340
cttttatttt gaaaaaaata tttgaaatat tatattacta ctaattaatg ataattatta     2400
tatatatatc aaaggtagaa gcagaaactt acgtacactt ttcccggcaa taacatacgg     2460
cgtgacatcg gcttcaaatg gcgtatagcc gccctgatgc tccatcactt cctgattatt     2520
gacccacact ttgccgtaat gagtgaccgc atcgaaacgc agcacgatac gctggcctgc     2580
ccaacctttc ggtataaaga cttcgcgctg ataccagacg ttgcccgcat aattacgaat     2640
```

```
atctgcatcg gcgaactgat cgttaaaact gcctggcaca gcaattgccc ggctttcttg    2700
taacgcgctt tcccaccaac gctgatcaat tccacagttt tcgcgatcca gactgaatgc    2760
ccacaggccg tcgagttttt tgatttcacg ggttggggtt tctacaggac ggaccatggt    2820
gtcgtgtgga tccaaattgt atgcaaggtg aatgactttc ttttcgtaaa ctagatagga    2880
gtactcctcc aggatgctta acccgtattg acgtacagag gtctatgatc cttttgttta    2940
taaaggagct tgtagttcag tcagtcttat acttcacgat gcccatgttt ctatatagga    3000
tattatcttg gctttgtaag tacttcacgc aggttatgtt ctgtttctag gatattatcc    3060
tcatacatgc gaagaaccaa tttttcccccc attctcttcg ggtacttttt cttgggtagg    3120
catgctctct tggaccaact agcataaaac ataatcattt ttccctacag ccttgaccag    3180
ctataatcga aatcatgctc atttttctaa gaaagactga atacagctcc aatttaaaca    3240
atttaaatca taaacttgta actcaattag agaaaagcag agcccttcgg ctcctatcta    3300
aaggaattac cccatgaaag ccataaaaac gaaccttgct ctgataccag acgggtctac    3360
gctcgcggaa ctaggatctt gcgctctact cgcacaaagt gaactcgcac aaagtgtgtt    3420
tcaagcacag aagtttttat ttctcaaatc aggagtaaac tcgcgttgtg gtgcgtgttt    3480
gcaacctgaa tacaaggctc cttatataga gagttgtgga gctttctggc atcgttaggt    3540
ggcatccacc aataatgcag ataagcatca tcacatgtct ctggcctaac aactttgcgt    3600
aagaatcctg caaagttact aaaggtcatc gtgcgtgact agacaacgca caccgacaaa    3660
cttaaaataa agagacatta actttgtct cctcttttaca taaagtgagt ggtatccagc    3720
tcactccgca tcttatcagt cttcacaccg gttggtatca acacgtgta ggggtccgcc    3780 acttccgctt cagtcatcat tactgatatc cagcagatct agagcatctt caataagata    3840
ttcttgttct gcacgcagat tttcttgctc cctcagtaat tcctcccaca gtgagtcttc    3900
tgatatttct tcaagtttct tctcccatct gatcttttcc tgcacaaacg agtcaatttg    3960
gtctttccag acccaagtaa aacaagtgtt agtttcacag gagtaaaact ccctgtcagg    4020
atttctggat gttctggaga tcttcagttt tgctggttta ttgcatccac atttgaaaac    4080
cggctcttca cttagtgtta gcacattgat ttgatgcaac ctgtagcctt tgctcaacca    4140
gtcttcatat cttttttacaa catcattaac tctctgtttt gcatcggtgt ttcccttgtg    4200
aaatacctcc tccactgcat tgatcaacac accttcagat tgatgctttt ccggatggag    4260
aataatcttt accagtcttg acagagtgtc tgctaaaacg ttgtcctttc cgtcaatgtg    4320
ttcaaactta atctcaagac ctgtcccggt aatgtaatct gtgaaggcaa gccatctgac    4380
tcttgatggt ttatgatcac tgcttttctt gtaaaagctc actattgctt gactgtcagt    4440
tctgattatg agctctttgt aagcttggtc accoggtccg ggcctagaag gccagcttcg    4500
gccgccccgg gcaactttat tatacaaagt tgatagatat cggaccgatt aaactttaat    4560
tcggtccgaa gcttgcatgc ctgcagtgca gcgtgacccg gtcgtgcccc tctctagaga    4620
taatgagcat tgcatgtcta agttataaaa aattaccaca tatttttttt gtcacacttg    4680
tttgaagtgc agtttatcta tctttataca tatatttaaa ctttactcta cgaataatat    4740
aatctatagt actacaataa tatcagtgtt ttagagaatc atataaatga acagttagac    4800
atggtctaaa ggacaattga gtattttgac aacaggactc tacagtttta tcttttttagt    4860 gtgcatgtgt tctccttttt ttttgcaaat agcttcacct atataatact tcatccattt    4920
tattagtaca tccattagg gtttagggtt aatggttttt atagactaat ttttttagta    4980
catctatttt attctatttt agcctctaaa ttaagaaaac taaaactcta ttttagtttt    5040
```

```
tttatttaat aatttagata taaaatagaa taaaataaag tgactaaaaa ttaaacaaat    5100 acccttttaag aaattaaaaa aactaaggaa acatttttct tgtttcgagt agataatgcc    5160
agcctgttaa acgccgtcga cgagtctaac ggacaccaac cagcgaacca gcagcgtcgc    5220
gtcgggccaa gcgaagcaga cggcacggca tctctgtcgc tgcctctgga ccctctcga    5280 gagttccgct ccaccgttgg acttgctccg ctgtcggcat ccagaaattg cgtggcggag    5340
cggcagacgt gagccggcac ggcaggcggc ctcctcctcc tctcacggca ccggcagcta    5400
cgggggattc ctttcccacc gctccttcgc tttcccttcc tcgcccgccg taataaatag    5460
acaccccctc cacaccctct ttccccaacc tcgtgttgtt cggagcgcac acacacacaa    5520
ccagatctcc cccaaatcca cccgtcggca cctccgcttc aaggtacgcc gctcgtcctc    5580
cccccccccc ctctctacct tctctagatc ggcgttccgg tccatgcatg ttagggccc    5640 ggtagttcta cttctgttca tgtttgtgtt agatccgtgt tgtgttaga tccgtgctgc    5700 tagcgttcgt acacggatgc gacctgtacg tcagacacgt tctgattgct aacttgccag    5760
tgtttctctt tggggaatcc tgggatggct ctagccgttc cgcagacggg atcgatttca    5820 tgatttttt tgtttcgttg catagggttt ggtttgccct tttccttat ttcaatatat    5880 gccgtgcact tgtttgtcgg gtcatctttt catgctttt tttgtcttgg ttgtgatgat    5940
gtggtctggt tgggcggtcg ttctagatcg gagtagaatt ctgtttcaaa ctacctggtg    6000
gatttattaa ttttggatct gtatgtgtgt gccatacata ttcatagtta cgaattgaag    6060
atgatggatg gaaatatcga tctaggatag gtatacatgt tgatgcgggt tttactgatg    6120
catatacaga gatgcttttt gttcgcttgg ttgtgatgat gtggtgtggt tgggcggtcg    6180
ttcattcgtt ctagatcgga gtagaatact gtttcaaact acctggtgta tttattaatt    6240
ttggaactgt atgtgtgtgt catacatctt catagttacg agtttaagat ggatggaaat    6300
atcgatctag gataggtata catgttgatg tgggttttac tgatgcatat acatgatggc    6360
atatgcagca tctattcata tgctctaacc ttgagtacct atctattata ataaacaagt    6420
atgttttata attattttga tcttgatata cttggatgat ggcatatgca gcagctatat    6480 gtggatttt ttagccctgc cttcatacgc tatttatttg cttggtactg tttcttttgt    6540
cgatgctcac cctgttgttt ggtgttactt ctgcaggtcg actttaactt agcctaggat    6600
ccacacgaca ccatgtcccc cgagcgccgc cccgtcgaga tccgcccggc caccgccgcc    6660
gacatggccg ccgtgtgcga catcgtgaac cactacatcg agacctccac cgtgaacttc    6720
cgcaccgagc cgcagacccc gcaggagtgg atcgacgacc tggagcgcct ccaggaccgc    6780
tacccgtggc tcgtggccga ggtggagggc gtggtggccg gcatcgccta cgccggcccg    6840
tggaaggccc gcaacgccta cgactggacc gtggagtcca ccgtgtacgt gtcccaccgc    6900
caccagcgcc tcggcctcgg ctccaccctc tacacccacc tcctcaagag catggaggcc    6960
cagggcttca gtccgtggt ggccgtgatc ggcctcccga acgacccgtc cgtgcgcctc    7020
cacgaggccc tcggctacac cgcccgcggc accctccgcg ccgccggcta caagcacggc    7080
ggctggcacg acgtcggctt ctggcagcgc gacttcgagc tgccggcccc gccgcgcccg    7140
gtgcgcccgg tgacgcagat ctgagtcgaa acctagactt gtccatcttc tggattggcc    7200
aacttaatta atgtatgaaa taaaaggatg cacacatagt gacatgctaa tcactataat    7260
gtgggcatca aagttgtgtg ttatgtgtaa ttactagtta tctgaataaa agagaaagag    7320
atcatccata tttcttatcc taaatgaatg tcacgtgtct ttataattct tgatgaacc    7380
```

```
agatgcattt cattaaccaa atccatatac atataaatat taatcatata taattaatat    7440
caattgggtt agcaaaacaa atctagtcta ggtgtgtttt gcgaatgcgg ccgataagtg    7500
actagggtca cgtgacccta gtcacttagg taccgagctc gaattcattc cgattaatcg    7560
tggcctcttg ctcttcagga tgaagagcta tgtttaaacg tgcaagcgct actagacaat    7620
tcagtacatt aaaaacgtcc gcaatgtgtt attaagttgt ctaagcgtca atttgtttac    7680
accacaatat atcctgccac cagccagcca acagctcccc gaccggcagc tcggcacaaa    7740
atcaccactc gatacaggca gcccatcagt ccgggacggc gtcagcggga gagccgttgt    7800
aaggcggcag actttgctca tgttaccgat gctattcgga agaacggcaa ctaagctgcc    7860
gggtttgaaa cacggatgat ctcgcggagg gtagcatgtt gattgtaacg atgacagagc    7920
gttgctgcct gtgatcaaat atcatctccc tcgcagagat ccgaattatc agccttctta    7980
ttcatttctc gcttaaccgt gacaggctgt cgatcttgag aactatgccg acataatagg    8040
aaatcgctgg ataagccgc tgaggaagct gagtggcgct atttctttag aagtgaacgt    8100
tgacgatcgt cgaccgtacc ccgatgaatt aattcggacg tacgttctga acacagctgg    8160
atacttactt gggcgattgt catacatgac atcaacaatg tacccgtttg tgtaaccgtc    8220
tcttggaggt tcgtatgaca ctagtggttc ccctcagctt gcgactagat gttgaggcct    8280
aacattttat tagagagcag gctagttgct tagatacatg atcttcaggc cgttatctgt    8340
cagggcaagc gaaaattggc catttatgac gaccaatgcc ccgcagaagc tcccatcttt    8400
gccgccatag acgccgcgcc ccccttttgg ggtgtagaac atcctttgc cagatgtgga    8460
aaagaagttc gttgtcccat tgttggcaat gacgtagtag ccggcgaaag tgcgagaccc    8520
atttgcgcta tatataagcc tacgatttcc gttgcgacta ttgtcgtaat tggatgaact    8580
attatcgtag ttgctctcag agttgtcgta atttgatgga ctattgtcgt aattgcttat    8640
ggagttgtcg tagttgcttg gagaaatgtc gtagttggat ggggagtagt catagggaag    8700
acgagcttca tccactaaaa caattggcag gtcagcaagt gcctgccccg atgccatcgc    8760
aagtacgagg cttagaacca ccttcaacag atcgcgcata gtcttcccca gctctctaac    8820
gcttgagtta agccgcgccg cgaagcggcg tcggcttgaa cgaattgtta gacattattt    8880
gccgactacc ttggtgatct cgcctttcac gtagtgaaca aattcttcca actgatctgc    8940
gcgcgaggcc aagcgatctt cttgtccaag ataagcctgc ctagcttcaa gtatgacggg    9000
ctgatactgg gccggcaggc gctccattgc ccagtcggca gcgacatcct tcggcgcgat    9060
tttgccggtt actgcgctgt accaaatgcg ggacaacgta agcactacat ttcgctcatc    9120
gccagcccag tcgggcggcg agttccatag cgttaaggtt tcatttagcg cctcaaatag    9180
atcctgttca ggaaccggat caaagagttc ctccgccgct ggacctacca aggcaacgct    9240
atgttctctt gcttttgtca gcaagatagc cagatcaatg tcgatcgtgg ctggctcgaa    9300
gatacctgca agaatgtcat tgcgctgcca ttctccaaat tgcagttcgc gcttagctgg    9360
ataacgccac ggaatgatgt cgtcgtgcac aacaatggtg acttctacag cgcggagaat    9420
ctcgctctct ccaggggaag ccgaagtttc caaaaggtcg ttgatcaaag ctcgccgcgt    9480
tgtttcatca agccttacag tcaccgtaac cagcaaatca atatcactgt gtggcttcag    9540
gccgccatcc actgcggagc cgtacaaatg tacggccagc aacgtcggtt cgagatggcg    9600
ctcgatgacg ccaactacct ctgatagttg agtcgatact tcggcgatca ccgcttccct    9660
catgatgttt aactcctgaa ttaagccgcg ccgcgaagcg gtgtcggctt gaatgaattg    9720
ttaggcgtca tcctgtgctc ccgagaacca gtaccagtac atcgctgttt cgttcgagac    9780
```

```
ttgaggtcta gttttatacg tgaacaggtc aatgccgccg agagtaaagc cacattttgc    9840
gtacaaattg caggcaggta cattgttcgt ttgtgtctct aatcgtatgc caaggagctg    9900
tctgcttagt gcccactttt tcgcaaattc gatgagactg tgcgcgactc ctttgcctcg    9960
gtgcgtgtgc gacacaacaa tgtgttcgat agaggctaga tcgttccatg ttgagttgag   10020
ttcaatcttc ccgacaagct cttggtcgat gaatgcgcca tagcaagcag agtcttcatc   10080
agagtcatca tccgagatgt aatccttccg gtaggggctc acacttctgg tagatagttc   10140
aaagccttgg tcggataggt gcacatcgaa cacttcacga caatgaaat ggttctcagc    10200
atccaatgtt tccgccacct gctcaggat caccgaaatc ttcatatgac gcctaacgcc     10260
tggcacagcg gatcgcaaac ctggcgcggc ttttggcaca aaaggcgtga caggtttgcg   10320
aatccgttgc tgccacttgt taacccttt gccagatttg gtaactataa tttatgttag     10380
aggcgaagtc ttgggtaaaa actggcctaa aattgctggg gatttcagga aagtaaacat   10440
caccttccgg ctcgatgtct attgtagata tatgtagtgt atctacttga tcggggatc    10500
tgctgcctcg cgcgtttcgg tgatgacggt gaaaaccctct gacacatgca gctcccggag  10560
acggtcacag cttgtctgta agcggatgcc gggagcagac aagcccgtca gggcgcgtca   10620
gcgggtgttg gcgggtgtcg gggcgcagcc atgacccagt cacgtagcga tagcggagtg   10680
tatactggct taactatgcg gcatcagagc agattgtact gagagtgcac catatgcggt   10740
gtgaaatacc gcacagatgc gtaaggagaa ataccgcat caggcgctct ccgcttcct     10800
cgctcactga ctcgctgcgc tcggtcgttc ggctgcggcg agcggtatca gctcactcaa   10860
aggcggtaat acggttatcc acagaatcag gggataacgc aggaaagaac atgtgagcaa   10920
aaggccagca aaaggccagg aaccgtaaaa aggccgcgtt gctggcgttt ttccataggc   10980
tccgcccccc tgacgagcat cacaaaaatc gacgctcaag tcagaggtgg cgaaacccga   11040
caggactata aagataccag gcgtttcccc ctggaagctc cctcgtgcgc tctcctgttc   11100
cgaccctgcc gcttaccgga tacctgtccg cctttctccc ttcgggaagc gtggcgcttt   11160
ctcatagctc acgctgtagg tatctcagtt cggtgtaggt cgttcgctcc aagctgggct   11220
gtgtgcacga accccccgtt cagcccgacc gctgcgcctt atccggtaac tatcgtcttg   11280
agtccaaccc ggtaagacac gacttatcgc cactggcagc agccactggt aacaggatta   11340
gcagagcgag gtatgtaggc ggtgctacag agttcttgaa gtggtggcct aactacggct   11400
acactagaag gacagtattt ggtatctgcg ctctgctgaa gccagttacc ttcggaaaaa   11460
gagttggtag ctcttgatcc ggcaaacaaa ccaccgctgg tagcggtggt ttttttgttt   11520
gcaagcagca gattacgcgc agaaaaaaag gatctcaaga agatcctttg atcttttcta   11580
cggggtctga cgctcagtgg aacgaaaact cacgttaagg gattttggtc atgagattat   11640
caaaaaggat cttcacctag atccttttaa attaaaaatg aagttttaaa tcaatctaaa   11700
gtatatatga gtaaacttgg tctgacagtt accaatgctt aatcagtgag gcacctatct   11760
cagcgatctg tctatttcgt tcatccatag ttgcctgact ccccgtcgtg tagataacta   11820
cgatacggga gggcttacca tctggcccca gtgctgcaat gataccgcga acccacgct    11880
caccggctcc agatttatca gcaataaacc agccagccgg aagggccgag cgcagaagtg   11940
gtcctgcaac tttatccgcc tccatccagt ctattaattg ttgccgggaa gctagagtaa   12000
gtagttcgcc agttaatagt ttgcgcaacg ttgttgccat tgctgcaggg ggggggggg    12060
gggggttcca ttgttcattc cacggacaaa aacagagaaa ggaaacgaca gaggccaaaa   12120
```

```
agctcgcttt cagcacctgt cgtttcctttt cttttcagag ggtattttaa ataaaaacat    12180
taagttatga cgaagaagaa cggaaacgcc ttaaaccgga aaattttcat aaatagcgaa    12240
aacccgcgag gtcgccgccc cgtaacctgt cggatcaccg gaaaggaccc gtaaagtgat    12300
aatgattatc atctacatat cacaacgtgc gtggaggcca tcaaaccacg tcaaataatc    12360
aattatgacg caggtatcgt attaattgat ctgcatcaac ttaacgtaaa aacaacttca    12420
gacaatacaa atcagcgaca ctgaatacgg ggcaaccctca tgtcccccccc cccccccccc    12480 ctgcaggcat cgtggtgtca cgctcgtcgt ttggtatggc ttcattcagc tccggttccc    12540
aacgatcaag gcgagttaca tgatccccca tgttgtgcaa aaaagcggtt agctccttcg    12600
gtcctccgat cgttgtcaga agtaagttgg ccgcagtgtt atcactcatg gttatggcag    12660
cactgcataa ttctcttact gtcatgccat ccgtaagatg cttttctgtg actggtgagt    12720
actcaaccaa gtcattctga gaatagtgta tgcggcgacc gagttgctct tgcccggcgt    12780
caacacggga taataccgcg ccacatagca gaactttaaa agtgctcatc attggaaaac    12840
gttcttcggg gcgaaaactc tcaaggatct taccgctgtt gagatccagt tcgatgtaac    12900
ccactcgtgc acccaactga tcttcagcat cttttacttt caccagcgtt tctgggtgag    12960
caaaaacagg aaggcaaaat gccgcaaaaa agggaataag ggcgacacgg aaatgttgaa    13020
tactcatact cttccttttt caatattatt gaagcattta tcagggttat tgtctcatga    13080
gcggatacat atttgaatgt atttagaaaa ataaacaaat aggggttccg cgcacatttc    13140
cccgaaaagt gccacctgac gtctaagaaa ccattattat catgacatta acctataaaa    13200
ataggcgtat cacgaggccc tttcgtcttc aagaattcgg agcttttgcc attctcaccg    13260
gattcagtcg tcactcatgg tgatttctca cttgataacc ttattttga cgaggggaaa    13320 ttaataggtt gtattgatgt tggacgagtc ggaatcgcag accgatacca ggatcttgcc    13380
atcctatgga actgcctcgg tgagttttct ccttcattac agaaacggct ttttcaaaaa    13440
tatggtattg ataatcctga tatgaataaa ttgcagtttc atttgatgct cgatgagttt    13500
ttctaatcag aattggttaa ttggttgtaa cactggcaga gcattacgct gacttgacgg    13560
gacggcggct ttgttgaata aatcgaactt ttgctgagtt gaaggatcag atcacgcatc    13620
ttcccgacaa cgcagaccgt tccgtggcaa agcaaaagtt caaaatcacc aactggtcca    13680
cctacaacaa agctctcatc aaccgtggct ccctcacttt ctggctggat gatggggcga    13740
ttcaggcctg gtatgagtca gcaacacctt cttcacgagg cagacctcag cgccagaagg    13800
ccgccagaga ggccgagcgc ggccgtgagg cttggacgct agggcagggc atgaaaaagc    13860
ccgtagcggg ctgctacggg cgtctgacgc ggtggaaagg gggaggggat gttgtctaca    13920
tggctctgct gtagtgagtg ggttgcgctc cggcagcggt cctgatcaat cgtcacccttt    13980 tctcggtcct tcaacgttcc tgacaacgag cctccttttc gccaatccat cgacaatcac    14040
cgcgagtccc tgctcgaacg ctgcgtccgg accggcttcg tcgaaggcgt ctatcgcggc    14100
ccgcaacagc ggcgagagcg gagcctgttc aacggtgccg ccgcgctcgc cggcatcgct    14160
gtcgccggcc tgctcctcaa gcacggcccc aacagtgaag tagctgattg tcatcagcgc    14220
attgacggca tccccggccg aaaaaccccg ctcgcagagg aagcgaagct gcgcgtcggc    14280
cgtttccatc tgcggtgcgc ccggtcgcgt gccggcatgg atgcgcgcgc catcgcggta    14340
ggcgagcagc gcctgcctga agctgcgggc attcccgatc agaaatgagc gccagtcgtc    14400
gtcggctctc ggcaccgaat gcgtatgatt ctccgccagc atggcttcgg ccagtgcgtc    14460
gagcagcgcc cgcttgttcc tgaagtgcca gtaaagcgcc ggctgctgaa cccccaaccg    14520
```

```
ttccgccagt ttgcgtgtcg tcagaccgtc tacgccgacc tcgttcaaca ggtccagggc    14580
ggcacggatc actgtattcg gctgcaactt tgtcatgctt gacactttat cactgataaa    14640
cataatatgt ccaccaactt atcagtgata aagaatccgc gcgttcaatc ggaccagcgg    14700
aggctggtcc ggaggccaga cgtgaaaccc aacataccc tgatcgtaat tctgagcact     14760
gtcgcgctcg acgctgtcgg catcggcctg attatgccgg tgctgccggg cctcctgcgc    14820
gatctggttc actcgaacga cgtcaccgcc cactatggca ttctgctggc gctgtatgcg    14880
ttggtgcaat ttgcctgcgc acctgtgctg ggcgcgctgt cggatcgttt cgggcggcgg    14940
ccaatcttgc tcgtctcgct ggccggcgcc actgtcgact acgccatcat ggcgacagcg    15000
cctttccttt gggttctcta tcgggcgg atcgtggccg gcatcaccgg ggcgactggg       15060
gcggtagccg gcgcttatat tgccgatatc actgatggcg atgagcgcgc gcggcacttc    15120
ggcttcatga gcgcctgttt cgggttcggg atggtcgcgg gacctgtgct cggtgggctg    15180
atgggcggtt tctcccccca cgctccgttc ttcgccgcgg cagccttgaa cggcctcaat    15240
ttcctgacgg gctgtttcct tttgccggag tcgcacaaag gcgaacgccg gccgttacgc    15300
cgggaggctc tcaacccgct cgcttcgttc cggtgggccc ggggcatgac cgtcgtcgcc    15360
gccctgatgg cggtcttctt catcatgcaa cttgtcggac aggtgccggc cgcgctttgg    15420
gtcattttcg gcgaggatcg ctttcactgg gacgcgacca cgatcggcat ttcgcttgcc    15480
gcatttggca ttctgcattc actcgcccag gcaatgatca ccggccctgt agccgcccgg    15540
ctcggcgaaa ggcgggcact catgctcgga atgattgccg acggcacagg ctacatcctg    15600
cttgccttcg cgacacgggg atggatggcg ttcccgatca tggtcctgct tgcttcgggt    15660
ggcatcggaa tgccggcgct gcaagcaatg ttgtccaggc aggtggatga ggaacgtcag    15720
gggcagctgc aaggctcact ggcggcgctc accagcctga cctcgatcgt cggacccctc    15780
ctcttcacgg cgatctatgc ggcttctata acaacgtgga acgggtgggc atggattgca    15840
ggcgctgccc tctacttgct ctgcctgccg gcgctgcgtc gcgggctttg gagcggcgca    15900
gggcaacgag ccgatcgctg atcgtggaaa cgataggcct atgccatgcg ggtcaaggcg    15960
acttccggca agctatacgc gccctaggag tgcggttgga acgttggccc agccagatac    16020
tcccgatcac gagcaggacg ccgatgattt gaagcgcact cagcgtctga tccaagaaca    16080
accatcctag caacacggcg gtccccgggc tgagaaagcc cagtaaggaa acaactgtag    16140
gttcgagtcg cgagatcccc cggaaccaaa ggaagtaggt taaacccgct ccgatcaggc    16200
cgagccacgc caggccgaga acattggttc ctgtaggcat cgggattggc ggatcaaaca    16260
ctaaagctac tggaacgagc agaagtcctc cggccgccag ttgccaggcg gtaaaggtga    16320
gcagaggcac gggaggttgc cacttgcggg tcagcacggt tccgaacgcc atggaaaccg    16380
cccccgccag gcccgctgcg acgccgacag gatctagcgc tgcgtttggt gtcaacacca    16440
acagcgccac gcccgcagtt ccgcaaatag ccccaggac cgccatcaat cgtatcgggc      16500
tacctagcag agcggcagag atgaacacga ccatcagcgg ctgcacagcg cctaccgtcg    16560
ccgcgacccc gccggcagg cggtagaccg aaataaacaa caagctccag aatagcgaaa     16620
tattaagtgc gccgaggatg aagatgcgca tccaccagat tcccgttgga atctgtcgga    16680
cgatcatcac gagcaataaa cccgccggca acgcccgcag cagcataccg gcgacccctc    16740
ggcctcgctg ttcgggctcc acgaaaacgc cggacagatg cgccttgtga gcgtccttgg    16800
ggccgtcctc ctgtttgaag accgacagcc caatgatctc gccgtcgatg taggcgccga    16860
```

-continued

```
atgccacggc atctcgcaac cgttcagcga acgcctccat gggcttttc tcctcgtgct   16920
cgtaaacgga cccgaacatc tctggagctt tcttcaggc cgacaatcgg atctcgcgga   16980
aatcctgcac gtcggccgct ccaagccgtc gaatctgagc cttaatcaca attgtcaatt   17040
ttaatcctct gtttatcggc agttcgtaga gcgcgccgtg cgtcccgagc gatactgagc   17100
gaagcaagtg cgtcgagcag tgcccgcttg ttcctgaaat gccagtaaag cgctggctgc   17160
tgaaccccca gccggaactg accccacaag gccctagcgt ttgcaatgca ccaggtcatc   17220
attgacccag gcgtgttcca ccaggccgct gcctcgcaac tcttcgcagg cttcgccgac   17280
ctgctcgcgc cacttcttca cgcgggtgga atccgatccg cacatgaggc ggaaggtttc   17340
cagcttgagc gggtacggct cccggtgcga gctgaaatag tcgaacatcc gtcgggccgt   17400
cggcgacagc ttgcggtact tctcccatat gaatttcgtg tagtggtcgc cagcaaacag   17460
cacgacgatt tcctcgtcga tcaggacctg gcaacgggac gttttcttgc cacggtccag   17520
gacgcggaag cggtgcagca gcgacaccga ttccaggtgc ccaacgcggt cggacgtgaa   17580
gcccatcgcc gtcgcctgta ggcgcgacag gcattcctcg gccttcgtgt aataccggcc   17640
attgatcgac cagcccaggt cctggcaaag ctcgtagaac gtgaaggtga tcggctcgcc   17700
gataggggtg cgcttcgcgt actccaacac ctgctgccac accagttcgt catcgtcggc   17760
ccgcagctcg acgccggtgt aggtgatctt cacgtccttg ttgacgtgga aaatgacctt   17820
gttttgcagc gcctcgcgcg ggattttctt gttgcgcgtg gtgaacaggg cagagcgggc   17880
cgtgtcgttt ggcatcgctc gcatcgtgtc cggccacggc gcaatatcga acaaggaaag   17940
ctgcatttcc ttgatctgct gcttcgtgtg tttcagcaac gcggcctgct ggcctcgct   18000
gacctgtttt gccaggtcct cgccggcggt ttttcgcttc ttggtcgtca tagttcctcg   18060
cgtgtcgatg gtcatcgact tcgccaaacc tgccgcctcc tgttcgagac gacgcgaacg   18120
ctccacggcg gccgatggcg cgggcagggc aggggagcc agttgcacgc tgtcgcgctc   18180
gatcttggcc gtagcttgct ggaccatcga gccgacggac tggaaggttt cgcggggcgc   18240
acgcatgacg gtgcggcttg cgatggtttc ggcatcctcg gcggaaaacc ccgcgtcgat   18300
cagttcttgc ctgtatgcct tccggtcaaa cgtccgattc attcaccctc cttgcgggat   18360
tgccccgact cacgccgggg caatgtgccc ttattcctga tttgacccgc ctggtgcctt   18420
ggtgtccaga taatccacct tatcggcaat gaagtcggtc ccgtagaccg tctgccgtc   18480
cttctcgtac ttggtattcc gaatcttgcc ctgcacgaat accagcgacc ccttgcccaa   18540
atacttgccg tgggcctcgg cctgagagcc aaaacacttg atgcggaaga agtcggtgcg   18600
ctcctgcttg tcgccggcat cgttgcgcca ctcttcatta accgctatat cgaaaattgc   18660
ttgcggcttg ttagaattgc catgacgtac ctcggtgtca cgggtaagat taccgataaa   18720
ctggaactga ttatggctca tatcgaaagt ctccttgaga aaggagactc tagtttagct   18780
aaacattggt tccgctgtca agaactttag cggctaaaat tttgcgggcc gcgaccaaag   18840
gtgcgagggg cggcttccgc tgtgtacaac cagatatttt tcaccaacat ccttcgtctg   18900
ctcgatgagc ggggcatgac gaaacatgag ctgtcggaga gggcagggt ttcaatttcg   18960
tttttatcag acttaaccaa cggtaaggcc aaccctcgt tgaaggtgat ggaggccatt   19020
gccgacgccc tggaaactcc cctacctctt ctcctggagt ccaccgacct tgaccgcgag   19080
gcactcgcgg agattgcggg tcatcctttc aagagcagcg tgccgccgg atacgaacgc   19140
atcagtgtgg tttttgccgtc acataaggcg tttatcgtaa agaaatgggg cgacgacacc   19200
cgaaaaaagc tgcgtggaag gctctgacgc caagggttag ggcttgcact tccttcttta   19260
```

```
gccgctaaaa cggccccttc tctgcgggcc gtcggctcgc gcatcatatc gacatcctca    19320
acggaagccg tgccgcgaat ggcatcgggc gggtgcgctt tgacagttgt tttctatcag    19380 aaccccctacg tcgtgcggtt cgattagctg tttgtcttgc aggctaaaca ctttcggtat    19440
atcgtttgcc tgtgcgataa tgttgctaat gatttgttgc gtaggggtta ctgaaaagtg    19500
agcgggaaag aagagtttca gaccatcaag gagcgggcca agcgcaagct ggaacgcgac    19560
atgggtgcga acctgttggc cgcgctcaac gacccgaaaa ccgttgaagt catgctcaac    19620
gcggacggca aggtgtggca cgaacgcctt ggcgagccga tgcggtacat ctgcgacatg    19680
cggcccagcc agtcgcaggc gattatagaa acggtggccg gattccacgg caaagaggtc    19740
acgcggcatt cgcccatcct ggaaggcgag ttccccttgg atggcagccg ctttgccggc    19800
caattgccgc cggtcgtggc cgcgccaacc tttgcgatcc gcaagcgcgc ggtcgccatc    19860
ttcacgctgg aacagtacgt cgaggcgggc atcatgaccc gcgagcaata cgaggtcatt    19920
aaaagcgccg tcgcggcgca tcgaaacatc ctcgtcattg gcggtactgg ctcgggcaag    19980
accacgctcg tcaacgcgat catcaatgaa atggtcgcct tcaacccgtc tgagcgcgtc    20040
gtcatcatcg aggacaccgg cgaaatccag tgcgccgcag agaacgccgt ccaataccac    20100
accagcatcg acgtctcgat gacgctgctg ctcaagacaa cgctgcgtat gcgccccgac    20160
cgcatcctgg tcggtgaggt acgtggcccc gaagcccttg atctgttgat ggcctggaac    20220
accgggcatg aaggaggtgc cgccaccctg cacgcaaaca accccaaagc gggcctgagc    20280
cggctcgcca tgcttatcag catgcacccg gattcaccga aacccattga gccgctgatt    20340
ggcgaggcgg ttcatgtggt cgtccatatc gccaggaccc ctagcggccg tcgagtgcaa    20400
gaaattctcg aagttcttgg ttacgagaac ggccagtaca tcaccaaaac cctgtaagga    20460
gtatttccaa tgacaacggc tgttccgttc cgtctgacca tgaatcgcgg cattttgttc    20520
taccttgccg tgttcttcgt tctcgctctc gcgttatccg cgcatccggc gatggcctcg    20580
gaaggcaccg gcggcagctt gccatatgag agctggctga cgaacctgcg caactccgta    20640
accggcccgg tggccttcgc gctgtccatc atcggcatcg tcgtcgccgg cggcgtgctg    20700
atcttcggcg gcgaactcaa cgccttcttc cgaaccctga tcttcctggt tctggtgatg    20760
gcgctgctgg tcggcgcgca gaacgtgatg agcaccttct tcggtcgtgg tgccgaaatc    20820
gcggccctcg gcaacgggc gctgcaccag gtgcaagtcg cggcggcgga tgccgtgcgt    20880
gcggtagcgg ctggacggct cgcctaatca tggctctgcg cacgatcccc atccgtcgcg    20940
caggcaaccg agaaaacctg ttcatggggtg gtgatcgtga actggtgatg ttctcgggcc    21000
tgatggcgtt tgcgctgatt ttcagcgccc aagagctgcg ggccaccgtg gtcggtctga    21060
tcctgtggtt cggggcgctc tatgcgttcc gaatcatggc gaaggccgat ccgaagatgc    21120
ggttcgtgta cctgcgtcac cgccggtaca agccgtatta cccggcccgc tcgacccgt    21180 tccgcgagaa caccaatagc caagggaagc aataccgatg atccaagcaa ttgcgattgc    21240
aatcgcgggc ctcggcgcgc ttctgttgtt catcctcttt gcccgcatcc gcgcggtcga    21300
tgccgaactg aaactgaaaa agcatcgttc caaggacgcc ggcctggccg atctgctcaa    21360
ctacgccgct gtcgtcgatg acggcgtaat cgtgggcaag aacggcagct ttatggctgc    21420
ctggctgtac aagggcgatg acaacgcaag cagcaccgac cagcagcgcg aagtagtgtc    21480
cgcccgcatc aaccaggccc tcgcgggcct gggaagtggg tggatgatcc atgtggacgc    21540
cgtgcggcgt cctgctccga actacgcgga gcggggcctg tcggcgttcc ctgaccgtct    21600
```

```
gacggcagcg attgaagaag agcgctcggt cttgccttgc tcgtcggtga tgtacttcac   21660
cagctccgcg aagtcgctct tcttgatgga gcgcatgggg acgtgcttgg caatcacgcg   21720
cacccccggg ccgttttagc ggctaaaaaa gtcatggctc tgccctcggg cggaccacgc   21780
ccatcatgac cttgccaagc tcgtcctgct tctcttcgat cttcgccagc agggcgagga   21840
tcgtggcatc accgaaccgc gccgtgcgcg ggtcgtcggt gagccagagt ttcagcaggc   21900
cgcccaggcg gcccaggtcg ccattgatgc gggccagctc gcggacgtgc tcatagtcca   21960
cgacgcccgt gattttgtag ccctggccga cggccagcag gtaggccgac aggctcatgc   22020
cggccgccgc cgccttttcc tcaatcgctc ttcgttcgtc tggaaggcag tacaccttga   22080
taggtgggct gcccttcctg gttggcttgg tttcatcagc catccgcttg ccctcatctg   22140
ttacgccggc ggtagccggc cagcctcgca gagcaggatt cccgttgagc accgccaggt   22200
gcgaataagg gacagtgaag aaggaacacc cgctcgcggg tgggcctact tcacctatcc   22260
tgcccggctg acgccgttgg atacaccaag gaaagtctac acgaaccctt tggcaaaatc   22320
ctgtatatcg tgcgaaaaag gatggatata ccgaaaaaat cgctataatg ccccgaagc    22380
agggttatgc agcggaaaag cgctgcttcc ctgctgtttt gtggaatatc taccgactgg   22440
aaacaggcaa atgcaggaaa ttactgaact gaggggacag gcgagagacg atgccaagaa   22500
gctacaccga cgagctggcc gagtgggttg aatcccgcgc ggccaagaag cgccggcgtg   22560
atgaggctgc ggttgcgttc ctggcggtga gggcggatgt cgaggcggcg ttagcgtccg   22620
gctatgcgct cgtcaccatt tgggagcaca tgcgggaaac ggggaaggtc aagttctcct   22680
acgagacgtt ccgctcgcac gccaggcggc acatcaaggc caagcccgcc gatgtgcccg   22740
caccgcaggc caaggctgcg gaacccgcgc cggcacccaa gacgccggag ccacggcggc   22800
cgaagcaggg gggcaaggct gaaaagccgg ccccgctgc ggccccgacc ggcttcacct    22860
tcaacccaac accggacaaa aaggatctac tgtaatggcg aaaattcaca tggttttgca   22920
gggcaagggc ggggtcggca agtcggccat cgccgcgatc attgcgcagt acaagatgga   22980
caaggggcag acacccttgt gcatcgacac cgacccggtg aacgcgacgt cgagggcta    23040
caaggccctg aacgtccgcc ggctgaacat catggccggc gacgaaatta actcgcgcaa   23100
cttcgacacc ctggtcgagc tgattgcgcc gaccaaggat gacgtggtga tcgacaacgg   23160
tgccagctcg ttcgtgcctc tgtcgcatta cctcatcagc aaccaggtgc cggctctgct   23220
gcaagaaatg gggcatgagc tggtcatcca taccgtcgtc accggcggcc aggctctcct   23280
ggacacggtg agcggcttcg cccagctcgc cagccagttc ccggccgaag cgcttttcgt   23340
ggtctggctg aacccgtatt gggggcctat cgagcatgag ggcaagagct ttgagcagat   23400
gaaggcgtac acggccaaca aggcccgcgt gtcgtccatc atccagattc cggccctcaa   23460
ggaagaaacc tacggccgcg atttcagcga catgctgcaa gagcggctga cgttcgacca   23520
ggcgctggcc gatgaatcgc tcacgatcat gacgcggcaa cgcctcaaga tcgtgcggcg   23580
cggcctgttt gaacagctcg acgcggcggc cgtgctatga gcgaccagat tgaagagctg   23640
atccgggaga ttgcggccaa gcacggcatc gccgtcggcc gcgacgaccc ggtgctgatc   23700
ctgcatacca tcaacgcccg gctcatggcc gacagtgcgg ccaagcaaga ggaaatcctt   23760
gccgcgttca aggaagagct ggaagggatc gcccatcgtt ggggcgagga cgccaaggcc   23820
aaagcggagc ggatgctgaa cgcggccctg gcggccagca aggacgcaat ggcgaaggta   23880
atgaaggaca cgccgcgca ggcggccgaa gcgatccgca gggaaatcga cgacggcctt    23940
ggccgccagc tcgcggccaa ggtcgcggac gcgcggcgcg tggcgatgat gaacatgatc   24000
```

```
gccggcggca tggtgttgtt cgcggccgcc ctggtggtgt gggcctcgtt atgaatcgca    24060
gaggcgcaga tgaaaaagcc cggcgttgcc gggctttgtt tttgcgttag ctgggcttgt    24120
ttgacaggcc caagctctga ctgcgcccgc gctcgcgctc ctgggcctgt tcttctcct    24180 gctcctgctt gcgcatcagg gcctggtgcc gtcgggctgc ttcacgcatc gaatcccagt    24240
cgccggccag ctcgggatgc tccgcgcgca tcttgcgcgt cgccagttcc tcgatcttgg    24300
gcgcgtgaat gcccatgcct tccttgattt cgcgcaccat gtccagccgc gtgtgcaggg    24360
tctgcaagcg ggcttgctgt tgggcctgct gctgctgcca ggcggccttt gtacgcggca    24420
gggacagcaa gccgggggca ttggactgta gctgctgcaa acgcgcctgc tgacggtcta    24480
cgagctgttc taggcggtcc tcgatgcgct ccacctggtc atgctttgcc tgcacgtaga    24540
gcgcaagggt ctgctggtag gtctgctcga tgggcgcgga ttctaagagg gcctgctgtt    24600
ccgtctcggc ctcctgggcc gcctgtagca atcctcgcc gctgttgccg ctggactgct    24660
ttactgccgg ggactgctgt tgccctgctc gcgccgtcgt cgcagttcgg cttgcccca    24720 ctcgattgac tgcttcattt cgagccgcag cgatgcgatc tcggattgcg tcaacggacg    24780
gggcagcgcg gaggtgtccg gcttctcctt gggtgagtcg gtcgatgcca tagccaaagg    24840
tttccttcca aaatgcgtcc attgctggac cgtgtttctc attgatgccc gcaagcatct    24900
tcggcttgac cgccaggtca agcgcgcctt catgggcggt catgacggac gccgccatga    24960
ccttgccgcc gttgttctcg atgtagccgc gtaatgaggc aatggtgccg cccatcgtca    25020
gcgtgtcatc gacaacgatg tacttctggc cggggatcac ctcccctcg aaagtcgggt     25080 tgaacgccag gcgatgatct gaaccggctc cggttcgggc gaccttctcc cgctgcacaa    25140
tgtccgtttc gacctcaagg ccaaggcggt cggccagaac gaccgccatc atggccggaa    25200
tcttgttgtt ccccgccgcc tcgacggcga ggactggaac gatgcggggc ttgtcgtcgc    25260
cgatcagcgt cttgagctgg gcaacagtgt cgtccgaaat caggcgctcg accaaattaa    25320
gcgccgcttc cgcgtcgccc tgcttcgcag cctggtattc aggctcgttg gtcaaagaac    25380
caaggtcgcc gttgcgaacc accttcggga agtctcccca cggtgcgcgc tcggctctgc    25440
tgtagctgct caagacgcct cccttttag ccgctaaaac tctaacgagt gcgcccgcga     25500
ctcaacttga cgctttcggc acttaccgt gccttgccac ttgcgtcata ggtgatgctt     25560
ttcgcactcc cgatttcagg tactttatcg aaatctgacc gggcgtgcat acaaagttc     25620 ttccccacct gttggtaaat gctgccgcta tctgcgtgga cgatgctgcc gtcgtggcgc    25680
tgcgacttat cggccttttg ggccatatag atgttgtaaa tgccaggttt cagggccccg    25740
gctttatcta ccttctggtt cgtccatgcg ccttggttct cggtctggac aattctttgc    25800
ccattcatga ccaggaggcg tgtttcatt gggtgactcc tgacggttgc ctctggtgtt     25860
aaacgtgtcc tggtcgcttg ccggctaaaa aaagccgac ctcggcagtt cgaggccggc     25920
tttccctaga gccgggcgcg tcaaggttgt tccatctatt ttagtgaact gcgttcgatt    25980
tatcagttac tttcctcccg cttgtgtttt cctcccactc gtttccgcgt ctagccgacc    26040
cctcaacata gcggcctctt cttgggctgc ctttgcctct tgccgcgctt cgtcacgctc    26100
ggcttgcacc gtcgtaaagc gctcggcctg cctggccgcc tcttgcgccg ccaacttcct    26160
ttgctcctgg tgggcctcgg cgtcggcctg cgccttcgct ttcaccgctg ccaactccgt    26220
gcgcaaactc tccgcttcgc gcctggtggc gtcgcgctcg ccgcgaagcg cctgcatttc    26280
ctggttggcc gcgtccaggg tcttgcggct ctcttctttg aatgcgcggg cgtcctggtg    26340
```

```
agcgtagtcc agctcggcgc gcagctcctg cgctcgacgc tccacctcgt cggcccgctg    26400
cgtcgccagc gcggcccgct gctcggctcc tgccagggcg gtgcgtgctt cggccagggc    26460
ttgccgctgg cgtgcggcca gctcggccgc ctcggcggcc tgctgctcta gcaatgtaac    26520
gcgcgcctgg gcttcttcca gctcgcgggc ctgcgcctcg aaggcgtcgg ccagctcccc    26580
gcgcacggct tccaactcgt tgcgctcacg atcccagccg gcttgcgctg cctgcaacga    26640
ttcattggca agggcctggg cggcttgcca gagggcggcc acggcctggt tgccggcctg    26700
ctgcaccgcg tccggcacct ggactgccag cggggcggcc tgcgccgtgc gctggcgtcg    26760
ccattcgcgc atgccggcgc tggcgtcgtt catgttgacg cgggcggcct tacgcactgc    26820
atccacggtc gggaagttct cccggtcgcc ttgctcgaac agctcgtccg cagccgcaaa    26880
aatgcggtcg cgcgtctctt tgttcagttc catgttggct ccggtaattg gtaagaataa    26940
taatactctt acctacctta tcagcgcaag agtttagctg aacagttctc gacttaacgg    27000
caggtttttt agcggctgaa gggcaggcaa aaaagccccc gcacggtcgg cgggggcaaa    27060
gggtcagcgg gaagggggatt agcgggcgtc gggcttcttc atgcgtcggg gccgcgcttc    27120
ttgggatgga gcacgacgaa gcgcgcacgc gcatcgtcct cggccctatc ggcccgcgtc    27180
gcggtcagga acttgtcgcg cgctaggtcc tccctggtgg gcaccagggg catgaactcg    27240
gcctgctcga tgtaggtcca ctccatgacc gcatcgcagt cgaggccgcg ttccttcacc    27300
gtctcttgca ggtcgcggta cgcccgctcg ttgagcggct ggtaacgggc caattggtcg    27360
taaatggctg tcggccatga gcggcctttc ctgttgagcc agcagccgac gacgaagccg    27420
gcaatgcagc ccctggcac aaccaggccg acgccggggg caggggatgg cagcagctcg    27480
ccaaccagga accccgccgc gatgatgccg atgccggtca accagcccct gaaactatcc    27540
ggccccgaaa caccctgcg cattgcctgg atgctgcgcc ggatagcttg caacatcagg    27600
agccgtttct tttgttcgtc agtcatggtc cgccctcacc agttgttcgt atcggtgtcg    27660
gacgaactga aatcgcaaga gctgccggta tcggtccagc cgctgtccgt gtcgctgctg    27720
ccgaagcacg gcgaggggtc cgcgaacgcc gcagacggcg tatccggccg cagcgcatcg    27780
cccagcatgg ccccggtcag cgagccgccg gccaggtagc ccagcatggt gctgttggtc    27840
gccccggcca ccagggccga cgtgacgaaa tcgccgtcat tccctctgga ttgttcgctg    27900
ctcggcgggg cagtgcgccg cgccggcggc gtcgtggatg gctcggggttg gctggcctgc    27960 gacggccggc gaaaggtgcg cagcagctcg ttatcgaccg gctgcggcgt cggggccgcc    28020
gccttgcgct gcggtcggtg ttccttcttc ggctcgcgca gcttgaacag catgatcgcg    28080
gaaaccagca gcaacgccgc gcctacgcct cccgcgatgt agaacagcat cggattcatt    28140
cttcggtcct ccttgtagcg gaaccgttgt ctgtgcggcg cgggtggccc gcgccgctgt    28200
cttttgggat cagccctcga tgagcgcgac cagtttcacg tcggcaaggt tcgcctcgaa    28260
ctcctggccg tcgtcctcgt acttcaacca ggcatagcct tccgccggcg gccgacggtt    28320
gaggataagg cgggcagggc gctcgtcgtg ctcgacctgg acgatggcct ttttcagctt    28380
gtccgggtcc ggctccttcg cgcccttttc cttggcgtcc ttaccgtcct ggtcgccgtc    28440
ctcgccgtcc tggccgtcgc cggcctccgc gtcacgctcg catcagtct ggccgttgaa    28500 ggcatcgacg gtgttgggat cgcggccctt tcgtccagg aactcgcgca gcagcttgac    28560
cgtgccgcgc gtgatttcct gggtgtcgtc gtcaagccac gcctcgactt cctccgggcg    28620
cttcttgaag gccgtcacca gctcgttcac cacggtcacg tcgcgcacgc ggccggtgtt    28680
gaacgcatcg gcgatcttct ccggcaggtc cagcagcgtg acgtgctggg tgatgaacgc    28740
```

```
cggcgacttg ccgatttcct tggcgatatc gcctttcttc ttgcccttcg ccagctcgcg   28800
gccaatgaag tcggcaattt cgcgcggggt cagctcgttg cgttgcaggt tctcgataac   28860
ctggtcggct tcgttgtagt cgttgtcgat gaacgccggg atggacttct tgccggccca   28920
cttcgagcca cggtagcggc gggcgccgtg attgatgata tagcggcccg gctgctcctg   28980
gttctcgcgc accgaaatgg gtgacttcac cccgcgctct ttgatcgtgg caccgatttc   29040
cgcgatgctc tccggggaaa agccggggtt gtcggccgtc cgcggctgat gcggatcttc   29100
gtcgatcagg tccaggtcca gctcgatagg gccggaaccg ccctgagacg ccgcaggagc   29160
gtccaggagg ctcgacaggt cgccgatgct atccaacccc aggccggacg gctgcgccgc   29220
gcctgcggct tcctgagcgg ccgcagcggt gttttcttg gtggtcttgg cttgagccgc   29280
agtcattggg aaatctccat cttcgtgaac acgtaatcag ccagggcgcg aacctctttc   29340
gatgccttgc gcgcggccgt tttcttgatc ttccagaccg gcacaccgga tgcgagggca   29400
tcggcgatgc tgctgcgcag gccaacggtg gccggaatca tcatcttggg gtacgcggcc   29460
agcagctcgg cttggtggcg cgcgtggcgc ggattccgcg catcgacctt gctgggcacc   29520
atgccaagga attgcagctt ggcgttcttc tggcgcacgt tcgcaatggt cgtgaccatc   29580
ttcttgatgc cctggatgct gtacgcctca agctcgatgg gggacagcac atagtcggcc   29640
gcgaagaggg cggccgccag gccgacgcca agggtcgggg ccgtgtcgat caggcacacg   29700
tcgaagcctt ggttcgccag ggccttgatg ttcgccccga acagctcgcg ggcgtcgtcc   29760
agcgacagcc gttcggcgtt cgccagtacc gggttggact cgatgagggc gaggcgcgcg   29820
gcctggccgt cgccggctgc gggtgcggtt tcggtccagc cgccggcagg gacagcgccg   29880
aacagcttgc ttgcatgcag gccggtagca aagtccttga gcgtgtagga cgcattgccc   29940
tgggggtcca ggtcgatcac ggcaacccgc aagccgcgct cgaaaaagtc gaaggcaaga   30000
tgcacaaggg tcgaagtctt gccgacgccg ccttctggt tggccgtgac caaagttttc   30060
atcgtttggt ttcctgtttt tcttggcgt ccgcttccca cttccggacg atgtacgcct   30120
gatgttccgg cagaaccgcc gttacccgcg cgtacccctc gggcaagttc ttgtcctcga   30180
acgcggccca cacgcgatgc accgcttgcg acactgcgcc cctggtcagt cccagcgacg   30240
ttgcgaacgt cgcctgtggc ttcccatcga ctaagacgcc ccgcgctatc tcgatggtct   30300
gctgccccac ttccagcccc tggatcgcct cctggaactg gctttcggta agccgttct   30360
tcatggataa cacccataat ttgctccgcg ccttggttga acatagcggt gacagccgcc   30420
agcacatgag agaagtttag ctaaacattt ctcgcacgtc aacaccttta gccgctaaaa   30480
ctcgtccttg gcgtaacaaa acaaaagccc ggaaaccggg ctttcgtctc ttgccgctta   30540
tggctctgca cccggctcca tcaccaacag gtcgcgcacg cgcttcactc ggttgcggat   30600
cgacactgcc agcccaacaa agccggttgc cgccgccgcc aggatcgcgc cgatgatgcc   30660
ggccacaccg gccatcgccc accaggtcgc cgccttccgg ttccattcct gctggtactg   30720
cttcgcaatg ctggacctcg gctcaccata ggctgaccgc tcgatggcgt atgccgcttc   30780
tccccttggc gtaaaaccca cgccgcagg cggcattgcc atgctgcccg ccgctttccc   30840
gaccacgacg cgcgcaccag gcttgcggtc cagaccttcg ccacggcga gctgcgcaag   30900
gacataatca gccgccgact tggctccacg cgcctcgatc agctcttgca ctcgcgcgaa   30960
atccttggcc tccacggccg ccatgaatcg cgcacgcggc gaaggctccg cagggccggc   31020
gtcgtgatcg ccgccgagaa tgcccttcac caagttcgac gacacgaaaa tcatgctgac   31080
```

```
ggctatcacc atcatgcaga cggatcgcac gaacccgctg aattgaacac gagcacggca   31140
cccgcgacca ctatgccaag aatgcccaag gtaaaaattg ccggccccgc catgaagtcc   31200
gtgaatgccc cgacggccga agtgaagggc aggccgccac ccaggccgcc gccctcactg   31260
cccggcacct ggtcgctgaa tgtcgatgcc agcacctgcg gcacgtcaat gcttccgggc   31320
gtcgcgctcg ggctgatcgc ccatcccgtt actgccccga tcccggcaat ggcaaggact   31380
gccagcgctg ccattttttgg ggtgaggccg ttcgcggccg aggggcgcag cccctggggg   31440
gatgggaggc ccgcgttagc gggccgggag ggttcgagaa gggggggcac ccccccttcgg   31500 cgtgcgcggt cacgcgcaca gggcgcagcc ctggttaaaa acaaggttta taaatattgg   31560
tttaaaagca ggttaaaaga caggttagcg gtggccgaaa acgggcgga aaccccttgca   31620 aatgctggat tttctgcctg tggacagccc ctcaaatgtc aataggtgcg cccctcatct   31680
gtcagcactc tgcccctcaa gtgtcaagga tcgcgcccct catctgtcag tagtcgcgcc   31740
cctcaagtgt caataccgca gggcacttat ccccaggctt gtccacatca tctgtgggaa   31800
actcgcgtaa aatcaggcgt tttcgccgat ttgcgaggct ggccagctcc acgtcgccgg   31860
ccgaaatcga gcctgcccct catctgtcaa cgccgcgccg ggtgagtcgg cccctcaagt   31920
gtcaacgtcc gccctcatc tgtcagtgag gccaagttt tccgcgaggt atccacaacg   31980
ccggcggccg cggtgtctcg cacacggctt cgacggcgtt tctggcgcgt ttgcagggcc   32040
atagacggcc gccagcccag cggcgagggc aaccagcccg gtgagcgtcg gaaaggcgct   32100
ggaagccccg tagcgacgcg gagaggggcg agacaagcca agggcgcagg ctcgatgcgc   32160
agcacgacat agccggttct cgcaaggacg agaatttccc tgcggtgccc ctcaagtgtc   32220
aatgaaagtt ccaacgcga gccattcgcg agagccttga gtccacgcta gatgagagct   32280
ttgttgtagg tggaccagtt ggtgattttg aacttttgct ttgccacgga acggtctgcg   32340
ttgtcgggaa gatgcgtgat ctgatccttc aactcagcaa aagttcgatt tattcaacaa   32400
agccacgttg tgtctcaaaa tctctgatgt tacattgcac aagataaaaa tatatcatca   32460
tgaacaataa aactgtctgc ttacataaac agtaatacaa ggggtgttat gagccatatt   32520
caacgggaaa cgtcttgctc gactctagag ctcgttcctc gaggcctcga ggcctcgagg   32580
aacggtacct gcgggaagc ttacaataat gtgtgttgtt aagtcttgtt gcctgtcatc   32640
gtctgactga ctttcgtcat aaatcccggc ctccgtaacc cagctttggg caagctcacg   32700
gatttgatcc ggcggaacgg gaatatcgag atgccgggct gaacgctgca gttccagctt   32760 tcccctttcgg gacaggtact ccagctgatt gattatctgc tgaagggtct tggttccacc   32820
tcctggcaca atgcgaatga ttacttgagc gcgatcgggc atccaattttt ctcccgtcag   32880 gtgcgtggtc aagtgctaca aggcacctttt cagtaacgag cgaccgtcga tccgtcgccg   32940
ggatacggac aaaatggagc gcagtagtcc atcgagggcg gcgaaagcct cgccaaaagc   33000
aatacgttca tctcgcacag cctccagatc cgatcgaggg tcttcggcgt aggcagatag   33060
aagcatggat acattgcttg agagtattcc gatggactga agtatggctt ccatcttttc   33120
tcgtgtgtct gcatctatttt cgagaaagcc cccgatgcgg cgcaccgcaa cgcgaattgc   33180
catactatcc gaaagtccca gcaggcgcgc ttgataggaa aaggtttcat actcggccga   33240
tcgcagacgg gcactcacga ccttgaaccc ttcaactttc agggatcgat gctggttgat   33300
ggtagtctca ctcgacgtgg ctctggtgtg ttttgacata gcttcctcca aagaaagcgg   33360
aaggtctgga tactccagca cgaaatgtgc ccgggtagac ggatggaagt ctagccctgc   33420
tcaatatgaa atcaacagta catttacagt caatactgaa tatacttgct acatttgcaa   33480
```

```
ttgtcttata acgaatgtga aataaaaata gtgtaacaac gcttttactc atcgataatc    33540
acaaaaacat ttatacgaac aaaaatacaa atgcactccg gtttcacagg ataggcggga    33600
tcagaatatg caacttttga cgttttgttc tttcaaaggg ggtgctggca aaaccaccgc    33660
actcatgggc ctttgcgctg ctttggcaaa tgacggtaaa cgagtggccc tctttgatgc    33720
cgacgaaaac cggcctctga cgcgatggag agaaaacgcc ttacaaagca gtactgggat    33780
cctcgctgtg aagtctattc cgccgacgaa atgcccttc ttgaagcagc ctatgaaaat     33840
gccgagctcg aaggatttga ttatgcgttg gccgatacgc gtggcggctc gagcgagctc    33900
aacaacacaa tcatcgctag ctcaaacctg cttctgatcc ccaccatgct aacgccgctc    33960
gacatcgatg aggcactatc tacctaccgc tacgtcatcg agctgctgtt gagtgaaaat    34020
ttggcaattc ctacagctgt tttgcgccaa cgcgtcccgg tcggccgatt gacaacatcg    34080
caacgcagga tgtcagagac gctagagagc cttccagttg taccgtctcc catgcatgaa    34140
agagatgcat ttgccgcgat gaaagaacgc ggcatgttgc atcttacatt actaaacacg    34200
ggaactgatc cgacgatgcg cctcatagag aggaatcttc ggattgcgat ggaggaagtc    34260
gtggtcattt cgaaactgat cagcaaaatc ttggaggctt gaagatggca attcgcaagc    34320
ccgcattgtc ggtcggcgaa gcacggcggc ttgctggtgc tcgacccgag atccaccatc    34380
ccaacccgac acttgttccc cagaagctgg acctccagca cttgcctgaa aaagccgacg    34440
agaaagacca gcaacgtgag cctctcgtcg ccgatcacat ttacagtccc gatcgacaac    34500
ttaagctaac tgtggatgcc cttagtccac ctccgtcccc gaaaaagctc caggtttttc    34560
tttcagcgcg accgccgcg cctcaagtgt cgaaaacata tgacaacctc gttcggcaat     34620
acagtccctc gaagtcgcta caaatgattt taaggcgcgc gttggacgat ttcgaaagca    34680
tgctggcaga tggatcattt cgcgtggccc cgaaaagtta tccgatccct tcaactacag    34740
aaaaaatccgt tctcgttcag acctcacgca tgttcccgt tgcgttgctc gaggtcgctc     34800
gaagtcattt tgatccgttg gggttggaga ccgctcgagc tttcggccac aagctggcta    34860
ccgccgcgct cgcgtcattc tttgctggag agaagccatc gagcaattgg tgaagaggga    34920
cctatcggaa cccctcacca aatattgagt gtaggtttga ggccgctggc cgcgtcctca    34980
gtcacctttt gagccagata attaagagcc aaatgcaatt ggctcaggct gccatcgtcc    35040
ccccgtgcga aacctgcacg tccgcgtcaa agaaataacc ggcacctctt gctgttttta    35100
tcagttgagg gcttgacgga tccgcctcaa gtttgcggcg cagccgcaaa atgagaacat    35160
ctatactcct gtcgtaaacc tcctcgtcgc gtactcgact ggcaatgaga agttgctcgc    35220
gcgatagaac gtcgcggggt ttctctaaaa acgcgaggag aagattgaac tcacctgccg    35280
taagtttcac ctcaccgcca gcttcggaca tcaagcgacg ttgcctgaga ttaagtgtcc    35340
agtcagtaaa acaaaaagac cgtcggtctt tggagcggac aacgttgggg cgcacgcgca    35400
aggcaacccg aatgcgtgca agaaactctc tcgtactaaa cggcttagcg ataaaatcac    35460
ttgctcctag ctcgagtgca acaactttat ccgtctcctc aaggcggtcg ccactgataa    35520
ttatgattgg aatatcagac tttgccgcca gatttcgaac gatctcaagc ccatcttcac    35580
gacctaaatt tagatcaaca accacgacat cgaccgtcgc ggaagagagt actctagtga    35640
actgggtgct gtcggctacc gcggtcactt tgaaggcgtg gatcgtaagg tattcgataa    35700
taagatgccg catagcgaca tcgtcatcga taagaagaac gtgtttcaac ggctcacctt    35760
tcaatctaaa atctgaaccc ttgttcacag cgcttgagaa attttcacgt gaaggatgta    35820
```

```
caatcatctc cagctaaatg gcagttcgt cagaattgcg gctgaccgcg gatgacgaaa    35880
atgcgaacca agtatttcaa ttttatgaca aaagttctca atcgttgtta caagtgaaac    35940
gcttcgaggt tacagctact attgattaag gagatcgcct atggtctcgc cccggcgtcg    36000
tgcgtccgcc gcgagccaga tctcgcctac ttcataaacg tcctcatagg cacgaatgg    36060 aatgatgaca tcgatcgccg tagagagcat gtcaatcagt gtgcgatctt ccaagctagc    36120
accttgggcg ctacttttga caagggaaaa cagtttcttg aatccttgga ttggattcgc    36180
gccgtgtatt gttgaaatcg atcccggatg tcccgagacg acttcactca gataagccca    36240
tgctgcatcg tcgcgcatct cgccaagcaa tatccggtcc ggccgcatac gcagacttgc    36300
ttggagcaag tgctcggcgc tcacagcacc cagcccagca ccgttcttgg agtagagtag    36360
tctaacatga ttatcgtgtg gaatgacgag ttcgagcgta tcttctatgg tgattagcct    36420
ttcctggggg gggatggcgc tgatcaaggt cttgctcatt gttgtcttgc cgcttccggt    36480
agggccacat agcaacatcg tcagtcggct gacgacgcat gcgtgcagaa acgcttccaa    36540
atccccgttg tcaaaatgct gaaggatagc ttcatcatcc tgattttggc gtttccttcg    36600
tgtctgccac tggttccacc tcgaagcatc ataacgggag gagacttctt taagaccaga    36660
aacacgcgag cttggccgtc gaatggtcaa gctgacggtg cccgagggaa cggtcggcgg    36720
cagacagatt tgtagtcgtt caccaccagg aagttcagtg gcgcagaggg ggttacgtgg    36780
tccgacatcc tgctttctca gcgcgcccgc taaaatagcg atatcttcaa gatcatcata    36840
agagacgggc aaaggcatct tggtaaaaat gccggcttgg cgcacaaatg cctctccagg    36900
tcgattgatc gcaatttctt cagtcttcgg gtcatcgagc cattccaaaa tcggcttcag    36960
aagaaagcgt agttgcggat ccacttccat ttacaatgta tcctatctct aagcggaaat    37020
ttgaattcat taagagcggc ggttcctccc ccgcgtggcg ccgccagtca ggcggagctg    37080
gtaaacacca agaaatcga ggtcccgtgc tacgaaaatg gaaacggtgt caccctgatt    37140
cttcttcagg gttggcggta tgttgatggt tgccttaagg gctgtctcag ttgtctgctc    37200
accgttattt tgaaagctgt tgaagctcat cccgccaccc gagctgccgg cgtaggtgct    37260
agctgcctgg aaggcgcctt gaacaacact caagagcata gctccgctaa aacgctgcca    37320
gaagtggctg tcgaccgagc ccggcaatcc tgagcgaccg agttcgtccg cgcttggcga    37380
tgttaacgag atcatcgcat ggtcaggtgt ctcggcgcga tcccacaaca caaaaacgcg    37440
cccatctccc tgttgcaagc cacgctgtat ttcgccaaca acggtggtgc cacgatcaag    37500
aagcacgata ttgttcgttg ttccacgaat atcctgaggc aagacacact ttacatagcc    37560
tgccaaattt gtgtcgattg cggtttgcaa gatgcacgga attattgtcc cttgcgttac    37620
cataaaatcg gggtgcggca agagcgtggc gctgctgggc tgcagctcgg tgggtttcat    37680
acgtatcgac aaatcgttct cgccggacac ttcgccattc ggcaaggagt tgtcgtcacg    37740
cttgccttct tgtcttcggc ccgtgtcgcc ctgaatggcg cgtttgctga ccccttgatc    37800
gccgctgcta tatgcaaaaa tcggtgtttc ttccggccgt ggctcatgcc gctccggttc    37860
gcccctcggc ggtagaggag cagcaggctg aacagcctct tgaaccgctg gaggatccgg    37920
cggcacctca atcggagctg gatgaaatgg cttggtgttt gttgcgatca agttgacgg    37980 cgatgcgttc tcattcacct tcttttggcg cccacctagc caaatgaggc ttaatgataa    38040
cgcgagaacg acacctccga cgatcaattt ctgagacccc gaaagacgcc ggcgatgttt    38100
gtcggagacc agggatccag atgcatcaac ctcatgtgcc gcttgctgac tatcgttatt    38160
catcccttcg cccccttcag gacgcgtttc acatcgggcc tcaccgtgcc cgtttgcggc    38220
```

```
ctttggccaa cgggatcgta agcggtgttc cagatacata gtactgtgtg gccatccctc   38280
agacgccaac ctcgggaaac cgaagaaatc tcgacatcgc tccctttaac tgaatagttg   38340
gcaacagctt ccttgccatc aggattgatg gtgtagatgg agggtatgcg tacattgccc   38400
ggaaagtgga ataccgtcgt aaatccattg tcgaagactt cgagtggcaa cagcgaacga   38460
tcgccttggg cgacgtagtg ccaattactg tccgccgcac caagggctgt gacaggctga   38520
tccaataaat tctcagcttt ccgttgatat tgtgcttccg cgtgtagtct gtccacaaca   38580
gccttctgtt gtgcctccct tcgccgagcc gccgcatcgt cggcggggta ggcgaattgg   38640
acgctgtaat agagatcggg ctgctcttta tcgaggtggg acagagtctt ggaacttata   38700
ctgaaaacat aacggcgcat cccggagtcg cttgcggtta gcacgattac tggctgaggc   38760
gtgaggacct ggcttgcctt gaaaaataga taatttcccc gcggtagggc tgctagatct   38820
ttgctatttg aaacggcaac cgctgtcacc gtttcgttcg tggcgaatgt tacgaccaaa   38880
gtagctccaa ccgccgtcga gaggcgcacc acttgatcgg gattgtaagc caaataacgc   38940
atgcgcggat ctagcttgcc cgccattgga gtgtcttcag cctccgcacc agtcgcagcg   39000
gcaaataaac atgctaaaat gaaaagtgct tttctgatca tggttcgctg tggcctacgt   39060
ttgaaacggt atcttccgat gtctgatagg aggtgacaac cagacctgcc gggttggtta   39120
gtctcaatct gccgggcaag ctggtcacct tttcgtagcg aactgtcgcg gtccacgtac   39180
tcaccacagg cattttgccg tcaacgacga gggtcctttt atagcgaatt tgctgcgtgc   39240
ttggagttac atcatttgaa gcgatgtgct cgacctccac cctgccgcgt ttgccaagaa   39300
tgacttgagg cgaactggga ttgggatagt tgaagaattg ctggtaatcc tggcgcactg   39360
ttggggcact gaagttcgat accaggtcgt aggcgtactg agcggtgtcg gcatcataac   39420
tctcgcgcag gcgaacgtac tcccacaatg aggcgttaac gacggcctcc tcttgagttg   39480
caggcaatcg cgagacagac acctcgctgt caacggtgcc gtccggccgt atccatagat   39540
atacgggcac aagcctgctc aacggcacca ttgtggctat agcgaacgct tgagcaacat   39600
ttcccaaaat cgcgatagct gcgacagctg caatgagttt ggagagacgt cgcgccgatt   39660
tcgctcgcgc ggtttgaaag gcttctactt ccttatagtg ctcggcaagg ctttcgcgcg   39720
ccactagcat ggcatattca ggccccgtca tagcgtccac ccgaattgcc gagctgaaga   39780
tctgacggag taggctgcca tcgccccaca ttcagcggga agatcgggcc tttgcagctc   39840
gctaatgtgt cgtttgtctg gcagccgctc aaagcgacaa ctaggcacag caggcaatac   39900
ttcatagaat tctccattga ggcgaatttt tgcgcgacct agcctcgctc aacctgagcg   39960
aagcgacggt acaagctgct ggcagattgg gttgcgccgc tccagtaact gcctccaatg   40020
ttgccggcga tcgccggcaa agcgacaatg agcgcatccc ctgtcagaaa aaacatatcg   40080
agttcgtaaa gaccaatgat cttggccgcg gtcgtaccgg cgaaggtgat tacaccaagc   40140
ataagggtga gcgcagtcgc ttcggttagg atgacgatcg ttgccacgag gtttaagagg   40200
agaagcaaga gaccgtaggt gataagttgc ccgatccact tagctgcgat gtcccgcgtg   40260
cgatcaaaaa tatatccgac gaggatcaga ggcccgatcg cgagaagcac tttcgtgaga   40320
attccaacgg cgtcgtaaac tccgaaggca gaccagagcg tgccgtaaag gacccactgt   40380 gcccccttgga aagcaaggat gtcctggtcg ttcatcggac cgatttcgga tgcgattttc   40440
tgaaaaacgg cctgggtcac ggcgaacatt gtatccaact gtgccggaac agtctgcaga   40500
ggcaagccgg ttacactaaa ctgctgaaca aagtttggga ccgtcttttc gaagatggaa   40560
```

```
accacatagt cttggtagtt agcctgccca acaattagag caacaacgat ggtgaccgtg   40620
atcacccgag tgataccgct acgggtatcg acttcgccgc gtatgactaa aatacectga   40680
acaataatcc aaagagtgac acaggcgatc aatggcgcac tcaccgcctc ctggatagtc   40740
tcaagcatca gtccaagcc tgtcgtgaag gctacatcga agatcgtatg aatggccgta    40800
aacggcgccg gaatcgtgaa attcatcgat tggacctgaa cttgactggt ttgtcgcata   40860
atgttggata aaatgagctc gcattcggcg aggatgcggg cggatgaaca aatcgcccag   40920
ccttagggga gggcaccaaa gatgacagcg gtcttttgat gctccttgcg ttgagcggcc   40980
gcctcttccg cctcgtgaag gccggcctgc gcggtagtca tcgttaatag gcttgtcgcc   41040
tgtacatttt gaatcattgc gtcatggatc tgcttgagaa gcaaaccatt ggtcacggtt   41100
gcctgcatga tattgcgaga tcgggaaagc tgagcagacg tatcagcatt cgccgtcaag   41160
cgtttgtcca tcgtttccag attgtcagcc gcaatgccag cgctgtttgc ggaaccggtg   41220
atctgcgatc gcaacaggtc cgcttcagca tcactaccca cgactgcacg atctgtatcg   41280
ctggtgatcg cacgtgccgt ggtcgacatt ggcattcgcg gcgaaaacat ttcattgtct   41340
aggtccttcg tcgaaggata ctgattttc tggttgagcg aagtcagtag tccagtaacg    41400
ccgtaggccg acgtcaacat cgtaaccatc gctatagtct gagtgagatt ctccgcagtc   41460
gcgagcgcag tcgcgagcgt ctcagcctcc gttgccgggt cgctaacaac aaactgcgcc   41520
cgcgcgggct gaatatatag aaagctgcag gtcaaaactg ttgcaataag ttgcgtcgtc   41580
ttcatcgttt cctaccttat caatcttctg cctcgtggtg acgggccatg aattcgctga   41640
gccagccaga tgagttgcct tcttgtgcct cgcgtagtcg agttgcaaag cgcaccgtgt   41700
tggcacgccc cgaaagcacg gcgacatatt cacgcatatc ccgcagatca aattcgcaga   41760
tgacgcttcc actttctcgt ttaagaagaa acttacggct gccgaccgtc atgtcttcac   41820
ggatcgcctg aaattccttt tcggtacatt tcagtccatc gacataagcc gatcgatctg   41880
cggttggtga tggatagaaa atcttcgtca tacattgcgc aaccaagctg gctcctagcg   41940
gcgattccag aacatgctct ggttgctgcg ttgccagtat tagcatcccg ttgttttttc   42000
gaacggtcag gaggaatttg tcgacgacag tcgaaaattt agggtttaac aaataggcgc   42060
gaaactcatc gcagctcatc acaaaacggc ggccgtcgat catggctcca atccgatgca   42120
ggagatatgc tgcagcggga gcgcatactt cctcgtattc gagaagatgc gtcatgtcga   42180
agccggtaat cgacggatct aactttactt cgtcaacttc gccgtcaaat gcccagccaa   42240
gcgcatggcc ccggcaccag cgttggagcc gcgctcctgc gccttcggcg ggcccatgca   42300
acaaaaattc acgtaacccc gcgattgaac gcatttgtgg atcaaacgag agctgacgat   42360
ggataccacg gaccagacgg cggttctctt ccggagaaat cccacccga ccatcactct    42420
cgatgagagc cacgatccat tcgcgcagaa aatcgtgtga ggctgctgtg ttttctaggc   42480
cacgcaacgg cgccaacccg ctgggtgtgc ctctgtgaag tgccaaatat gttcctcctg   42540
tggcgcgaac cagcaattcg ccaccccggt ccttgtcaaa gaacacgacc gtacctgcac   42600
ggtcgaccat gctctgttcg agcatggcta gaacaaacat catgagcgtc gtcttacccc   42660
tcccgatagg cccgaatatt gccgtcatgc caacatcgtg ctcatgcggg atatagtcga   42720
aaggcgttcc gccattggta cgaaatcggg caatcgcgtt gccccagtgg cctgagctgg   42780
cgccctctgg aaagttttcg aaagagacaa accctgcgaa attgcgtgaa gtgattgcgc   42840
cagggcgtgt gcgccactta aaattccccg gcaattggga ccaataggcc gcttccatac   42900
caataccttc ttggacaacc acggcacctg catccgccat tcgtgtccga gccgcgcgc    42960
```

```
ccctgtcccc aagactattg agatcgtctg catagacgca aaggctcaaa tgatgtgagc    43020
ccataacgaa ttcgttgctc gcaagtgcgt cctcagcctc ggataatttg ccgatttgag    43080
tcacggcttt atcgccggaa ctcagcatct ggctcgattt gaggctaagt ttcgcgtgcg    43140
cttgcgggcg agtcaggaac gaaaaactct gcgtgagaac aagtggaaaa tcgagggata    43200
gcagcgcgtt gagcatgccc ggccgtgttt ttgcagggta ttcgcgaaac gaatagatgg    43260
atccaacgta actgtctttt ggcgttctga tctcgagtcc tcgcttgccg caaatgactc    43320
tgtcggtata aatcgaagcg ccgagtgagc cgctgacgac cggaaccggt gtgaaccgac    43380
cagtcatgat caaccgtagc gcttcgccaa tttcggtgaa gagcacaccc tgcttctcgc    43440
ggatgccaag acgatgcagg ccatacgctt aagagagcc agcgacaaca tgccaaagat    43500
cttccatgtt cctgatctgg cccgtgagat cgtttcccct ttttccgctt agcttggtga    43560
acctcctctt taccttccct aaagccgcct gtgggtagac aatcaacgta aggaagtgtt    43620
cattgcggag gagttggccg gagagcacgc gctgttcaaa agcttcgttc aggctagcgg    43680
cgaaaacact acggaagtgt cgcggcgccg atgatggcac gtcggcatga cgtacgaggt    43740
gagcatatat tgacacatga tcatcagcga tattgcgcaa cagcgtgttg aacgcacgac    43800
aacgcgcatt gcgcatttca gtttcctcaa gctcgaatgc aacgccatca attctcgcaa    43860
tggtcatgat cgatccgtct tcaagaagga cgatatggtc gctgaggtgg ccaatataag    43920
ggagatagat ctcaccggat cttcggtcg ttccactcgc gccgagcatc acaccattcc    43980
tctccctcgt gggggaaccc taattggatt tgggctaaca gtagcgcccc cccaaactgc    44040
actatcaatg cttcttcccg cggtccgcaa aaatagcagg acgacgctcg ccgcattgta    44100
gtctcgctcc acgatgagcc gggctgcaaa ccataacggc acgagaacga cttcgtagag    44160
cgggttctga acgataacga tgacaaagcc ggcgaacatc atgaataacc ctgccaatgt    44220
cagtggcacc ccaagaaaca atgcgggccg tgtggctgcg aggtaaaggg tcgattcttc    44280
caaacgatca gccatcaact accgccagtg agcgtttggc cgaggaagct cgccccaaac    44340
atgataacaa tgccgccgac gacgccggca accagcccaa gcgaagcccg cccgaacatc    44400
caggagatcc cgatagcgac aatgccgaga acagcgagtg actggccgaa cggaccaagg    44460
ataaacgtgc atatattgtt aaccattgtg gcggggtcag tgccgccacc cgcagattgc    44520
gctgcggcgg gtccggatga ggaaatgctc catgcaattg caccgcacaa gcttggggcg    44580
cagctcgata tcacgcgcat catcgcattc gagagcgaga ggcgatttag atgtaaacgg    44640
tatctctcaa agcatcgcat caatgcgcac ctccttagta taagtcgaat aagacttgat    44700
tgtcgtctgc ggatttgccg ttgtcctggt gtggcggtgg cggagcgatt aaaccgccag    44760
cgccatcctc ctgcgagcgg cgctgatatg accccaaac atcccacgtc tcttcggatt    44820
ttagcgcctc gtgatcgtct tttggaggct cgattaacgc gggcaccagc gattgagcag    44880
ctgtttcaac ttttcgcacg tagccgtttg caaaaccgcc gatgaaatta ccggtgttgt    44940
aagcggagat cgcccgacga agcgcaaatt gcttctcgtc aatcgtttcg ccgcctgcat    45000
aacgactttt cagcatgttt gcagcggcag ataatgatgt gcacgcctgg agcgcaccgt    45060
caggtgtcag accgagcata gaaaaatttc gagagtttat ttgcatgagg ccaacatcca    45120
gcgaatgccg tgcatcgaga cggtgcctga cgacttgggt tgcttggctg tgatcttgcc    45180
agtgaagcgt ttcgccggtc gtgttgtcat gaatcgctaa aggatcaaag cgactctcca    45240
ccttagctat cgccgcaagc gtagatgtcg caactgatgg ggcacacttg cgagcaacat    45300
```

```
ggtcaaactc agcagatgag agtggcgtgg caaggctcga cgaacagaag gagaccatca    45360
aggcaagaga aagcgacccc gatctcttaa gcataccttg tctccttagc tcgcaactaa    45420
caccgcctct cccgttggaa gaagtgcgtt gttttatgtt gaagattatc gggagggtcg    45480
gttactcgaa aattttcaat tgcttcttta tgatttcaat tgaagcgaga aacctcgccc    45540
ggcgtcttgg aacgcaacat ggaccgagaa ccgcgcatcc atgactaagc aaccggatcg    45600
acctattcag gccgcagttg gtcaggtcag gctcagaacg aaaatgctcg gcgaggttac    45660
gctgtctgta aacccattcg atgaacggga agcttccttc cgattgctct tggcaggaat    45720
attggcccat gcctgcttgc gctttgcaaa tgctcttatc gcgttggtat catatgcctt    45780
gtccgccagc agaaacgcac tctaagcgat tatttgtaaa aatgtttcgg tcatgcggcg    45840
gtcatgggct tgacccgctg tcagcgcaag acggatcggt caaccgtcgg catcgacaac    45900
agcgtgaatc ttggtggtca aaccgccacg ggaacgtccc atacagccat cgtcttgatc    45960
ccgctgtttc ccgtcgccgc atgttggtgg acgcggacac aggaactgtc aatcatgacg    46020
acattctatc gaaagccttg gaaatcacac tcagaatatg atcccagacg tctgcctcac    46080
gccatcgtac aaagcgattg tagcaggttg tacaggaacc gtatcgatca ggaacgtctg    46140
cccagggcgg gcccgtccgg aagcgccaca agatgacatt gatcacccgc gtcaacgcgc    46200
ggcacgcgac gcggcttatt tgggaacaaa ggactgaaca acagtccatt cgaaatcggt    46260
gacatcaaag cggggacggg ttatcagtgg cctccaagtc aagcctcaat gaatcaaaat    46320
cagaccgatt tgcaaacctg atttatgagt gtgcggccta aatgatgaaa tcgtccttct    46380
agatcgcctc cgtggtgtag caacacctcg cagtatcgcc gtgctgacct tggccaggga    46440
attgactggc aagggtgctt tcacatgacc gctctttttgg ccgcgataga tgatttcgtt    46500
gctgctttgg gcacgtagaa ggagagaagt catatcggag aaattcctcc tggcgcgaga    46560
gcctgctcta tcgcgacggc atcccactgt cgggaacaga ccggatcatt cacgaggcga    46620
aagtcgtcaa cacatgcgtt ataggcatct tcccttgaag gatgatcttg ttgctgccaa    46680
tctggaggtg cggcagccgc aggcagatgc gatctcagcg caacttgcgg caaaacatct    46740
cactcacctg aaaaccacta gcgagtctcg cgatcagacg aaggccttttt acttaacgac    46800 acaatatccg atgtctgcat cacaggcgtc gctatcccag tcaatactaa agcggtgcag    46860
gaactaaaga ttactgatga cttaggcgtg ccacgaggcc tgagacgacg cgcgtagaca    46920
gttttttgaa atcattatca aagtgatggc ctccgctgaa gcctatcacc tctgcgccgg    46980
tctgtcggag agatgggcaa gcattattac ggtcttcgcg cccgtacatg cattggacga    47040
ttgcagggtc aatggatctg agatcatcca gaggattgcc gcccttacct tccgtttcga    47100
gttggagcca gcccctaaat gagacgacat agtcgacttg atgtgacaat gccaagagag    47160
agatttgctt aacccgattt ttttgctcaa gcgtaagcct attgaagctt gccggcatga    47220
cgtccgcgcc gaaagaatat cctacaagta aacattctg cacaccgaaa tgcttggtgt    47280
agacatcgat tatgtgacca agatccttag cagtttcgct tggggaccgc tccgaccaga    47340
aataccgaag tgaactgacg ccaatgacag gaatcccttc cgtctgcaga taggtaccat    47400
cgatagatct gctgcctcgc gcgtttcggt gatgacggtg aaaacctctg acacatgcag    47460 ctccccggaga cggtcacagc ttgtctgtaa gcggatgccg ggagcagaca agcccgtcag    47520
ggcgcgtcag cgggtgttgg cgggtgtcgg ggcgcagcca tgacccagtc acgtagcgat    47580
agcggagtgt atactggctt aactatgcgg catcagagca gattgtactg agagtgcacc    47640
atatgcggtg tgaaataccg cacagatgcg taaggagaaa ataccgcatc aggcgctctt    47700
```

```
ccgcttcctc gctcactgac tcgctgcgct cggtcgttcg gctgcggcga gcggtatcag    47760
ctcactcaaa ggcggtaata cggttatcca cagaatcagg ggataacgca ggaaagaaca    47820
tgtgagcaaa aggccagcaa aaggccagga accgtaaaaa ggccgcgttg ctggcgtttt    47880
tccataggct ccgcccccct gacgagcatc acaaaaatcg acgctcaagt cagaggtggc    47940
gaaacccgac aggactataa agataccagg cgtttccccc tggaagctcc ctcgtgcgct    48000
ctcctgttcc gaccctgccg cttaccggat acctgtccgc ctttctccct tcgggaagcg    48060
tggcgctttc tcatagctca cgctgtaggt atctcagttc ggtgtaggtc gttcgctcca    48120
agctgggctg tgtgcacgaa ccccccgttc agcccgaccg ctgcgcctta tccggtaact    48180
atcgtcttga gtccaacccg gtaagacacg acttatcgcc actggcagca gccactggta    48240
acaggattag cagagcgagg tatgtaggcg gtgctacaga gttcttgaag tggtggccta    48300
actacggcta cactagaagg acagtatttg gtatctgcgc tctgctgaag ccagttacct    48360
tcggaaaaag agttggtagc tcttgatccg gcaaacaaac caccgctggt agcggtggtt    48420
tttttgtttg caagcagcag attacgcgca gaaaaaaagg atctcaagaa gatcctttga    48480
tcttttctac ggggtctgac gctcagtgga acgaaaactc acgttaaggg attttggtca    48540
tgagattatc aaaaaggatc ttcacctaga tccttttaaa ttaaaaatga agttttaaat    48600
caatctaaag tatatatgag taaacttggt ctgacagtta ccaatgctta atcagtgagg    48660
cacctatctc agcgatctgt ctatttcgtt catccatagt tgcctgactc cccgtcgtgt    48720
agataactac gatacgggag ggcttaccat ctggccccag tgctgcaatg ataccgcgag    48780
acccacgctc accggctcca gatttatcag caataaacca gccagccgga agggccgagc    48840
gcagaagtgg tcctgcaact ttatccgcct ccatccagtc tattaattgt tgccgggaag    48900
ctagagtaag tagttcgcca gttaatagtt tgcgcaacgt tgttgccatt gctgcagggg    48960
gggggggggg gggggacttc cattgttcat tccacggaca aaacagaga aaggaaacga    49020 cagaggccaa aaagcctcgc tttcagcacc tgtcgtttcc tttcttttca gagggtattt    49080
taaataaaaa cattaagtta tgacgaagaa gaacggaaac gccttaaacc ggaaaatttt    49140
cataaatagc gaaaacccgc gaggtcgccg ccccgtaacc tgtcggatca ccggaaagga    49200
cccgtaaagt gataatgatt atcatctaca tatcacaacg tgcgtggagg ccatcaaacc    49260
acgtcaaata atcaattatg acgcaggtat cgtattaatt gatctgcatc aacttaacgt    49320
aaaaacaact tcagacaata caaatcagcg acactgaata cggggcaacc tcatgtcccc    49380 ccccccccc cccctgcagg catcgtggtg tcacgctcgt cgtttggtat ggcttcattc    49440
agctccggtt cccaacgatc aaggcgagtt acatgatccc ccatgttgtg caaaaaagcg    49500
gttagctcct tcggtcctcc gatcgttgtc agaagtaagt tggccgcagt gttatcactc    49560
atggttatgg cagcactgca taattctctt actgtcatgc catccgtaag atgcttttct    49620
gtgactggtg agtactcaac caagtcattc tgagaatagt gtatgcggcg accgagttgc    49680
tcttgcccgg cgtcaacacg ggataatacc gcgccacata gcagaacttt aaaagtgctc    49740
atcattggaa aacgttcttc ggggcgaaaa ctctcaagga tcttaccgct gttgagatcc    49800
agttcgatgt aacccactcg tgcacccaac tgatcttcag catcttttac tttcaccagc    49860
gtttctgggt gagcaaaaac aggaaggcaa aatgccgcaa aaagggaat aagggcgaca    49920 cggaaatgtt gaatactcat actcttcctt tttcaatatt attgaagcat ttatcagggt    49980
tattgtctca tgagcggata catatttgaa tgtatttaga aaaataaaca aataggggtt    50040
```

```
ccgcgcacat ttccccgaaa agtgccacct gacgtctaag aaaccattat tatcatgaca    50100
ttaacctata aaaataggcg tatcacgagg ccctttcgtc ttcaagaatt ggtcgacgat    50160
cttgctgcgt tcggatattt tcgtggagtt cccgccacag acccggattg aaggcgagat    50220
ccagcaactc gcgccagatc atcctgtgac ggaactttgg cgcgtgatga ctggccagga    50280
cgtcggccga aagagcgaca agcagatcac gcttttcgac agcgtcggat ttgcgatcga    50340 ggattttcg cgcgctgcgct acgtccgcga ccgcgttgag ggatcaagcc acagcagccc    50400
actcgacctt ctagccgacc cagacgagcc aagggatctt tttggaatgc tgctccgtcg    50460
tcaggctttc cgacgtttgg gtggttgaac agaagtcatt atcgtacgga atgccaagca    50520
ctcccgaggg gaaccctgtg gttggcatgc acatacaaat ggacgaacgg ataaacctttt    50580 tcacgccctt ttaaatatcc gttattctaa taaacgctct tttctcttag gtttacccgc    50640
caatatatcc tgtcaaacac tgatagttta aactgaaggc gggaaacgac aatctgatca    50700
tgagcggaga attaagggag tcacgttatg acccccgccg atgacgcggg acaagccgtt    50760
ttacgtttgg aactgacaga accgcaacgt tgaaggagcc actcagcaag ctggtacgat    50820
tgtaatacga ctcactatag ggcgaattga gcgctgttta aacgctcttc aactggaaga    50880
gcggttacta ccggttaagt gactagggtc                                    50910

<210> SEQ ID NO 6
<211> LENGTH: 50751
<212> TYPE: DNA
<213> ORGANISM: Artificial Sequence
<220> FEATURE:
<223> OTHER INFORMATION: PINII terminator control vector

<400> SEQUENCE: 6
acgtgaccct agtcacttag gttaccagag ctggtcacct ttgtccacca agatggaact      60
gcggccgctc attaattaag tcaggcgcgc ctctagttga agacacgttc atgtcttcat     120
cgtaagaaga cactcagtag tcttcggcca gaatggccat ctggattcag caggcctaga     180 aggccatttta aatcctgagg atctggtctt cctaaggacc cgggatatcg ctatcaactt     240
tgtatagaaa agttgggccg aattcgagct cggtacggcc agaatggccc ggaccgggtt     300
accgaattcg agctcggtac cactagtaag cttgccgcaa ttcgcaaaac acacctagac     360
tagatttgtt ttgctaaccc aattgatatt aattatatat gattaatatt tatatgtata     420
tggatttggt taatgaaatg catctggttc atcaaagaat tataaagaca cgtgacattc     480
atttaggata agaaatatgg atgatctctt tctcttttat tcagataact agtaattaca     540
cataacacac aactttgatg cccacattat agtgattagc atgtcactat gtgtgcatcc     600 ttttattca tacattaatt aagttggcca atccagaaga tggacaagtc tggatcttca     660
ttgtttgcct ccctgctgcg gttttcacc gaagttcatg ccagtccagc gtttttgcag     720
cagaaaagcc gccgacttcg gtttgcggtc gcgagtgaag atcccttcct tgttaccgcc     780
aacgcgcaat atgccttgcg aggtcgcaaa atcggcgaaa ttccatacct gttcaccgac     840
gacggcgctg acgcgatcaa agacgcggtg atacatatcc agccatgcac actgatactc     900
ttcactccac atgtcggtgt acattgagtg cagcccggct aacgtatcca cgccgtattc     960
ggtgatgata atcggctgat gcagtttctc ctgccaggcc agaagttctt tttccagtac    1020
cttctctgcc gtttccaaat cgccgctttg gacataccat ccgtaataac ggttcaggca    1080
cagcacatca aagagatcgc taatggtatc ggtgtgagcg tcgcagaaca ttacattgac    1140
gcaggtgatc ggacgcgtcg ggtcgagttt acgcgttgct tccgccagtg gcgcgaaata    1200
```

```
ttcccgtgca ccttgcggac gggtatccgg ttcgttggca atactccaca tcaccacgct    1260
tgggtggttt ttgtcacgcg ctatcagctc tttaatcgcc tgtaagtgcg cttgctgagt    1320
ttccccgttg actgcctctt cgctgtacag ttctttcggc ttgttgcccg cttcgaaacc    1380
aatccctaaa gagaggttaa agccgacagc agcagtttca tcaatcacca cgatgccatg    1440
ttcatctgcc cagtcgagca tctcttcagc gtaagggtaa tgcgaggtac ggtaggagtt    1500
ggccccaatc cagtccatta atgcgtggtc gtgcaccatc agcacgttat cgaatccttt    1560
gccacgcaag tccgcatctt catgacgacc aaagccagta agtagaacg gtttgtggtt     1620 aatcaggaac tgttggccct tcactgccac tgaccggatg ccgacgcgaa gcgggtagat    1680
atcacactct gtctggcttt tggctgtgac gcacagttca tagagataac cttcacccgg    1740
ttgccagagt gcggattca ccacttgcaa agtcccgcta gtgccttgtc cagttgcaac      1800
cacctgttga tccgcatcac gcagttcaac gctgacatca ccattggcca ccacctgcca    1860
gtcaacagac gcgtggttac agtcttgcgc gacatgcgtc accacggtga tatcgtccac    1920
ccaggtgttc ggcgtggtgt agagcattac gctgcgatgg attccggcat agttaaagaa    1980
atcatggaag taagactgct tttcttgcc gttttcgtcg gtaatcacca ttcccggcgg      2040
gatagtctgc cagttcagtt cgttgttcac acaaacggtg atacctgcac atcaacaaat    2100
tttggtcata tattagaaaa gttataaatt aaaatataca cacttataaa ctacagaaaa    2160
gcaattgcta tatactacat tcttttattt tgaaaaaaat atttgaaata ttatattact    2220
actaattaat gataattatt atatatatat caaaggtaga agcagaaact tacgtacact    2280
tttcccggca ataacatacg gcgtgacatc ggcttcaaat ggcgtatagc cgccctgatg    2340
ctccatcact tcctgattat tgacccacac tttgccgtaa tgagtgaccg catcgaaacg    2400
cagcacgata cgctggcctg cccaaccttt cggtataaag acttcgcgct gataccagac    2460
gttgcccgca taattacgaa tatctgcatc ggcgaactga tcgttaaaac tgcctggcac    2520
agcaattgcc cggcttttctt gtaacgcgct ttccccaccaa cgctgatcaa ttccacagtt   2580
ttcgcgatcc agactgaatg cccacaggcc gtcgagtttt ttgatttcac gggttggggt    2640
ttctacagga cggaccatgg tgtcgtgtgg atccaaattg tatgcaaggt gaatgacttt    2700
cttttcgtaa actagatagg agtactcctc caggatgctt aacccgtatt gacgtacaga    2760
ggtctatgat ccttttgttt ataaggagc ttgtagttca gtcagtctta tacttcacga     2820
tgcccatgtt tctatatagg atattatctt ggctttgtaa gtacttcacg caggttatgt    2880
tctgtttcta ggatattatc ctcatacatg cgaagaacca attttccccc cattctcttc    2940 gggtacttttt tcttgggtag gcatgctctc ttggaccaac tagcataaaa cataatcatt    3000
tttccctaca gccttgacca gctataatcg aaatcatgct cattttctca agaaagactg    3060
aatacagctc caatttaaac aatttaaatc ataaacttgt aactcaatta gagaaaagca    3120
gagcccttcg gctcctatct aaaggaatta ccccatgaaa gccataaaaa cgaaccttgc    3180
tctgatacca gacgggtcta cgctcgcgga actaggatct tgcgctctac tcgcacaaag    3240
tgaactcgca caaagtgtgt ttcaagcaca gaagttttta tttctcaaat caggagtaaa    3300
ctcgcgttgt ggtgcgtgtt tgcaacctga atacaaggcc ccttatatag agagttgtgg    3360
agctttctgg catcgttagg tggcatccac caataatgca gataagcatc atcacatgtc    3420
tctggcctaa caactttgcg taagaatcct gcaaagttac taaaggtcat cgtgcgtgac    3480
tagacaacgc acaccgacaa acttaaaata aagagacatt atactttgtc tcctctttac    3540
```

```
ataaagtgag tggtatccag ctcactccgc atcttatcag tcttcacacc ggttggtatc    3600
aacacgtggt aggggtccgc cacttccgct tcagtcatca ttactgatat ccagcagatc    3660
tagagcatct tcaataagat attcttgttc tgcacgcaga ttttcttgct ccctcagtaa    3720
ttcctcccac agtgagtctt ctgatatttc ttcaagtttc ttctcccatc tgatcttttc    3780
ctgcacaaac gagtcaattt ggtctttcca gacccaagta aaacaagtgt tagtttcaca    3840
ggagtaaaac tccctgtcag gatttctgga tgttctggag atcttcagtt ttgctggttt    3900
attgcatcca catttgaaaa ccggctcttc acttagtgtt agcacattga tttgatgcaa    3960
cctgtagcct ttgctcaacc agtcttcata tctttttaca acatcattaa ctctctgttt    4020
tgcatcggtg tttcccttgt gaaataccte ctccactgca ttgatcaaca caccttcaga    4080
ttgatgcttt tccggatgga gaataatctt taccagtctt gacagagtgt ctgctaaaac    4140
gttgtccttt ccgtcaatgt gttcaaactt aatctcaaga cctgtcccgg taatgtaatc    4200
tgtgaaggca agccatctga ctcttgatgg tttatgatca ctgcttttct tgtaaaagct    4260
cactattgct tgactgtcag ttctgattat gagctctttg taagcttggt cacccggtcc    4320
gggcctagaa ggccagcttc ggccgccccg ggcaacttta ttatacaaag ttgatagata    4380
tcggaccgat taaactttaa ttcggtccga agcttgcatg cctgcagtgc agcgtgaccc    4440
ggtcgtgccc ctctctagag ataatgagca ttgcatgtct aagttataaa aaattaccac    4500 atatttttt tgtcacactt gtttgaagtg cagtttatct atcttatac atatatttaa    4560 actttactct acgaataata taatctatag tactacaata atatcagtgt tttagagaat    4620
catataaatg aacagttaga catggtctaa aggacaattg agtattttga caacaggact    4680
ctacagtttt atcttttttag tgtgcatgtg ttctcctttt tttttgcaaa tagcttcacc    4740
tatataatac ttcatccatt ttattagtac atccatttag ggtttagggt taatggtttt    4800
tatagactaa tttttttagt acatctattt tattctattt tagcctctaa attaagaaaa    4860
ctaaaactct attttagttt ttttatttaa taatttagat ataaaataga ataaaataaa    4920
gtgactaaaa attaaacaaa tacccttttaa gaaattaaaa aaactaagga aacatttttc    4980
ttgtttcgag tagataatgc cagcctgtta aacgccgtcg acgagtctaa cggacaccaa    5040
ccagcgaacc agcagcgtcg cgtcgggcca agcgaagcag acggcacggc atctctgtcg    5100
ctgcctctgg acccctctcg agagttccgc tccaccgttg gacttgctcc gctgtcggca    5160
tccagaaatt gcgtggcgga gcggcagacg tgagccggca cggcaggcgg cctcctcctc    5220
ctctcacggc accggcagct acgggggatt ccttttccac cgctccttcg ctttcccttc    5280
ctcgcccgcc gtaataaata gacaccccct ccacaccctc tttccccaac ctcgtgttgt    5340
tcggagcgca cacacacaca accagatctc ccccaaatcc acccgtcggc acctccgctt    5400
caaggtacgc cgctcgtcct ccccccccc cctctctacc ttctctagat cggcgttccg    5460
gtccatgcat ggttagggcc cggtagttct acttctgttc atgtttgtgt tagatccgtg    5520
tttgtgttag atccgtgctg ctagcgttcg tacacggatg cgacctgtac gtcagacacg    5580
ttctgattgc taacttgcca gtgtttctct ttggggaatc ctgggatggc tctagccgtt    5640
ccgcagacgg gatcgatttc atgattttt ttgtttcgtt gcatagggtt tggtttgccc    5700 ttttcctta tttcaatata tgccgtgcac ttgtttgtcg ggtcatcttt tcatgctttt    5760
ttttgtcttg gttgtgatga tgtggtctgg ttgggcggtc gttctagatc ggagtagaat    5820
tctgtttcaa actacctggt ggattttatta attttggatc tgtatgtgtg tgccatacat    5880
attcatagtt acgaattgaa gatgatggat ggaaatatcg atctaggata ggtatacatg    5940
```

```
ttgatgcggg ttttactgat gcatatacag agatgctttt tgttcgcttg gttgtgatga    6000
tgtggtgtgg ttgggcggtc gttcattcgt tctagatcgg agtagaatac tgtttcaaac    6060
tacctggtgt atttattaat tttggaactg tatgtgtgtg tcatacatct tcatagttac    6120
gagtttaaga tggatggaaa tatcgatcta ggataggtat acatgttgat gtgggtttta    6180
ctgatgcata tacatgatgg catatgcagc atctattcat atgctctaac cttgagtacc    6240
tatctattat aataaacaag tatgttttat aattattttg atcttgatat acttggatga    6300
tggcatatgc agcagctata tgtggatttt tttagccctg ccttcatacg ctatttattt    6360
gcttggtact gtttcttttg tcgatgctca ccctgttgtt tggtgttact tctgcaggtc    6420
gactttaact tagcctagga tccacacgac accatgtccc ccgagcgccg ccccgtcgag    6480
atccgcccgg ccaccgccgc cgacatggcc gccgtgtgcg acatcgtgaa ccactacatc    6540
gagacctcca ccgtgaactt ccgcaccgag ccgcagaccc gcaggagtg gatcgacgac    6600 ctggagcgcc tccaggaccg ctacccgtgg ctcgtggccg aggtggaggg cgtggtggcc    6660
ggcatcgcct acgccggccc gtggaaggcc cgcaacgcct acgactggac cgtggagtcc    6720
accgtgtacg tgtcccaccg ccaccagcgc ctcggcctcg gctccaccct ctacacccac    6780
ctcctcaaga gcatggaggc ccagggcttc aagtccgtgg tggccgtgat cggcctcccg    6840
aacgacccgt ccgtgcgcct ccacgaggcc ctcggctaca ccgcccgcgg cacccctccgc    6900 gccgccggct acaagcacgg cggctggcac gacgtcggct tctggcagcg cgacttcgag    6960
ctgccggccc cgccgcgccc ggtgcgcccg gtgacgcaga tctgagtcga aacctagact    7020
tgtccatctt ctggattggc caacttaatt aatgtatgaa ataaaaggat gcacacatag    7080
tgacatgcta atcactataa tgtgggcatc aaagttgtgt gttatgtgta attactagtt    7140
atctgaataa aagagaaaga gatcatccat atttcttatc ctaaatgaat gtcacgtgtc    7200
tttataattc tttgatgaac cagatgcatt tcattaacca aatccatata catataaata    7260
ttaatcatat ataattaata tcaattgggt tagcaaaaca aatctagtct aggtgtgttt    7320
tgcgaatgcg gccgataagt gactagggtc acgtgaccct agtcacttag gtaccgagct    7380
cgaattcatt ccgattaatc gtggcctctt gctcttcagg atgaagagct atgtttaaac    7440
gtgcaagcgc tactagacaa ttcagtacat taaaaacgtc cgcaatgtgt tattaagttg    7500
tctaagcgtc aatttgttta caccacaata tatcctgcca ccagccagcc aacagctccc    7560
cgaccggcag ctcggcacaa aatcaccact cgatacaggc agcccatcag tccgggacgg    7620
cgtcagcggg agagccgttg taaggcggca gactttgctc atgttaccga tgctattcgg    7680
aagaacggca actaagctgc cgggtttgaa acacggatga tctcgcggag ggtagcatgt    7740
tgattgtaac gatgacagag cgttgctgcc tgtgatcaaa tatcatctcc ctcgcagaga    7800
tccgaattat cagccttctt attcatttct cgcttaaccg tgacaggctg tcgatcttga    7860
gaactatgcc gacataatag gaaatcgctg ataaagccg ctgaggaagc tgagtggcgc    7920 tatttctttta gaagtgaacg ttgacgatcg tcgaccgtac cccgatgaat taattcggac    7980
gtacgttctg aacacagctg gatacttact tgggcgattg tcatacatga catcaacaat    8040
gtacccgttt gtgtaaccgt ctcttggagg ttcgtatgac actagtggtt cccctcagct    8100
tgcgactaga tgttgaggcc taacatttta ttagagagca ggctagttgc ttagatacat    8160
gatcttcagg ccgttatctg tcagggcaag cgaaaattgg ccatttatga cgaccaatgc    8220
cccgcagaag ctcccatctt tgccgccata gacgccgcgc ccccctttg gggtgtagaa    8280
```

```
catccttttg ccagatgtgg aaaagaagtt cgttgtccca ttgttggcaa tgacgtagta    8340
gccggcgaaa gtgcgagacc catttgcgct atatataagc ctacgatttc cgttgcgact    8400
attgtcgtaa ttggatgaac tattatcgta gttgctctca gagttgtcgt aatttgatgg    8460
actattgtcg taattgctta tggagttgtc gtagttgctt ggagaaatgt cgtagttgga    8520
tggggagtag tcatagggaa gacgagcttc atccactaaa acaattggca ggtcagcaag    8580
tgcctgcccc gatgccatcg caagtacgag gcttagaacc accttcaaca gatcgcgcat    8640
agtcttcccc agctctctaa cgcttgagtt aagccgcgcc gcgaagcggc gtcggcttga    8700
acgaattgtt agacattatt tgccgactac cttggtgatc tcgcctttca cgtagtgaac    8760
aaattcttcc aactgatctg cgcgcgaggc caagcgatct tcttgtccaa gataagcctg    8820
cctagcttca agtatgacgg gctgatactg ggccggcagg cgctccattg cccagtcggc    8880
agcgacatcc ttcggcgcga ttttgccggt tactgcgctg taccaaatgc gggacaacgt    8940
aagcactaca tttcgctcat cgccagccca gtcgggcggc gagttccata gcgttaaggt    9000
ttcatttagc gcctcaaata gatcctgttc aggaaccgga tcaaagagtt cctccgccgc    9060
tggacctacc aaggcaacgc tatgttctct tgcttttgtc agcaagatag ccagatcaat    9120
gtcgatcgtg gctggctcga agatacctgc aagaatgtca ttgcgctgcc attctccaaa    9180
ttgcagttcg cgcttagctg gataacgcca cggaatgatg tcgtcgtgca caacaatggt    9240
gacttctaca gcgcggagaa tctcgctctc tccaggggaa gccgaagttt ccaaaaggtc    9300
gttgatcaaa gctcgccgcg ttgtttcatc aagccttaca gtcaccgtaa ccagcaaatc    9360
aatatcactg tgtggcttca ggccgccatc cactgcggag ccgtacaaat gtacggccag    9420
caacgtcggt tcgagatggc gctcgatgac gccaactacc tctgatagtt gagtcgatac    9480
ttcggcgatc accgcttccc tcatgatgtt taactcctga attaagccgc gccgcgaagc    9540
ggtgtcggct tgaatgaatt gttaggcgtc atcctgtgct cccgagaacc agtaccagta    9600
catcgctgtt tcgttcgaga cttgaggtct agttttatac gtgaacaggt caatgccgcc    9660
gagagtaaag ccacattttg cgtacaaatt gcaggcaggt acattgttcg tttgtgtctc    9720
taatcgtatg ccaaggagct gtctgcttag tgcccacttt ttcgcaaatt cgatgagact    9780
gtgcgcgact cctttgcctc ggtgcgtgtg cgacacaaca atgtgttcga tagaggctag    9840
atcgttccat gttgagttga gttcaatctt cccgacaagc tcttggtcga tgaatgcgcc    9900
atagcaagca gagtcttcat cagagtcatc atccgagatg taatccttcc ggtaggggct    9960
cacacttctg gtagatagtt caaagccttg gtcggatagg tgcacatcga acacttcacg   10020
aacaatgaaa tggttctcag catccaatgt ttccgccacc tgctcaggga tcaccgaaat   10080
cttcatatga cgcctaacgc ctggcacagc ggatcgcaaa cctggcgcgg cttttggcac   10140
aaaaggcgtg acaggtttgc gaatccgttg ctgccacttg ttaaccctt tgccagattt    10200
ggtaactata atttatgtta gaggcgaagt cttgggtaaa aactggccta aaattgctgg   10260
ggatttcagg aaagtaaaca tcaccttccg gctcgatgtc tattgtagat atatgtagtg   10320
tatctacttg atcggggat ctgctgcctc gcgcgtttcg gtgatgacgg tgaaaacctc    10380
tgacacatgc agctcccgga gacggtcaca gcttgtctgt aagcggatgc cgggagcaga   10440
caagcccgtc agggcgcgtc agcgggtgtt ggcgggtgtc ggggcgcagc catgacccag   10500
tcacgtagcg atagcggagt gtatactggc ttaactatgc ggcatcagag cagattgtac   10560
tgagagtgca ccatatgcgg tgtgaaatac cgcacagatg cgtaaggaga aaataccgca   10620
tcaggcgctc ttccgcttcc tcgctcactg actcgctgcg ctcggtcgtt cggctgcggc   10680
```

```
gagcggtatc agctcactca aaggcggtaa tacggttatc cacagaatca ggggataacg    10740
caggaaagaa catgtgagca aaaggccagc aaaaggccag gaaccgtaaa aaggccgcgt    10800
tgctggcgtt tttccatagg ctccgccccc ctgacgagca tcacaaaaat cgacgctcaa    10860
gtcagaggtg gcgaaacccg acaggactat aaagatacca ggcgtttccc cctggaagct    10920
ccctcgtgcg ctctcctgtt ccgaccctgc cgcttaccgg atacctgtcc gcctttctcc    10980
cttcgggaag cgtggcgctt tctcatagct cacgctgtag gtatctcagt tcggtgtagg    11040
tcgttcgctc caagctgggc tgtgtgcacg aaccccccgt tcagcccgac cgctgcgcct    11100
tatccggtaa ctatcgtctt gagtccaacc cggtaagaca cgacttatcg ccactggcag    11160
cagccactgg taacaggatt agcagagcga ggtatgtagg cggtgctaca gagttcttga    11220
agtggtggcc taactacggc tacactagaa ggacagtatt tggtatctgc gctctgctga    11280
agccagttac cttcggaaaa agagttggta gctcttgatc cggcaaacaa accaccgctg    11340
gtagcggtgg tttttttgtt tgcaagcagc agattacgcg cagaaaaaaa ggatctcaag    11400
aagatccttt gatcttttct acggggtctg acgctcagtg gaacgaaaac tcacgttaag    11460
ggattttggt catgagatta tcaaaaagga tcttcaccta gatcctttta aattaaaaat    11520
gaagttttaa atcaatctaa agtatatatg agtaaacttg gtctgacagt taccaatgct    11580
taatcagtga ggcacctatc tcagcgatct gtctatttcg ttcatccata gttgcctgac    11640
tccccgtcgt gtagataact acgatacggg agggcttacc atctggcccc agtgctgcaa    11700
tgataccgcg agacccacgc tcaccggctc cagatttatc agcaataaac cagccagccg    11760
gaagggccga gcgcagaagt ggtcctgcaa ctttatccgc ctccatccag tctattaatt    11820
gttgccggga agctagagta agtagttcgc cagttaatag tttgcgcaac gttgttgcca    11880
ttgctgcagg ggggggggg gggggttcc attgttcatt ccacggacaa aaacagagaa    11940
aggaaacgac agaggccaaa aagctcgctt tcagcacctg tcgtttcctt tcttttcaga    12000
gggtatttta aataaaaaca ttaagttatg acgaagaaga acggaaacgc cttaaaccgg    12060
aaaattttca taaatagcga aaacccgcga ggtcgccgcc ccgtaacctg tcggatcacc    12120
ggaaaggacc cgtaaagtga taatgattat catctacata tcacaacgtg cgtggaggcc    12180
atcaaaccac gtcaaataat caattatgac gcaggtatcg tattaattga tctgcatcaa    12240
cttaacgtaa aaacaacttc agacaataca aatcagcgac actgaatacg ggcaacctc    12300 atgtccccc cccccccccc cctgcaggca tcgtggtgtc acgctcgtcg tttggtatgg    12360
cttcattcag ctccggttcc caacgatcaa ggcgagttac atgatccccc atgttgtgca    12420
aaaaagcggt tagctccttc ggtcctccga tcgttgtcag aagtaagttg gccgcagtgt    12480
tatcactcat ggttatggca gcactgcata attctcttac tgtcatgcca tccgtaagat    12540
gcttttctgt gactggtgag tactcaacca agtcattctg agaatagtgt atgcggcgac    12600
cgagttgctc ttgcccggcg tcaacacggg ataataccgc gccacatagc agaactttaa    12660
aagtgctcat cattggaaaa cgttcttcgg ggcgaaaact ctcaaggatc ttaccgctgt    12720
tgagatccag ttcgatgtaa ccccactcgtg cacccaactg atcttcagca tcttttactt    12780
tcaccagcgt ttctgggtga gcaaaaacag gaaggcaaaa tgccgcaaaa aagggaataa    12840
gggcgacacg gaaatgttga atactcatac tcttcctttt tcaatattat tgaagcattt    12900
atcagggtta ttgtctcatg agcggataca tatttgaatg tatttagaaa aataaacaaa    12960 tagggggttcc gcgcacattt ccccgaaaag tgccacctga cgtctaagaa accattatta    13020
```

```
tcatgacatt aacctataaa aataggcgta tcacgaggcc ctttcgtctt caagaattcg   13080
gagcttttgc cattctcacc ggattcagtc gtcactcatg gtgatttctc acttgataac   13140 cttattttg acgagggaa attaataggt tgtattgatg ttggacgagt cggaatcgca    13200
gaccgatacc aggatcttgc catcctatgg aactgcctcg gtgagttttc tccttcatta   13260
cagaaacggc ttttcaaaa atatggtatt gataatcctg atatgaataa attgcagttt   13320
catttgatgc tcgatgagtt tttctaatca gaattggtta attggttgta acactggcag   13380
agcattacgc tgacttgacg ggacggcggc tttgttgaat aaatcgaact tttgctgagt   13440
tgaaggatca gatcacgcat cttcccgaca acgcagaccg ttccgtggca aagcaaaagt   13500
tcaaaatcac caactggtcc acctacaaca aagctctcat caaccgtggc tccctcactt   13560
tctggctgga tgatgggcg attcaggcct ggtatgagtc agcaacaccct tcttcacgag   13620 gcagacctca gcgccagaag gccgccagag aggccgagcg cggccgtgag gcttggacgc   13680
tagggcaggg catgaaaaag cccgtagcgg gctgctacgg gcgtctgacg cggtggaaag   13740
ggggagggga tgttgtctac atggctctgc tgtagtgagt gggttgcgct ccggcagcgg   13800
tcctgatcaa tcgtcaccct ttctcggtcc ttcaacgttc ctgacaacga gcctcctttt   13860
cgccaatcca tcgacaatca ccgcgagtcc ctgctcgaac gctgcgtccg gaccggcttc   13920
gtcgaaggcg tctatcgcgg cccgcaacag cggcgagagc ggagcctgtt caacggtgcc   13980
gccgcgctcg ccggcatcgc tgtcgccggc ctgctcctca gcacggccc caacagtgaa    14040 gtagctgatt gtcatcagcg cattgacggc gtccccggcc gaaaacccg cctcgcagag    14100 gaagcgaagc tgcgcgtcgg ccgtttccat ctgcggtgcg cccggtcgcg tgccggcatg   14160
gatgcgcgcg ccatcgcggt aggcgagcag cgcctgcctg aagctgcggg cattcccgat   14220
cagaaatgag cgccagtcgt cgtcggctct cggcaccgaa tgcgtatgat tctccgccag   14280
catggcttcg gccagtgcgt cgagcagcgc ccgcttgttc ctgaagtgcc agtaaagcgc   14340
cggctgctga accccaacc gttccgcag tttgcgtgtc gtcagaccgt ctacgccgac    14400
ctcgttcaac aggtccaggg cggcacggat cactgtattc ggctgcaact ttgtcatgct   14460 tgacactta tcactgataa acataatatg tccaccaact tatcagtgat aaagaatccg    14520
cgcgttcaat cggaccagcg gaggctggtc cggaggccag acgtgaaacc caacataccc   14580
ctgatcgtaa ttctgagcac tgtcgcgctc gacgctgtcg gcatcggcct gattatgccg   14640
gtgctgccgg gcctcctgcg cgatctggtt cactcgaacg acgtcaccgc ccactatggc   14700
attctgctgg cgctgtatgc gttggtgcaa tttgcctgcg cacctgtgct gggcgcgctg   14760
tcggatcgtt tcgggcggcg gccaatcttg ctcgtctcgc tggccggcgc cactgtcgac   14820
tacgccatca tggcgacagc gccttttcctt tgggttctct atatcgggcg gatcgtggcc   14880
ggcatcaccg gggcgactgg ggcggtagcc ggcgcttata ttgccgatat cactgatggc   14940
gatgagcgcg cgcggcactt cggcttcatg agcgcctgtt tcgggttcgg gatggtcgcg   15000
ggacctgtgc tcggtgggct gatgggcggt ttctccccc acgctccgtt cttcgccgcg   15060
gcagccttga acggcctcaa tttcctgacg gctgtttcc ttttgccgga gtcgcacaaa   15120
ggcgaacgcc ggccgttacg ccgggaggct ctcaacccgc tcgcttcgtt ccggtgggcc   15180
cggggcatga ccgtcgtcgc cgccctgatg gcggtcttct tcatcatgca acttgtcgga   15240
caggtgccgg ccgcgctttg ggtcattttc ggcgaggatc gctttcactg ggacgcgacc   15300
acgatcggca tttcgcttgc cgcatttggc attctgcatt cactcgccca ggcaatgatc   15360
accggccctg tagccgcccg gctcggcgaa aggcgggcac tcatgctcgg aatgattgcc   15420
```

```
gacggcacag gctacatcct gcttgccttc gcgacacggg gatggatggc gttcccgatc   15480
atggtcctgc ttgcttcggg tggcatcgga atgccggcgc tgcaagcaat gttgtccagg   15540
caggtggatg aggaacgtca ggggcagctg caaggctcac tggcggcgct caccagcctg   15600
acctcgatcg tcggaccccct cctcttcacg gcgatctatg cggcttctat aacaacgtgg   15660
aacgggtggg catggattgc aggcgctgcc ctctacttgc tctgcctgcc ggcgctgcgt   15720
cgcgggcttt ggagcggcgc agggcaacga gccgatcgct gatcgtggaa acgataggcc   15780
tatgccatgc gggtcaaggc gacttccggc aagctatacg cgccctagga gtgcggttgg   15840
aacgttggcc cagccagata ctcccgatca cgagcaggac gccgatgatt tgaagcgcac   15900
tcagcgtctg atccaagaac aaccatccta gcaacacggc ggtccccggg ctgagaaagc   15960
ccagtaagga acaactgta ggttcgagtc gcgagatccc ccggaaccaa aggaagtagg    16020
ttaaacccgc tccgatcagg ccgagccacg ccaggccgag aacattggtt cctgtaggca   16080 tcggattgg cggatcaaac actaaagcta ctggaacgag cagaagtcct ccggccgcca    16140
gttgccaggc ggtaaaggtg agcagaggca cgggaggttg ccacttgcgg gtcagcacgg   16200
ttccgaacgc catggaaacc gcccccgcca ggcccgctgc gacgccgaca ggatctagcg   16260
ctgcgtttgg tgtcaacacc aacagcgcca cgcccgcagt tccgcaaata gcccccagga   16320
ccgccatcaa tcgtatcggg ctacctagca gagcggcaga gatgaacacg accatcagcg   16380
gctgcacagc gcctaccgtc gccgcgaccc cgcccggcag gcggtagacc gaaataaaca   16440
acaagctcca gaatagcgaa atattaagtg cgccgaggat gaagatgcgc atccaccaga   16500
ttcccgttgg aatctgtcgg acgatcatca cgagcaataa acccgccggc aacgcccgca   16560
gcagcatacc ggcgacccct cggcctcgct gttcgggctc cacgaaaacg ccggacagat   16620
gcgccttgtg agcgtccttg gggccgtcct cctgtttgaa gaccgacagc ccaatgatct   16680
cgccgtcgat gtaggcgccg aatgccacgg catctcgcaa ccgttcagcg aacgcctcca   16740 tgggctttttt ctcctcgtgc tcgtaaacgg acccgaacat ctctggagct ttcttcaggg   16800
ccgacaatcg gatctcgcgg aaatcctgca cgtcggccgc tccaagccgt cgaatctgag   16860
ccttaatcac aattgtcaat tttaatcctc tgtttatcgg cagttcgtag agcgcgccgt   16920
gcgtcccgag cgatactgag cgaagcaagt gcgtcgagca gtgcccgctt gttcctgaaa   16980
tgccagtaaa gcgctggctg ctgaaccccc agcggaact gaccccacaa ggccctagcg    17040
tttgcaatgc accaggtcat cattgaccca ggcgtgttcc accaggccgc tgcctcgcaa   17100
ctcttcgcag gcttcgccga cctgctcgcg ccacttcttc acgcgggtgg aatccgatcc   17160
gcacatgagg cggaaggttt ccagcttgag cgggtacggc tcccggtgcg agctgaaata   17220
gtcgaacatc cgtcgggccg tcggcgacag cttgcggtac ttctcccata tgaatttcgt   17280
gtagtggtcg ccagcaaaca gcacgacgat ttcctcgtcg atcaggacct ggcaacggga   17340
cgttttcttg ccacggtcca ggacgcggaa gcggtcagc agcgacaccg attccaggtg   17400
cccaacgcgg tcggacgtga agcccatcgc cgtcgcctgt aggcgcgaca ggcattcctc   17460
ggccttcgtg taataccggc cattgatcga ccagcccagg tcctggcaaa gctcgtagaa   17520
cgtgaaggtg atcggctcgc cgatagggt gcgcttcgcg tactccaaca cctgctgcca    17580
caccagttcg tcatcgtcgg cccgcagctc gacgccggtg taggtgatct tcacgtcctt   17640
gttgacgtga aaaatgacct tgtttttgcag cgcctcgcgc gggatttttct tgttgcgcgt   17700 ggtgaacagg gcagagcggg ccgtgtcgtt tggcatcgct cgcatcgtgt ccggccacgg   17760
```

```
cgcaatatcg aacaaggaaa gctgcatttc cttgatctgc tgcttcgtgt gtttcagcaa   17820
cgcggcctgc ttggcctcgc tgacctgttt tgccaggtcc tcgccggcgg ttttcgctt    17880 cttggtcgtc atagttcctc gcgtgtcgat ggtcatcgac ttcgccaaac ctgccgcctc   17940
ctgttcgaga cgacgcgaac gctccacggc ggccgatggc gcgggcaggg caggggagc    18000 cagttgcacg ctgtcgcgct cgatcttggc cgtagcttgc tggaccatcg agccgacgga   18060
ctggaaggtt tcgcggggcg cacgcatgac ggtgcggctt gcgatggttt cggcatcctc   18120
ggcggaaaac cccgcgtcga tcagttcttg cctgtatgcc ttccggtcaa acgtccgatt   18180
cattcaccct ccttgcggga ttgccccgac tcacgccggg gcaatgtgcc cttattcctg   18240
atttgacccg cctggtgcct tggtgtccag ataatccacc ttatcggcaa tgaagtcggt   18300
cccgtagacc gtctggccgt ccttctcgta cttggtattc cgaatcttgc cctgcacgaa   18360
taccagcgac cccttgccca aatacttgcc gtgggcctcg gcctgagagc caaaacactt   18420
gatgcggaag aagtcggtgc gctcctgctt gtcgccggca tcgttgcgcc actcttcatt   18480
aaccgctata tcgaaaattg cttgcggctt gttagaattg ccatgacgta cctcggtgtc   18540
acgggtaaga ttaccgataa actggaactg attatggctc atatcgaaag tctccttgag   18600
aaaggagact ctagtttagc taaacattgg ttccgctgtc aagaacttta gcggctaaaa   18660
ttttgcgggc cgcgaccaaa ggtgcgaggg gcggcttccg ctgtgtacaa ccagatattt   18720
ttcaccaaca tccttcgtct gctcgatgag cggggcatga cgaaacatga gctgtcggag   18780
agggcagggg tttcaatttc gttttatca gacttaacca acggtaaggc caacccctcg    18840
ttgaaggtga tggaggccat tgccgacgcc ctggaaactc ccctacctct tctcctggag   18900
tccaccgacc ttgaccgcga ggcactcgcg gagattgcgg gtcatccttt caagagcagc   18960
gtgccgcccg gatacgaacg catcagtgtg ttttgccgt cacataaggc gtttatcgta     19020
aagaaatggg gcgacgacac ccgaaaaaag ctgcgtggaa ggctctgacg ccaagggtta   19080
gggcttgcac ttccttcttt agccgctaaa acggccccct tctctgcggc cgtcggctcg    19140
cgcatcatat cgacatcctc aacggaagcc gtgccgcgaa tggcatcggg cgggtgcgct   19200
ttgacagttg ttttctatca gaaccccctac gtcgtgcggt tcgattagct gttttgtcttg   19260 caggctaaac actttcggta tatcgtttgc ctgtgcgata atgttgctaa tgatttgttg    19320
cgtaggggtt actgaaaagt gagcgggaaa gaagagtttc agaccatcaa ggagcgggcc   19380
aagcgcaagc tggaacgcga catgggtgcg gacctgttgg ccgcgctcaa cgacccgaaa   19440
accgttgaag tcatgctcaa cgcggacggc aaggtgtggc acgaacgcct tggcgagccg   19500
atgcggtaca tctgcgacat gcggcccagc cagtcgcagg cgattataga aacggtggcc   19560
ggattccacg gcaaagaggt cacgcggcat tcgcccatcc tggaaggcga gttcccttg    19620 gatggcagcc gctttgccgg ccaattgccg ccggtcgtgg ccgcgccaac ctttgcgatc   19680
cgcaagcgcg cggtcgccat cttcacgctg aacagtacg tcgaggcggg catcatgacc    19740
cgcgagcaat acgaggtcat taaaagcgcc gtcgcggcgc atcgaaacat cctcgtcatt   19800
ggcggtactg gctcgggcaa gaccacgctc gtcaacgcga tcatcaatga aatggtcgcc   19860
ttcaacccgt ctgagcgcgt cgtcatcatc gaggacaccg gcgaaatcca gtgcgccgca   19920
gagaacgccg tccaatacca caccagcatc gacgtctcga tgacgctgct gctcaagaca   19980
acgctgcgta tgcgccccga ccgcatcctg tcggtgaggt acgtggccc cgaagccctt    20040 gatctgttga tggcctggaa caccgggcat gaaggaggtg ccgccaccct gcacgcaaac   20100
aaccccaaag cgggcctgag ccggctcgcc atgcttatca gcatgcaccc ggattcaccg   20160
```

```
aaacccattg agccgctgat tggcgaggcg gttcatgtgg tcgtccatat cgccaggacc   20220
cctagcggcc gtcgagtgca agaaattctc gaagttcttg gttacgagaa cggccagtac   20280
atcaccaaaa ccctgtaagg agtatttcca atgacaacgg ctgttccgtt ccgtctgacc   20340
atgaatcgcg gcattttgtt ctaccttgcc gtgttcttcg ttctcgctct cgcgttatcc   20400
gcgcatccgg cgatggcctc ggaaggcacc ggcggcagct tgccatatga gagctggctg   20460
acgaacctgc gcaactccgt aaccggcccg gtggccttcg cgctgtccat catcggcatc   20520
gtcgtcgccg gcggcgtgct gatcttcggc ggcgaactca acgccttctt ccgaaccctg   20580
atcttcctgg ttctggtgat ggcgctgctg gtcggcgcgc agaacgtgat gagcaccttc   20640
ttcggtcgtg gtgccgaaat cgcggccctc ggcaacgggg cgctgcacca ggtgcaagtc   20700 gcggcggcg atgccgtgcg tgcggtagcg gctggacggc tcgcctaatc atggctctgc   20760
gcacgatccc catccgtcgc gcaggcaacc gagaaaacct gttcatgggt ggtgatcgtg   20820
aactggtgat gttctcgggc ctgatggcgt ttgcgctgat tttcagcgcc aagagctgc   20880 gggccaccgt ggtcggtctg atcctgtggt tcggggcgct ctatgcgttc cgaatcatgg   20940
cgaaggccga tccgaagatg cggttcgtgt acctgcgtca ccgccggtac aagccgtatt   21000
acccggcccg ctcgaccccg ttccgcgaga acaccaatag ccaagggaag caataccgat   21060
gatccaagca attgcgattg caatcgcggg cctcggcgcg cttctgttgt tcatcctctt   21120
tgcccgcatc cgcgcggtcg atgccgaact gaaactgaaa aagcatcgtt ccaaggacgc   21180
cggcctggcc gatctgctca actacgccgc tgtcgtcgat gacggcgtaa tcgtgggcaa   21240
gaacggcagc tttatggctg cctggctgta caagggcgat gacaacgcaa gcagcaccga   21300
ccagcagcgc gaagtagtgt ccgcccgcat caaccaggcc ctcgcgggcc tgggaagtgg   21360
gtggatgatc catgtggacg ccgtgcggcg tcctgctccg aactacgcgg agcggggcct   21420
gtcggcgttc cctgaccgtc tgacggcagc gattgaagaa gagcgctcgg tcttgccttg   21480
ctcgtcggtg atgtacttca ccagctccgc gaagtcgctc ttcttgatgg agcgcatggg   21540
gacgtgcttg gcaatcacgc gcacccccg gccgttttag cggctaaaaa agtcatggct   21600
ctgccctcgg gcgaccacg cccatcatga ccttgccaag ctcgtcctgc ttctcttcga   21660
tcttcgccag cagggcgagg atcgtggcat caccgaaccg cgccgtgcgc gggtcgtcgg   21720
tgagccagag tttcagcagg ccgcccaggc ggcccaggtc gccattgatg cgggccagct   21780
cgcggacgtg ctcatagtcc acgacgcccg tgattttgta gccctggccg acggccagca   21840
ggtaggccga caggctcatg ccggccgcg ccgccttttc ctcaatcgct cttcgttcgt   21900
ctggaaggca gtacaccttg ataggtgggc tgcccttcct ggttggcttg gtttcatcag   21960
ccatccgctt gccctcatct gttacgccgg cggtagccgg ccagcctcgc agagcaggat   22020
tcccgttgag caccgccagg tgcgaataag ggacagtgaa gaaggaacac ccgctcgcgg   22080
gtgggcctac ttcacctatc ctgcccggct gacgccgttg gatacaccaa ggaaagtcta   22140
cacgaaccct ttggcaaaat cctgtatatc gtgcgaaaaa ggatggatat accgaaaaaa   22200
tcgctataat gaccccgaag cagggttatg cagcggaaaa gcgctgcttc cctgctgttt   22260
tgtggaatat ctaccgactg gaaacaggca aatgcaggaa attactgaac tgaggggaca   22320
ggcgagagac gatgccaaag agctacaccg acgagctggc cgagtgggtt gaatcccgcg   22380
cggccaagaa gcgccggcgt gatgaggctg cggttcgtt cctggcggtg agggcggatg   22440
tcgaggcggc gttagcgtcc ggctatgcgc tcgtcaccat ttgggagcac atgcgggaaa   22500
```

```
cggggaaggt caagttctcc tacgagacgt tccgctcgca cgccaggcgg cacatcaagg    22560
ccaagcccgc cgatgtgccc gcaccgcagg ccaaggctgc ggaacccgcg ccggcaccca    22620
agacgccgga gccacggcgg ccgaagcagg ggggcaaggc tgaaaagccg gcccccgctg    22680 cggcccccgac cggcttcacc ttcaacccaa caccggacaa aaaggatcta ctgtaatggc    22740
gaaaattcac atggttttgc agggcaaggg cggggtcggc aagtcggcca tcgccgcgat    22800
cattgcgcag tacaagatgg acaaggggca gacacccttg tgcatcgaca ccgacccggt    22860
gaacgcgacg ttcgagggct acaaggccct gaacgtccgc cggctgaaca tcatggccgg    22920
cgacgaaatt aactcgcgca acttcgacac cctggtcgag ctgattgcgc cgaccaagga    22980
tgacgtggtg atcgacaacg gtgccagctc gttcgtgcct ctgtcgcatt acctcatcag    23040
caaccaggtg ccggctctgc tgcaagaaat ggggcatgag ctggtcatcc ataccgtcgt    23100
caccggcggc caggctctcc tggacacggt gagcggcttc gcccagctcg ccagccagtt    23160 cccgccgaa gcgcttttcg tggtctggct gaacccgtat tggggggccta tcgagcatga    23220 gggcaagagc tttgagcaga tgaaggcgta cacgccaac aaggcccgcg tgtcgtccat    23280
catccagatt ccggccctca aggaagaaac ctacggccgc gatttcagcg acatgctgca    23340
agagcggctg acgttcgacc aggcgctggc cgatgaatcg ctcacgatca tgacgcggca    23400
acgcctcaag atcgtgcggc gcggcctgtt tgaacagctc gacgcggcgg ccgtgctatg    23460
agcgaccaga ttgaagagct gatccgggag attgcggcca agcacggcat cgccgtcggc    23520
cgcgacgacc cggtgctgat cctgcatacc atcaacgccc ggctcatggc cgacagtgcg    23580
gccaagcaag aggaaatcct tgccgcgttc aaggaagagc tggaagggat cgcccatcgt    23640
tggggcgagg acgccaaggc caaagcggag cggatgctga acgcggccct ggcggccagc    23700
aaggacgcaa tggcgaaggt aatgaaggac agcgccgcgc aggcggccga agcgatccgc    23760
agggaaatcg acgacggcct tggccgccag ctcgcggcca aggtcgcgga cgcgcggcgc    23820
gtggcgatga tgaacatgat cgccggcggc atggtgttgt tcgcggccgc cctggtggtg    23880
tgggcctcgt tatgaatcgc agaggcgcag atgaaaaagc ccggcgttgc cgggctttgt    23940
ttttgcgtta gctgggcttg tttgacaggc ccaagctctg actgcgcccg cgctcgcgct    24000
cctgggcctg tttcttctcc tgctcctgct tgcgcatcag ggcctggtgc cgtcgggctg    24060
cttcacgcat cgaatcccag tcgccggcca gctcggatg ctccgcgcgc atcttgcgcg    24120
tcgccagttc ctcgatcttg ggcgcgtgaa tgcccatgcc ttccttgatt tcgcgcacca    24180
tgtccagccg cgtgtgcagg gtctgcaagc gggcttgctg ttgggcctgc tgctgctgcc    24240
aggcggcctt tgtacgcggc agggacagca agccggggggc attggactgt agctgctgca    24300
aacgcgcctg ctgacggtct acgagctgtt ctaggcggtc ctcgatgcgc tccacctggt    24360
catgctttgc ctgcacgtag agcgcaaggg tctgctggta ggtctgctcg atgggcgcgg    24420
attctaagag ggcctgctgt tccgtctcgg cctcctgggc cgcctgtagc aaatcctcgc    24480
cgctgttgcc gctggactgc tttactgccg gggactgctg ttgccctgct cgcgccgtcg    24540
tcgcagttcg gcttgccccc actcgattga ctgcttcatt tcgagccgca gcgatgcgat    24600
ctcggattgc gtcaacggac ggggcagcgc ggaggtgtcc ggcttctcct ggggtgagtc    24660
ggtcgatgcc atagccaaag gtttccttcc aaaatgcgtc cattgctgga ccgtgtttct    24720
cattgatgcc cgcaagcatc ttcggcttga ccgccaggtc aagcgcgcct tcatgggcgg    24780
tcatgacgga cgccgccatg accttgccgc cgttgttctc gatgtagccg cgtaatgagg    24840
caatggtgcc gcccatcgtc agcgtgtcat cgacaacgat gtacttctgg ccgggggatca    24900
```

```
cctcccctc gaaagtcggg ttgaacgcca ggcgatgatc tgaaccggct ccggttcggg   24960
cgaccttctc ccgctgcaca atgtccgttt cgacctcaag gccaaggcgg tcggccagaa   25020
cgaccgccat catggccgga atcttgttgt tccccgccgc ctcgacggcg aggactggaa   25080
cgatgcgggg cttgtcgtcg ccgatcagcg tcttgagctg ggcaacagtg tcgtccgaaa   25140
tcaggcgctc gaccaaatta agcgccgctt ccgcgtcgcc ctgcttcgca gcctggtatt   25200
caggctcgtt ggtcaaagaa ccaaggtcgc cgttgcgaac caccttcggg aagtctcccc   25260
acggtgcgcg ctcggctctg ctgtagctgc tcaagacgcc tccctttta gccgctaaaa   25320 ctctaacgag tgcgcccgcg actcaacttg acgctttcgg cacttacctg tgccttgcca   25380
cttgcgtcat aggtgatgct tttcgcactc ccgatttcag gtactttatc gaaatctgac   25440
cgggcgtgca ttacaaagtt cttccccacc tgttggtaaa tgctgccgct atctgcgtgg   25500
acgatgctgc cgtcgtggcg ctgcgactta tcggcctttt gggccatata gatgttgtaa   25560
atgccaggtt tcagggcccc ggctttatct accttctggt tcgtccatgc gccttggttc   25620
tcggtctgga caattctttg cccattcatg accaggaggc ggtgtttcat tgggtgactc   25680
ctgacgcttg cctctggtgt taaacgtgtc ctggtcgctt gccggctaaa aaaaagccga   25740
cctcggcagt tcgaggccgg cttccctag agccgggcgc gtcaaggttg ttccatctat   25800
tttagtgaac tgcgttcgat ttatcagtta ctttcctccc gctttgtgtt tcctcccact   25860
cgtttccgcg tctagccgac ccctcaacat agcggcctct tcttgggctg cctttgcctc   25920
ttgccgcgct tcgtcacgct cggcttgcac cgtcgtaaag cgctcggcct gcctggccgc   25980
ctcttgcgcc gccaacttcc tttgctcctg gtgggcctcg gcgtcggcct gcgccttcgc   26040
tttcaccgct gccaactccg tgcgcaaact ctccgcttcg cgcctggtgg cgtcgcgctc   26100
gccgcgaagc gcctgcattt cctggttggc cgcgtccagg gtcttgcggc tctcttcttt   26160
gaatgcgcgg gcgtcctggt gagcgtagtc cagctcggcg cgcagctcct gcgctcgacg   26220
ctccacctcg tcgcccgct gcgtcgccag cgcggcccgc tgctcggctc ctgccagggc   26280
ggtgcgtgct tcggccaggg cttgccgctg cgtgcggcc agctcggccg cctcggcggc   26340
ctgctgctct agcaatgtaa cgcgcgcctg ggcttcttcc agctcgcggg cctgcgcctc   26400
gaaggcgtcg gccagctccc cgcgcacggc ttccaactcg ttgcgctcac gatcccagcc   26460
ggcttgcgct gcctgcaacg attcattggc aagggcctgg gcggcttgcc agagggcggc   26520
cacggcctgg ttgccggcct gctgcaccgc gtccggcacc tggactgcca gcggggcggc   26580
ctgcgccgtg cgctggcgtc gccattcgcg catgccggcg ctggcgtcgt tcatgttgac   26640
gcgggcggcc ttacgcactg catccacggt cgggaagttc tcccggtcgc cttgctcgaa   26700
cagctcgtcc gcagccgcaa aaatgcggtc gcgcgtctct tgttcagtt ccatgttggc   26760 tccggtaatt ggtaagaata ataatactct tacctacctt atcagcgcaa gagtttagct   26820
gaacagttct cgacttaacg gcaggttttt tagcggctga agggcaggca aaaaaagccc   26880
cgcacggtcg gcggggggcaa agggtcagcg ggaagggggat tagcgggcgt cgggcttctt   26940
catgcgtcgg ggccgcgctt cttgggatgg agcacgacga agcgcgcacg cgcatcgtcc   27000
tcggccctat cggcccgcgt cgcggtcagg aacttgtcgc gcgctaggtc ctccctggtg   27060
ggcaccaggg gcatgaactc ggcctgctcg atgtaggtcc actccatgac cgcatcgcag   27120
tcgaggccgc gttccttcac cgtctcttgc aggtcgcggt acgcccgctc gttgagcggc   27180
tggtaacggg ccaattggtc gtaaatggct gtcggccatg agcggccttt cctgttgagc   27240
```

```
cagcagccga cgacgaagcc ggcaatgcag gccccctggca caaccaggcc gacgccgggg   27300 gcagggatg gcagcagctc gccaaccagg aaccccgccg cgatgatgcc gatgccggtc     27360
aaccagccct tgaaactatc cggccccgaa acacccctgc gcattgcctg gatgctgcgc    27420
cggatagctt gcaacatcag gagccgtttc ttttgttcgt cagtcatggt ccgccctcac    27480
cagttgttcg tatcggtgtc ggacgaactg aaatcgcaag agctgccggt atcggtccag    27540
ccgctgtccg tgtcgctgct gccgaagcac ggcgaggggt ccgcgaacgc cgcagacggc    27600
gtatccggcc gcagcgcatc gcccagcatg gccccggtca gcgagccgcc ggccaggtag    27660
cccagcatgg tgctgttggt cgccccggcc accagggccg acgtgacgaa atcgccgtca    27720
ttccctctgg attgttcgct gctcggcggg gcagtgcgcc gcgccggcgg cgtcgtggat    27780
ggctcgggtt ggctggcctg cgacggccgg cgaaaggtgc gcagcagctc gttatcgacc    27840
ggctgcggcg tcgggccgc cgccttgcgc tgcggtcggt gttccttctt cggctcgcgc     27900
agcttgaaca gcatgatcgc ggaaaccagc agcaacgccg cgcctacgcc tcccgcgatg    27960
tagaacagca tcggattcat tcttcggtcc tccttgtagc ggaaccgttg tctgtgcggc    28020
gcgggtggcc cgcgccgctg tctttgggga tcagccctcg atgagcgcga ccagtttcac    28080
gtcggcaagg ttcgcctcga actcctggcc gtcgtcctcg tacttcaacc aggcatagcc    28140
ttccgccggc ggccgacggt tgaggataag gcgggcaggg cgctcgtcgt gctcgacctg    28200
gacgatggcc tttttcagct tgtccgggtc cggctccttc gcgccctttt ccttggcgtc    28260
cttaccgtcc tggtcgccgt cctcgccgtc ctggccgtcg ccggcctccg cgtcacgctc    28320
ggcatcagtc tggccgttga aggcatcgac ggtgttggga tcgcggccct tctcgtccag   28380
gaactcgcgc agcagcttga ccgtgccgcg cgtgatttcc tgggtgtcgt cgtcaagcca    28440
cgcctcgact tcctccgggc gcttcttgaa ggccgtcacc agctcgttca ccacggtcac    28500
gtcgcgcacg cggccggtgt tgaacgcatc ggcgatcttc tccggcaggt ccagcagcgt    28560
gacgtgctgg gtgatgaacg ccggcgactt gccgatttcc ttggcgatat cgcctttctt    28620
cttgcccttc gccagctcgc ggccaatgaa gtcggcaatt tcgcgcgggg tcagctcgtt    28680
gcgttgcagg ttctcgataa cctggtcggc ttcgttgtag tcgttgtcga tgaacgccgg    28740
gatggacttc ttgccggccc acttcgagcc acggtagcgg cgggcgccgt gattgatgat    28800
atagcggccc ggctgctcct ggttctcgcg caccgaaatg ggtgacttca ccccgcgctc    28860
tttgatcgtg gcaccgattt ccgcgatgct ctccggggaa aagccggggt tgtcggccgt    28920
ccgcggctga tgcggatctt cgtcgatcag gtccaggtcc agctcgatag ggccggaacc    28980
gccctgagac gccgcaggag cgtccaggag gctcgacagg tcgccgatgc tatccaaccc    29040
caggccggac ggctgcgccg cgcctgcggc ttcctgagcg gccgcagcgg tgttttctt     29100 ggtggtcttg gcttgagccg cagtcattgg gaaatctcca tcttcgtgaa cacgtaatca    29160
gccagggcgc gaacctcttt cgatgccttg cgcgcggccg ttttcttgat cttccagacc    29220
ggcacaccgg atgcgagggc atcggcgatg ctgctgcgca ggccaacggt ggccggaatc    29280
atcatcttgg ggtacgcggc cagcagctcg gcttggtggc gcgcgtggcg cggattccgc    29340
gcatcgacct tgctgggcac catgccaagg aattgcagct tggcgttctt ctggcgcacg    29400
ttcgcaatgg tcgtgaccat cttcttgatg ccctggatgc tgtacgcctc aagctcgatg    29460
ggggacagca catagtcggc cgcgaagagg gcggccgcca ggccgacgcc aagggtcggg    29520
gccgtgtcga tcaggcacac gtcgaagcct tggttcgcca gggccttgat gttcgccccg    29580
aacagctcgc gggcgtcgtc cagcgacagc cgttcggcgt tcgccagtac cgggttggac    29640
```

```
tcgatgaggg cgaggcgcgc ggcctggccg tcgccggctg cgggtgcggt ttcggtccag   29700
ccgccggcag ggacagcgcc gaacagcttg cttgcatgca ggccggtagc aaagtccttg   29760
agcgtgtagg acgcattgcc ctgggggtcc aggtcgatca cggcaacccg caagccgcgc   29820
tcgaaaaagt cgaaggcaag atgcacaagg gtcgaagtct tgccgacgcc gcctttctgg   29880
ttggccgtga ccaaagtttt catcgtttgg tttcctgttt tttcttggcg tccgcttccc   29940
acttccggac gatgtacgcc tgatgttccg gcagaaccgc cgttaccgcc gcgtacccct   30000
cgggcaagtt cttgtcctcg aacgcggccc acacgcgatg caccgcttgc gacactgcgc   30060
ccctggtcag tcccagcgac gttgcgaacg tcgcctgtgg cttcccatcg actaagacgc   30120
cccgcgctat ctcgatggtc tgctgcccca cttccagccc ctggatcgcc tcctggaact   30180
ggctttcggt aagccgtttc ttcatggata cacccataa tttgctccgc gccttggttg   30240
aacatagcgg tgacagccgc cagcacatga gagaagttta gctaaacatt tctcgcacgt   30300
caacaccttt agccgctaaa actcgtcctt ggcgtaacaa aacaaaagcc cggaaaccgg   30360
gctttcgtct cttgccgctt atggctctgc acccggctcc atcaccaaca ggtcgcgcac   30420
gcgcttcact cggttgcgga tcgacactgc cagcccaaca aagccggttg ccgccgccgc   30480
caggatcgcg ccgatgatgc cggccacacc ggccatcgcc caccaggtcg ccgccttccg   30540
gttccattcc tgctggtact gcttcgcaat gctggacctc ggctaccat aggctgaccg   30600 ctcgatggcg tatgccgctt ctcccttgg cgtaaaaccc agccgcgcag gcggcattgc   30660
catgctgccc gccgctttcc cgaccacgac gcgcgcacca ggcttgcggt ccagaccttc   30720
ggccacggcg agctgcgcaa ggacataatc agccgccgac ttggctccac gcgcctcgat   30780
cagctcttgc actcgcgcga aatccttggc ctccacggcc gccatgaatc gcgcacgcgg   30840
cgaaggctcc gcagggccgg cgtcgtgatc gccgccgaga atgcccttca ccaagttcga   30900
cgacacgaaa atcatgctga cggctatcac catcatgcag acggatcgca cgaacccgct   30960
gaattgaaca cgagcacggc acccgcgacc actatgccaa gaatgcccaa ggtaaaaatt   31020 gccggcc c ccatgaagtc cgtgaatgcc ccgacggccg aagtgaaggg caggccgcca   31080
cccaggccgc cgccctcact gcccggcacc tggtcgctga atgtcgatgc cagcacctgc   31140
ggcacgtcaa tgcttccggg cgtcgcgctc gggctgatcg cccatcccgt tactgccccg   31200
atcccggcaa tggcaaggac tgccagcgct gccattttg gggtgaggcc gttcgcggcc   31260
gaggggcgca gccctgggg ggatgggagg cccgcgttag cgggccggga gggttcgaga   31320 aggggggca cccccccttcg gcgtgcgcgg tcacgcgcac agggcgcagc cctggttaaa   31380
aacaaggttt ataaatattg gtttaaaagc aggttaaaag acaggttagc ggtggccgaa   31440
aaacgggcgg aaaccttgc aaatgctgga ttttctgcct gtggacagcc cctcaaatgt   31500
caataggtgc gccctcatc tgtcagcact ctgcccctca agtgtcaagg atcgcgcccc   31560
tcatctgtca gtagtcgcgc ccctcaagtg tcaataccgc agggcactta tcccccaggct   31620 tgtccacatc atctgtggga aactcgcgta aaatcaggcg ttttcgccga tttgcgaggc   31680
tggccagctc cacgtcgccg gccgaaatcg agcctgcccc tcatctgtca acgccgcgcc   31740
gggtgagtcg gcccctcaag tgtcaacgtc cgccctcat ctgtcagtga ggccaagtt   31800 ttccgcgagg tatccacaac gccgccggcc gcggtgtctc gcacacggct tcgacggcgt   31860
ttctggcgcg tttgcagggc catagacggc cgccagccca gcggcgaggg caaccagccc   31920
ggtgagcgtc ggaaaggcgc tggaagcccc gtagcgacgc ggagaggggc gagacaagcc   31980
```

```
aagggcgcag gctcgatgcg cagcacgaca tagccggttc tcgcaaggac gagaatttcc   32040
ctgcggtgcc cctcaagtgt caatgaaagt ttccaacgcg agccattcgc gagagccttg   32100
agtccacgct agatgagagc tttgttgtag gtggaccagt tggtgatttt gaacttttgc   32160
tttgccacgg aacggtctgc gttgtcggga agatgcgtga tctgatcctt caactcagca   32220
aaagttcgat ttattcaaca aagccacgtt gtgtctcaaa atctctgatg ttacattgca   32280
caagataaaa atatatcatc atgaacaata aaactgtctg cttacataaa cagtaataca   32340
aggggtgtta tgagccatat tcaacgggaa acgtcttgct cgactctaga gctcgttcct   32400
cgaggcctcg aggcctcgag gaacggtacc tgcggggaag cttacaataa tgtgtgttgt   32460
taagtcttgt tgcctgtcat cgtctgactg actttcgtca taaatcccgg cctccgtaac   32520
ccagctttgg gcaagctcac ggatttgatc cggcggaacg ggaatatcga gatgccgggc   32580
tgaacgctgc agttccagct ttcccttttcg ggacaggtac tccagctgat tgattatctg   32640
ctgaagggtc ttggttccac ctcctggcac aatgcgaatg attacttgag cgcgatcggg   32700
catccaattt tctcccgtca ggtgcgtggt caagtgctac aaggcacctt tcagtaacga   32760
gcgaccgtcg atccgtcgcc gggatacgga caaaatggag cgcagtagtc catcgagggc   32820
ggcgaaagcc tcgccaaaag caatacgttc atctcgcaca gcctccagat ccgatcgagg   32880
gtcttcggcg taggcagata gaagcatgga tacattgctt gagagtattc cgatggactg   32940
aagtatggct tccatctttt tctcgtgtgtc tgcatctatt tcgagaaagc ccccgatgcg   33000
gcgcaccgca acgcgaattg ccatactatc cgaaagtccc agcaggcgcg cttgatagga   33060
aaaggtttca tactcggccg atcgcagacg ggcactcacg accttgaacc cttcaacttt   33120
cagggatcga tgctggttga tggtagtctc actcgacgtg gctctggtgt gttttgacat   33180
agcttcctcc aaagaaagcg gaaggtctgg atactccagc acgaaatgtg cccgggtaga   33240
cggatggaag tctagccctg ctcaatatga aatcaacagt acatttacag tcaatactga   33300
atatacttgc tacatttgca attgtcttat aacgaatgtg aaataaaaat agtgtaacaa   33360
cgcttttact catcgataat cacaaaaaca tttatacgaa caaaaataca aatgcactcc   33420
ggtttcacag gataggcggg atcagaatat gcaacttttg acgttttgtt ctttcaaagg   33480
gggtgctggc aaaaccaccg cactcatggg cctttgcgct gctttggcaa atgacggtaa   33540
acgagtggcc ctctttgatg ccgacgaaaa ccggcctctg acgcgatgga gagaaaacgc   33600
cttacaaagc agtactggga tcctcgctgt gaagtctatt ccgccgacga aatgcccctt   33660
cttgaagcag cctatgaaaa tgccgagctc gaaggatttg attatgcgtt ggccgatacg   33720
cgtggcggct cgagcgagct caacaacaca atcatcgcta gctcaaacct gcttctgatc   33780
cccaccatgc taacgccgct cgacatcgat gaggcactat ctacctaccg ctacgtcatc   33840
gagctgctgt tgagtgaaaa tttggcaatt cctacagctg ttttgcgcca acgcgtcccg   33900
gtcggccgat tgacaacatc gcaacgcagg atgtcagaga cgctagagag ccttccagtt   33960
gtaccgtctc ccatgcatga aagagatgca tttgccgcga tgaaagaacg cggcatgttg   34020
catcttacat tactaaacac gggaactgat ccgacgatgc gcctcataga gaggaatctt   34080
cggattgcga tggaggaagt cgtggtcatt tcgaaactga tcagcaaaat cttggaggct   34140
tgaagatggc aattcgcaag cccgcattgt cggtcggcga agcacggcgg cttgctggtg   34200
ctcgacccga gatccaccat cccaacccga cacttgttcc ccagaagctg gacctccagc   34260
acttgcctga aaaagccgac gagaaagacc agcaacgtga gcctctcgtc gccgatcaca   34320
tttacagtcc cgatcgacaa cttaagctaa ctgtggatgc ccttagtcca cctccgtccc   34380
```

```
cgaaaaagct ccaggttttt ctttcagcgc gaccgcccgc gcctcaagtg tcgaaaacat   34440
atgacaacct cgttcggcaa tacagtccct cgaagtcgct acaaatgatt ttaaggcgcg   34500
cgttggacga tttcgaaagc atgctggcag atggatcatt tcgcgtggcc ccgaaaagtt   34560
atccgatccc ttcaactaca gaaaaatccg ttctcgttca gacctcacgc atgttcccgg   34620
ttgcgttgct cgaggtcgct cgaagtcatt ttgatccgtt ggggttggag accgctcgag   34680 cttcggcca caagctggct accgccgcgc tcgcgtcatt ctttgctgga gagaagccat   34740
cgagcaattg gtgaagaggg acctatcgga acccctcacc aaatattgag tgtaggtttg   34800
aggccgctgg ccgcgtcctc agtcaccttt tgagccagat aattaagagc caaatgcaat   34860
tggctcaggc tgccatcgtc ccccgtgcg aaacctgcac gtccgcgtca agaaataac    34920 cggcacctct tgctgttttt atcagttgag ggcttgacgg atccgcctca gtttgcggc    34980 gcagccgcaa aatgagaaca tctatactcc tgtcgtaaac ctcctcgtcg cgtactcgac   35040
tggcaatgag aagttgctcg cgcgatagaa cgtcgcgggg tttctctaaa aacgcgagga   35100
gaagattgaa ctcacctgcc gtaagtttca cctcaccgcc agcttcggac atcaagcgac   35160
gttgcctgag attaagtgtc cagtcagtaa aacaaaaaga ccgtcggtct ttggagcgga   35220
caacgttggg gcgcacgcgc aaggcaaccc gaatgcgtgc aagaaactct ctcgtactaa   35280
acggcttagc gataaaatca cttgctccta gctcgagtgc aacaacttta tccgtctcct   35340
caaggcggtc gccactgata attatgattg gaatatcaga ctttgccgcc agatttcgaa   35400
cgatctcaag cccatcttca cgacctaaat ttagatcaac aaccacgaca tcgaccgtcg   35460
cggaagagag tactctagtg aactgggtgc tgtcggctac cgcggtcact ttgaaggcgt   35520
ggatcgtaag gtattcgata taagatgcc gcatagcgac atcgtcatcg ataagaagaa    35580
cgtgtttcaa cggctcacct ttcaatctaa aatctgaacc cttgttcaca gcgcttgaga   35640
aattttcacg tgaaggatgt acaatcatct ccagctaaat gggcagttcg tcagaattgc   35700
ggctgaccgc ggatgacgaa aatgcgaacc aagtatttca attttatgac aaaagttctc   35760
aatcgttgtt acaagtgaaa cgcttcgagg ttacagctac tattgattaa ggagatcgcc   35820
tatggtctcg ccccggcgtc gtgcgtccgc cgcgagccag atctcgccta cttcataaac   35880
gtcctcatag gcacggaatg gaatgatgac atcgatcgcc gtagagagca tgtcaatcag   35940
tgtgcgatct tccaagctag caccttgggc gctactttg acaagggaaa acagtttctt    36000
gaatccttgg attggattcg cgccgtgtat tgttgaaatc gatcccggat gtcccgagac   36060
gacttcactc agataagccc atgctgcatc gtcgcgcatc tcgccaagca atatccggtc   36120
cggccgcata cgcagacttg cttggagcaa gtgctcggcg ctcacagcac ccagcccagc   36180
accgttcttg gagtagagta gtctaacatg attatcgtgt ggaatgacga gttcgagcgt   36240
atcttctatg gtgattagcc tttcctgggg ggggatggcg ctgatcaagg tcttgctcat   36300
tgttgtcttg ccgcttccgg tagggccaca tagcaacatc gtcagtcggc tgacgacgca   36360
tgcgtgcaga aacgcttcca aatccccgtt gtcaaaatgc tgaaggatag cttcatcatc   36420
ctgattttgg cgtttccttc gtgtctgcca ctggttccac ctcgaagcat cataacggga   36480
ggagacttct ttaagaccag aaacacgcga gcttggccgt cgaatggtca agctgacggt   36540
gcccgaggga acgtcggcg gcagacagat ttgtagtcgt tcaccaccag gaagttcagt    36600
ggcgcagagg gggttacgtg gtccgacatc ctgcttctc agcgcgcccg ctaaaatagc    36660
gatatcttca agatcatcat aagagacggg caaaggcatc ttggtaaaaa tgccggcttg   36720
```

```
gcgcacaaat gcctctccag gtcgattgat cgcaatttct tcagtcttcg ggtcatcgag   36780
ccattccaaa atcggcttca gaagaaagcg tagttgcgga tccacttcca tttacaatgt   36840
atcctatctc taagcggaaa tttgaattca ttaagagcgg cggttcctcc cccgcgtggc   36900
gccgccagtc aggcggagct ggtaaacacc aaagaaatcg aggtcccgtg ctacgaaaat   36960
ggaaacggtg tcaccctgat tcttcttcag ggttggcggt atgttgatgg ttgccttaag   37020
ggctgtctca gttgtctgct caccgttatt ttgaaagctg ttgaagctca tcccgccacc   37080
cgagctgccg gcgtaggtgc tagctgcctg gaaggcgcct tgaacaacac tcaagagcat   37140
agctccgcta aaacgctgcc agaagtggct gtcgaccgag cccggcaatc ctgagcgacc   37200
gagttcgtcc gcgcttggcg atgttaacga gatcatcgca tggtcaggtg tctcggcgcg   37260
atcccacaac acaaaaacgc gcccatctcc ctgttgcaag ccacgctgta tttcgccaac   37320
aacggtggtg ccacgatcaa gaagcacgat attgttcgtt gttccacgaa tatcctgagg   37380
caagacacac tttacatagc ctgccaaatt tgtgtcgatt gcggtttgca agatgcacgg   37440
aattattgtc ccttgcgtta ccataaaatc ggggtgcggc aagagcgtgg cgctgctggg   37500
ctgcagctcg gtgggtttca tacgtatcga caaatcgttc tcgccggaca cttcgccatt   37560
cggcaaggag ttgtcgtcac gcttgccttc ttgtcttcgg cccgtgtcgc cctgaatggc   37620
gcgtttgctg acccttgat cgccgctgct atatgcaaaa atcggtgttt cttccggccg   37680
tggctcatgc cgctccggtt cgcccctcgg cggtagagga gcagcaggct gaacagcctc   37740
ttgaaccgct ggaggatccg gcggcacctc aatcggagct ggatgaaatg gcttggtgtt   37800
tgttgcgatc aaagttgacg gcgatgcgtt ctcattcacc ttcttttggc gcccacctag   37860
ccaaatgagg cttaatgata acgcgagaac gacacctccg acgatcaatt tctgagaccc   37920
cgaaagacgc cggcgatgtt tgtcggagac cagggatcca gatgcatcaa cctcatgtgc   37980
cgcttgctga ctatcgttat tcatcccttc gccccttca ggacgcgttt cacatcgggc   38040
ctcaccgtgc ccgtttgcgg ccttttggcca acgggatcgt aagcggtgtt ccagatacat   38100
agtactgtgt ggccatccct cagacgccaa cctcgggaaa ccgaagaaat ctcgacatcg   38160 ctcccttttaa ctgaatagtt ggcaacagct tccttgccat caggattgat ggtgtagatg   38220
gagggtatgc gtacattgcc cggaaagtgg aataccgtcg taaatccatt gtcgaagact   38280
tcgagtggca acagcgaacg atcgccttgg gcgacgtagt gccaattact gtccgccgca   38340
ccaagggctg tgacaggctg atccaataaa ttctcagctt tccgttgata ttgtgcttcc   38400
gcgtgtagtc tgtccacaac agccttctgt tgtgcctccc ttcgccgagc cgccgcatcg   38460
tcggcggggt aggcgaattg gacgctgtaa tagagatcgg gctgctcttt atcgaggtgg   38520
gacagagtct tggaacttat actgaaaaca taacggcgca tcccggagtc gcttgcggtt   38580
agcacgatta ctggctgagg cgtgaggacc tggcttgcct tgaaaaatag ataatttccc   38640
cgcggtaggg ctgctagatc tttgctattt gaaacggcaa ccgctgtcac cgtttcgttc   38700
gtggcgaatg ttacgaccaa agtagctcca accgccgtcg agaggcgcac cacttgatcg   38760
ggattgtaag ccaaataacg catgcgcgga tctagcttgc ccgccattgg agtgtcttca   38820
gcctccgcac cagtcgcagc ggcaaataaa catgctaaaa tgaaaagtgc ttttctgatc   38880
atggttcgct gtggcctacg tttgaaacgg tatcttccga tgtctgatag gaggtgacaa   38940
ccagacctgc cggggttggtt agtctcaatc tgccgggcaa gctggtcacc ttttcgtagc   39000
gaactgtcgc ggtccacgta ctcaccacag gcattttgcc gtcaacgacg agggtccttt   39060
tatagcgaat ttgctgcgtg cttggagtta catcatttga agcgatgtgc tcgacctcca   39120
```

```
ccctgccgcg tttgccaaga atgacttgag gcgaactggg attgggatag ttgaagaatt   39180
gctggtaatc ctggcgcact gttggggcac tgaagttcga taccaggtcg taggcgtact   39240
gagcggtgtc ggcatcataa ctctcgcgca ggcgaacgta ctcccacaat gaggcgttaa   39300
cgacggcctc ctcttgagtt gcaggcaatc gcgagacaga cacctcgctg tcaacggtgc   39360
cgtccggccg tatccataga tatacgggca caagcctgct caacggcacc attgtggcta   39420
tagcgaacgc ttgagcaaca tttcccaaaa tcgcgatagc tgcgacagct gcaatgagtt   39480
tggagagacg tcgcgccgat ttcgctcgcg cggtttgaaa ggcttctact tccttatagt   39540
gctcggcaag gctttcgcgc gccactagca tggcatattc aggccccgtc atagcgtcca   39600
cccgaattgc cgagctgaag atctgacgga gtaggctgcc atcgcccac attcagcggg    39660 aagatcgggc ctttgcagct cgctaatgtg tcgtttgtct ggcagccgct caaagcgaca   39720
actaggcaca gcaggcaata cttcatagaa ttctccattg aggcgaattt ttgcgcgacc   39780
tagcctcgct caacctgagc gaagcgacgg tacaagctgc tggcagattg ggttgcgccg   39840
ctccagtaac tgcctccaat gttgccggcg atcgccggca aagcgacaat gagcgcatcc   39900
cctgtcagaa aaacatatc gagttcgtaa agaccaatga tcttggccgc ggtcgtaccg    39960
gcgaaggtga ttacaccaag cataagggtg agcgcagtcg cttcggttag gatgacgatc   40020
gttgccacga ggtttaagag gagaagcaag agaccgtagg tgataagttg cccgatccac   40080
ttagctgcga tgtcccgcgt gcgatcaaaa atatatccga cgaggatcag aggcccgatc   40140
gcgagaagca ctttcgtgag aattccaacg gcgtcgtaaa ctccgaaggc agaccagagc   40200
gtgccgtaaa ggacccactg tgcccctttgg aaagcaagga tgtcctggtc gttcatcgga  40260
ccgatttcgg atgcgatttt ctgaaaaacg gcctgggtca cggcgaacat tgtatccaac   40320
tgtgccggaa cagtctgcag aggcaagccg gttacactaa actgctgaac aaagtttggg   40380
accgtctttt cgaagatgga aaccacatag tcttggtagt tagcctgccc aacaattaga   40440
gcaacaacga tggtgaccgt gatcacccga gtgataccgc tacgggtatc gacttcgccg   40500
cgtatgacta aaataccctg aacaataatc caaagagtga cacaggcgat caatggcgca   40560
ctcaccgcct cctggatagt ctcaagcatc gagtccaagc ctgtcgtgaa ggctacatcg   40620
aagatcgtat gaatggccgt aaacggcgcc ggaatcgtga aattcatcga ttggacctga   40680
acttgactgg tttgtcgcat aatgttggat aaaatgagct cgcattcggc gaggatgcgg   40740
gcggatgaac aaatcgccca gccttagggg agggcaccaa agatgacagc ggtcttttga   40800
tgctccttgc gttgagcggc cgcctcttcc gcctcgtgaa ggccggcctg cgcggtagtc   40860
atcgttaata ggcttgtcgc ctgtacattt tgaatcattg cgtcatggat ctgcttgaga   40920
agcaaaccat tggtcacggt tgcctgcatg atattgcgag atcgggaaag ctgagcagac   40980
gtatcagcat tcgccgtcaa gcgtttgtcc atcgtttcca gattgtcagc cgcaatgcca   41040
gcgctgtttg cggaaccggt gatctgcgat cgcaacaggt ccgcttcagc atcactaccc   41100
acgactgcac gatctgtatc gctggtgatc gcacgtgccg tggtcgacat tggcattcgc   41160
ggcgaaaaca tttcattgtc taggtccttc gtcgaaggat actgattttt ctggttgagc   41220
gaagtcagta gtccagtaac gccgtaggcc gacgtcaaca tcgtaaccat cgctatagtc   41280
tgagtgagat tctccgcagt cgcgagcgca gtcgcgagcg tctcagcctc cgttgccggg   41340
tcgctaacaa caaactgcgc ccgcgcgggc tgaatatata gaaagctgca ggtcaaaact   41400
gttgcaataa gttgcgtcgt cttcatcgtt tcctaccta tcaatcttct gcctcgtggt    41460
```

```
gacgggccat gaattcgctg agccagccag atgagttgcc ttcttgtgcc tcgcgtagtc   41520
gagttgcaaa gcgcaccgtg ttggcacgcc ccgaaagcac ggcgacatat tcacgcatat   41580
cccgcagatc aaattcgcag atgacgcttc cactttctcg tttaagaaga aacttacggc   41640
tgccgaccgt catgtcttca cggatcgcct gaaattcctt ttcggtacat ttcagtccat   41700
cgacataagc cgatcgatct gcggttggtg atggatagaa aatcttcgtc atacattgcg   41760
caaccaagct ggctcctagc ggcgattcca gaacatgctc tggttgctgc gttgccagta   41820
ttagcatccc gttgttttt cgaacggtca ggaggaattt gtcgacgaca gtcgaaaatt   41880
tagggtttaa caaataggcg cgaaactcat cgcagctcat cacaaaacgg cggccgtcga   41940
tcatggctcc aatccgatgc aggagatatg ctgcagcggg agcgcatact tcctcgtatt   42000
cgagaagatg cgtcatgtcg aagccggtaa tcgacggatc taactttact tcgtcaactt   42060
cgccgtcaaa tgcccagcca agcgcatggc cccggcacca gcgttggagc cgcgctcctg   42120
cgccttcggc gggcccatgc aacaaaaatt cacgtaaccc cgcgattgaa cgcatttgtg   42180
gatcaaacga gagctgacga tggataccac ggaccagacg gcggttctct tccggagaaa   42240
tcccaccccg accatcactc tcgatgagag ccacgatcca ttcgcgcaga aaatcgtgtg   42300
aggctgctgt gttttctagg ccacgcaacg gcgccaaccc gctgggtgtg cctctgtgaa   42360
gtgccaaata tgttcctcct gtggcgcgaa ccagcaattc gccaccccgg tccttgtcaa   42420
agaacacgac cgtacctgca cggtcgacca tgctctgttc gagcatggct agaacaaaca   42480
tcatgagcgt cgtcttaccc ctcccgatag gcccgaatat tgccgtcatg ccaacatcgt   42540
gctcatgcgg gatatagtcg aaaggcgttc cgccattggt acgaaatcgg gcaatcgcgt   42600
tgccccagtg gcctgagctg gcgccctctg gaaagttttc gaaagagaca aaccctgcga   42660
aattgcgtga agtgattgcg ccagggcgtg tgcgccactt aaaattcccc ggcaattggg   42720
accaataggc cgcttccata ccaataccctt cttggacaac cacggcacct gcatccgcca   42780
ttcgtgtccg agcccgcgcg cccctgtccc caagactatt gagatcgtct gcatagacgc   42840
aaaggctcaa atgatgtgag cccataacga attcgttgct cgcaagtgcg tcctcagcct   42900
cggataattt gccgatttga gtcacggctt tatcgccgga actcagcatc tggctcgatt   42960
tgaggctaag tttcgcgtgc gcttgcgggc gagtcaggaa cgaaaaactc tgcgtgagaa   43020
caagtggaaa atcgagggat agcagcgcgt tgagcatgcc cggccgtgtt tttgcagggt   43080
attcgcgaaa cgaatagatg gatccaacgt aactgtcttt tggcgttctg atctcgagtc   43140
ctcgcttgcc gcaaatgact ctgtcggtat aaatcgaagc gccgagtgag ccgctgacga   43200
ccggaaccgg tgtgaaccga ccagtcatga tcaaccgtag cgcttcgcca atttcggtga   43260
agagcacacc ctgcttctcg cggatgccaa gacgatgcag gccatacgct ttaagagagc   43320
cagcgacaac atgccaaaga tcttccatgt tcctgatctg gcccgtgaga tcgttttccc   43380
tttttccgct tagcttggtg aacctcctct ttaccttccc taaagccgcc tgtgggtaga   43440
caatcaacgt aaggaagtgt tcattgcgga ggagttggcc ggagagcacg cgctgttcaa   43500
aagcttcgtt caggctagcg gcgaaaacac tacggaagtg tcgcggcgcc gatgatggca   43560
cgtcggcatg acgtacgagg tgagcatata ttgacacatg atcatcagcg atattgcgca   43620
acagcgtgtt gaacgcacga caacgcgcat tgcgcatttc agtttcctca agctcgaatg   43680
caacgccatc aattctcgca atggtcatga tcgatccgtc ttcaagaagg acgatatggt   43740
cgctgaggtg gccaatataa gggagataga tctcaccgga tctttcggtc gttccactcg   43800
cgccgagcat cacaccattc ctctcccctcg tgggggaacc ctaattggat ttgggctaac   43860
```

```
agtagcgccc ccccaaactg cactatcaat gcttcttccc gcggtccgca aaaatagcag  43920
gacgacgctc gccgcattgt agtctcgctc cacgatgagc cgggctgcaa accataacgg  43980
cacgagaacg acttcgtaga gcgggttctg aacgataacg atgacaaagc cggcgaacat  44040
catgaataac cctgccaatg tcagtggcac cccaagaaac aatgcgggcc gtgtggctgc  44100
gaggtaaagg gtcgattctt ccaaacgatc agccatcaac taccgccagt gagcgtttgg  44160
ccgaggaagc tcgccccaaa catgataaca atgccgccga cgacgccggc aaccagccca  44220
agcgaagccc gcccgaacat ccaggagatc ccgatagcga caatgccgag aacagcgagt  44280
gactggccga acgaccaag gataaacgtg catatattgt taaccattgt ggcggggtca  44340
gtgccgccac ccgcagattg cgctgcggcg ggtccggatg aggaaatgct ccatgcaatt  44400
gcaccgcaca agcttggggc gcagctcgat atcacgcgca tcatcgcatt cgagagcgag  44460
aggcgattta gatgtaaacg gtatctctca aagcatcgca tcaatgcgca cctccttagt  44520
ataagtcgaa taagacttga ttgtcgtctg cggatttgcc gttgtcctgg tgtggcggtg  44580
gcggagcgat taaaccgcca gcgccatcct cctgcgagcg gcgctgatat gaccccaaa  44640
catcccacgt ctcttcggat tttagcgcct cgtgatcgtc ttttggaggc tcgattaacg  44700
cgggcaccag cgattgagca gctgtttcaa cttttcgcac gtagccgttt gcaaaaccgc  44760
cgatgaaatt accggtgttg taagcggaga tcgcccgacg aagcgcaaat tgcttctcgt  44820
caatcgtttc gccgcctgca taacgacttt tcagcatgtt tgcagcggca gataatgatg  44880
tgcacgcctg gagcgcaccg tcaggtgtca gaccgagcat agaaaaattt cgagagttta  44940
tttgcatgag gccaacatcc agcgaatgcc gtgcatcgag acggtgcctg acgacttggg  45000
ttgcttggct gtgatcttgc cagtgaagcg tttcgccggt cgtgttgtca tgaatcgcta  45060
aaggatcaaa gcgactctcc accttagcta tcgccgcaag cgtagatgtc gcaactgatg  45120
gggcacactt gcgagcaaca tggtcaaact cagcagatga gagtggcgtg gcaaggctcg  45180
acgaacagaa ggagaccatc aaggcaagag aaagcgaccc cgatctctta agcataccct  45240
atctccttag ctcgcaacta acaccgcctc tcccgttgga agaagtgcgt tgttttatgt  45300
tgaagattat cgggagggtc ggttactcga aaattttcaa ttgcttcttt atgatttcaa  45360
ttgaagcgag aaacctcgcc cggcgtcttg gaacgcaaca tggaccgaga accgcgcatc  45420
catgactaag caaccggatc gacctattca ggccgcagtt ggtcaggtca ggctcagaac  45480
gaaaatgctc ggcgaggtta cgctgtctgt aaacccattc gatgaacggg aagcttcctt  45540
ccgattgctc ttggcaggaa tattggccca tgcctgcttg cgctttgcaa atgctcttat  45600
cgcgttggta tcatatgcct tgtccgccag cagaaacgca ctctaagcga ttatttgtaa  45660
aaatgtttcg gtcatcgggc ggtcatgggc ttgacccgct gtcagcgcaa gacggatcgg  45720
tcaaccgtcg gcatcgacaa cagcgtgaat cttggtggtc aaaccgccac gggaacgtcc  45780
catacagcca tcgtcttgat cccgctgttt ccgtcgccg catgttggtg gacgcggaca  45840
caggaactgt caatcatgac gacattctat cgaaagcctt ggaaatcaca ctcagaatat  45900
gatcccagac gtctgcctca cgccatcgta caaagcgatt gtagcaggtt gtacaggaac  45960
cgtatcgatc aggaacgtct gcccagggcg ggcccgtccg gaagcgccac aagatgacat  46020
tgatcacccg cgtcaacgcg cggcacgcga cgcggcttat ttgggaacaa aggactgaac  46080
aacagtccat tcgaaatcgg tgacatcaaa gcggggacgg gttatcagtg gcctccaagt  46140
caagcctcaa tgaatcaaaa tcagaccgat ttgcaaacct gatttatgag tgtgcggcct  46200
```

| | |
|---|---|
| aaatgatgaa atcgtccttc tagatcgcct ccgtggtgta gcaacacctc gcagtatcgc | 46260 |
| cgtgctgacc ttggccaggg aattgactgg caagggtgct ttcacatgac cgctcttttg | 46320 |
| gccgcgatag atgatttcgt tgctgctttg ggcacgtaga aggagagaag tcatatcgga | 46380 |
| gaaattcctc ctggcgcgag agcctgctct atcgcgacgg catcccactg tcgggaacag | 46440 |
| accggatcat tcacgaggcg aaagtcgtca acacatgcgt tataggcatc ttcccttgaa | 46500 |
| ggatgatctt gttgctgcca atctggaggt gcggcagccg caggcagatg cgatctcagc | 46560 |
| gcaacttgcg gcaaaacatc tcactcacct gaaaaccact agcgagtctc gcgatcagac | 46620 |
| gaaggccttt tacttaacga cacaatatcc gatgtctgca tcacaggcgt cgctatccca | 46680 |
| gtcaatacta aagcggtgca ggaactaaag attactgatg acttaggcgt gccacgaggc | 46740 |
| ctgagacgac gcgcgtagac agttttttga aatcattatc aaagtgatgg cctccgctga | 46800 |
| agcctatcac ctctgcgccg gtctgtcgga gagatgggca agcattatta cggtcttcgc | 46860 |
| gcccgtacat gcattggacg attgcagggt caatggatct gagatcatcc agaggattgc | 46920 |
| cgcccttacc ttccgtttcg agttggagcc agccctaaa tgagacgaca tagtcgactt | 46980 |
| gatgtgacaa tgccaagaga gagatttgct taacccgatt ttttgctca agcgtaagcc | 47040 |
| tattgaagct tgccggcatg acgtccgcgc cgaaagaata tcctacaagt aaaacattct | 47100 |
| gcacaccgaa atgcttggtg tagacatcga ttatgtgacc aagatcctta gcagtttcgc | 47160 |
| ttggggaccg ctccgaccag aaataccgaa gtgaactgac gccaatgaca ggaatccctt | 47220 |
| ccgtctgcag ataggtacca tcgatagatc tgctgcctcg cgcgtttcgg tgatgacggt | 47280 |
| gaaaacctct gacacatgca gctcccggag acggtcacag cttgtctgta agcggatgcc | 47340 |
| gggagcagac aagcccgtca gggcgcgtca gcgggtgttg gcgggtgtcg gggcgcagcc | 47400 |
| atgacccagt cacgtagcga tagcggagtg tatactggct taactatgcg gcatcagagc | 47460 |
| agattgtact gagagtgcac catatgcggt gtgaaatacc gcacagatgc gtaaggagaa | 47520 |
| aataccgcat caggcgctct tccgcttcct cgctcactga ctcgctgcgc tcggtcgttc | 47580 |
| ggctgcggcg agcggtatca gctcactcaa aggcggtaat acggttatcc acagaatcag | 47640 |
| gggataacgc aggaaagaac atgtgagcaa aaggccagca aaaggccagg aaccgtaaaa | 47700 |
| aggccgcgtt gctggcgttt ttccataggc tccgcccccc tgacgagcat cacaaaaatc | 47760 |
| gacgctcaag tcagaggtgg cgaaacccga caggactata aagataccag gcgtttcccc | 47820 |
| ctggaagctc cctcgtgcgc tctcctgttc cgaccctgcc gcttaccgga tacctgtccg | 47880 |
| cctttctccc ttcgggaagc gtggcgcttt ctcatagctc acgctgtagg tatctcagtt | 47940 |
| cggtgtaggt cgttcgctcc aagctgggct gtgtgcacga accccccgtt cagcccgacc | 48000 |
| gctgcgcctt atccggtaac tatcgtcttg agtccaaccc ggtaagacac gacttatcgc | 48060 |
| cactggcagc agccactggt aacaggatta gcagagcgag gtatgtaggc ggtgctacag | 48120 |
| agttcttgaa gtggtggcct aactacggct acactagaag gacagtattt ggtatctgcg | 48180 |
| ctctgctgaa gccagttacc ttcggaaaaa gagttggtag ctcttgatcc ggcaaacaaa | 48240 |
| ccaccgctgg tagcggtggt ttttttgttt gcaagcagca gattacgcgc agaaaaaaag | 48300 |
| gatctcaaga agatcctttg atcttttcta cggggtctga cgctcagtgg aacgaaaact | 48360 |
| cacgttaagg gattttggtc atgagattat caaaaaggat cttcacctag atccttttaa | 48420 |
| attaaaaatg aagttttaaa tcaatctaaa gtatatatga gtaaacttgg tctgacagtt | 48480 |
| accaatgctt aatcagtgag gcacctatct cagcgatctg tctatttcgt tcatccatag | 48540 |
| ttgcctgact ccccgtcgtg tagataacta cgatacggga gggcttacca tctggcccca | 48600 |

```
gtgctgcaat gataccgcga gacccacgct caccggctcc agatttatca gcaataaacc    48660
agccagccgg aagggccgag cgcagaagtg gtcctgcaac tttatccgcc tccatccagt    48720
ctattaattg ttgccgggaa gctagagtaa gtagttcgcc agttaatagt ttgcgcaacg    48780
ttgttgccat tgctgcaggg ggggggggg gggggactt ccattgttca ttccacggac    48840
aaaaacagag aaaggaaacg acagaggcca aaaagcctcg ctttcagcac ctgtcgtttc    48900
ctttcttttc agagggtatt ttaaataaaa acattaagtt atgacgaaga agaacgaaa    48960 cgccttaaac cggaaaattt tcataaatag cgaaacccg cgaggtcgcc gccccgtaac    49020
ctgtcggatc accggaaagg acccgtaaag tgataatgat tatcatctac atatcacaac    49080
gtgcgtggag gccatcaaac cacgtcaaat aatcaattat gacgcaggta tcgtattaat    49140
tgatctgcat caacttaacg taaaaacaac ttcagacaat acaaatcagc gacactgaat    49200
acggggcaac ctcatgtccc ccccccccc cccctgcag gcatcgtggt gtcacgctcg    49260
tcgtttggta tggcttcatt cagctccggt tcccaacgat caaggcgagt tacatgatcc    49320
cccatgttgt gcaaaaaagc ggttagctcc ttcggtcctc cgatcgttgt cagaagtaag    49380
ttggccgcag tgttatcact catggttatg gcagcactgc ataattctct tactgtcatg    49440
ccatccgtaa gatgcttttc tgtgactggt gagtactcaa ccaagtcatt ctgagaatag    49500
tgtatgcggc gaccgagttg ctcttgcccg gcgtcaacac gggataatac cgcgccacat    49560
agcagaactt taaaagtgct catcattgga aaacgttctt cggggcgaaa actctcaagg    49620
atcttaccgc tgttgagatc cagttcgatg taacccactc gtgcacccaa ctgatcttca    49680
gcatctttta ctttcaccag cgtttctggg tgagcaaaaa caggaaggca aaatgccgca    49740
aaaaagggaa taagggcgac acggaaatgt tgaatactca tactcttcct ttttcaatat    49800
tattgaagca tttatcaggg ttattgtctc atgagcggat acatatttga atgtatttag    49860
aaaaataaac aaataggggt tccgcgcaca tttccccgaa aagtgccacc tgacgtctaa    49920
gaaaccatta ttatcatgac attaacctat aaaaataggc gtatcacgag gccctttcgt    49980
cttcaagaat tggtcgacga tcttgctgcg ttcggatatt ttcgtggagt tcccgccaca    50040
gacccggatt gaaggcgaga tccagcaact cgcgccagat catcctgtga cggaactttg    50100
gcgcgtgatg actggccagg acgtcggccg aaagagcgac aagcagatca cgcttttcga    50160
cagcgtcgga tttgcgatcg aggatttttt ggcgctgcgc tacgtccgcg accgcgttga    50220
gggatcaagc cacagcagcc cactcgacct tctagccgac ccagacgagc caagggatct    50280
ttttggaatg ctgctccgtc gtcaggcttt ccgacgtttg ggtggttgaa cagaagtcat    50340
tatcgtacgg aatgccaagc actcccgagg ggaaccctgt ggttggcatg cacatacaaa    50400
tggacgaacg gataaacctt ttcacgccct tttaaatatc cgttattcta ataaacgctc    50460
ttttctctta ggtttacccg ccaatatatc ctgtcaaaca ctgatagttt aaactgaagg    50520
cgggaaacga caatctgatc atgagcggag aattaaggga gtcacgttat gaccccgcc    50580 gatgacgcgg gacaagccgt tttacgtttg gaactgacag aaccgcaacg ttgaaggagc    50640
cactcagcaa gctggtacga ttgtaatacg actcactata gggcgaattg agcgctgttt    50700
aaacgctctt caactggaag agcggttact accggttaag tgactagggt c              50751
```

<210> SEQ ID NO 7
<211> LENGTH: 20
<212> TYPE: DNA
<213> ORGANISM: Artificial Sequence
<220> FEATURE:

```
<223> OTHER INFORMATION: Forward primer for GUS expression

<400> SEQUENCE: 7
cggaagcaac gcgtaaactc                                               20

<210> SEQ ID NO 8
<211> LENGTH: 21
<212> TYPE: DNA
<213> ORGANISM: Artificial Sequence
<220> FEATURE:
<223> OTHER INFORMATION: reverse primer for GUS expression

<400> SEQUENCE: 8
tgtgagcgtc gcagaacatt a                                             21

<210> SEQ ID NO 9
<211> LENGTH: 20
<212> TYPE: DNA
<213> ORGANISM: Artificial Sequence
<220> FEATURE:
<223> OTHER INFORMATION: Probe sequence

<400> SEQUENCE: 9
cgcgtccgat cacctgcgtc                                               20

<210> SEQ ID NO 10
<211> LENGTH: 23
<212> TYPE: DNA
<213> ORGANISM: Artificial Sequence
<220> FEATURE:
<223> OTHER INFORMATION: TERM 2.1F primer

<400> SEQUENCE: 10
ctgtcagttc caaacgtaaa acg                                           23

<210> SEQ ID NO 11
<211> LENGTH: 25
<212> TYPE: DNA
<213> ORGANISM: Artificial Sequence
<220> FEATURE:
<223> OTHER INFORMATION: TERM 2.1R primer

<400> SEQUENCE: 11
aatctgatca tgagcggaga attaa                                         25

<210> SEQ ID NO 12
<211> LENGTH: 20
<212> TYPE: DNA
<213> ORGANISM: Artificial Sequence
<220> FEATURE:
<223> OTHER INFORMATION: TERM 1F primer

<400> SEQUENCE: 12
tcccgggtcc ttaggaagac                                               20

<210> SEQ ID NO 13
<211> LENGTH: 21
<212> TYPE: DNA
<213> ORGANISM: Artificial Sequence
<220> FEATURE:
<223> OTHER INFORMATION: TERM 1R primer

<400> SEQUENCE: 13
tggattcagc aggcctagaa g                                             21
```

```
<210> SEQ ID NO 14
<211> LENGTH: 18
<212> TYPE: DNA
<213> ORGANISM: Artificial Sequence
<220> FEATURE:
<223> OTHER INFORMATION: TERM 1P-probe

<400> SEQUENCE: 14
tcctcaggat ttaaatgg                                                 18

<210> SEQ ID NO 15
<211> LENGTH: 20
<212> TYPE: DNA
<213> ORGANISM: Artificial Sequence
<220> FEATURE:
<223> OTHER INFORMATION: Actin_Fwd primer

<400> SEQUENCE: 15
cttcgaatgc ccagcaatgt                                               20

<210> SEQ ID NO 16
<211> LENGTH: 21
<212> TYPE: DNA
<213> ORGANISM: Artificial Sequence
<220> FEATURE:
<223> OTHER INFORMATION: Actin _rev primer

<400> SEQUENCE: 16
gttcgcccac tagcgtacaa c                                             21

<210> SEQ ID NO 17
<211> LENGTH: 15
<212> TYPE: DNA
<213> ORGANISM: Artificial Sequence
<220> FEATURE:
<223> OTHER INFORMATION: Actin _probe

<400> SEQUENCE: 17
tcgaggctgt tcttt                                                    15

<210> SEQ ID NO 18
<211> LENGTH: 460
<212> TYPE: DNA
<213> ORGANISM: Sorghum bicolor

<400> SEQUENCE: 18
aactatctat actgtaataa tgttgtatag ccgccggata gctagctagt tagtcattca    60
gcggcgatgg gtaataataa agtgtcatcc atccatcacc atgggtggca acgtgagcaa   120
tgacctgatt gaacaaattg aaatgaaaag aagaaatatg ttatatgtca acgagatttc   180
ctcataatgc cactgacaac gtgtgtccaa gaaatgtatc agtgatacgt atattcacaa   240 ttttttttatg acttatactc acaatttgtt tttttactac ttatactcga acaatttgtt   300
gtgggtacca taacaatttc gatcgaatat atatcagaaa gttgacgaaa gtaagctcac   360
tcaaaaagtt aaatgggctg cggaagctgc gtcaggccca agttttggct attctatccg   420
gtatccacga ttttgatggc tgagggacat atgttcggct                         460

<210> SEQ ID NO 19
<211> LENGTH: 461
<212> TYPE: DNA
<213> ORGANISM: Artificial Sequence
<220> FEATURE:
<223> OTHER INFORMATION: Consensus Sequence for FIG. 6A-6C
<220> FEATURE:
```

```
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (290)..(291)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t

<400> SEQUENCE: 19
aactatctat actgtaataa tgttgtatag ccgccggata gctagctagt tnagtcattc    60
agcggcgatg ggtaataata aagtgtcatc catccatcac catgggtggc aacgtgagca   120
atgacctgat tgaacaaatt gaaatgaaaa gaagaaatat gttatatgtc aacgagattt   180
cctcataatg ccactgacaa cgtgtgtcca agaaatgtat cagtgatacg tatattcaca   240
atttttttat gacttatact cacaatttgt tttttttacta cttatactcn nacaatttgt   300
tgtgggtacc ataacaattt cgatcgaata tatatcagaa agttgacgaa agtaagctca   360
ctcaaaaagt taaatgggct gcggaagctg cgtcaggccc aagttttggc tattctatcc   420
ggtatccacg attttgatgg ctgagggaca tatgttcgnn t                      461
```